United States Patent
Asokan et al.

(10) Patent No.: US 11,905,312 B2
(45) Date of Patent: Feb. 20, 2024

(54) METHODS AND COMPOSITIONS FOR GENE TRANSFER ACROSS THE VASCULATURE

(71) Applicant: The University of North Carolina at Chapel Hill, Chapel Hill, NC (US)

(72) Inventors: Aravind Asokan, Chapel Hill, NC (US); Giridhar Murlidharan, Quincy, MA (US); Blake Albright, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 999 days.

(21) Appl. No.: 16/485,094

(22) PCT Filed: Feb. 15, 2018

(86) PCT No.: PCT/US2018/018381
§ 371 (c)(1),
(2) Date: Aug. 9, 2019

(87) PCT Pub. No.: WO2018/152333
PCT Pub. Date: Aug. 23, 2018

(65) Prior Publication Data
US 2019/0367562 A1 Dec. 5, 2019

Related U.S. Application Data

(60) Provisional application No. 62/459,286, filed on Feb. 15, 2017.

(51) Int. Cl.
| | |
|---|---|
| *C07K 14/005* | (2006.01) |
| *C12N 7/00* | (2006.01) |
| *C12N 15/86* | (2006.01) |
| *A61K 48/00* | (2006.01) |

(52) U.S. Cl.
CPC .............. *C07K 14/005* (2013.01); *C12N 7/00* (2013.01); *C12N 15/86* (2013.01); *A61K 48/00* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| 7,252,997 B1 | 8/2007 | Hallek et al. | |
| 2003/0053990 A1 | 3/2003 | Rabinowitz et al. | |
| 2015/0238550 A1* | 8/2015 | McCown | A61P 35/00 435/235.1 |

FOREIGN PATENT DOCUMENTS

| WO | 2004027019 | 4/2004 |
| WO | 2015191508 A1 | 12/2015 |
| WO | 2017015102 A1 | 1/2017 |

OTHER PUBLICATIONS

Powell, et al. Characterization of a Novel Adeno-Associated Viral Vector with Preferential Oligodendrocyte Tropism. Gene Therapy, 2016. 23:807-814.*
Partial supplementary European Search Report corresponding to European Patent Application No. 18754551.2 (11 pages) (dated Jan. 13, 2021).
Agbandje-McKenna et al. "AAV Capsid Structure and Cell Interactions" Methods in Molecular Biology, 807:47-92 (2011).
Asokan et al. "Adeno-Associated Virus Type 2 Contains an Integrin alpha5beta1 Binding Domain Essential for Viral Cell Entry" Journal of Virology, 80(18):8961-8969 (2006).
Asokan et al. "Reengineering a receptor footprint of adeno-associated virus enables selective and systemic gene transfer to muscle" Nature Biotechnology, 28(1):79-82 (2010).
Ballabh et al. "The blood-brain barrier: an overview: structure, regulation, and clinical implications" Neurobiology of Disease, 16:1-13 (2004).
Bell et al. "Identification of the Galactose Binding Domain of the Adeno-Associated Virus Serotype 9 Capsid" Journal of Virology, 86(13):7326-7333 (2012).
Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).
Bordoli et al. "Protein structure homology modeling using SWISS-MODEL workspace" Nature Protocols, 4(1):1-13 (2008).
Bowles et al. "Phase 1 Gene Therapy for Duchenne Muscular Dystrophy Using a Translational Optimized AAV Vector" Molecular Therapy, 20(2):443-455 (2012).
Carrillo-Tripp et al. "VIPERdb2: an enhanced and web API enabled relational database for structural virology" Nucleic Acids Research, 37:D436-D442 (2009).
Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).
Cearley et al. "Expanded Repertoire of AAV Vector Serotypes Mediate Unique Patterns of Transduction in Mouse Brain" Molecular Therapy, 16(10):1710-1718 (2008).
Chen et al. "Efficient Transduction of Vascular Endothelial Cells with Recombinant Adeno-Associated Virus Serotype 1 and 5 Vectors" Human Gene Therapy, 16(2):235-247 (2005).
Dipasquale et al. "Identification of PDGFR as a receptor for AAV-5 transduction" Nature Medicine, 9:1306-1312 (2003) (Abstract only).
Emsley et al. "Features and development of Coot" Acta Crystallographica Section D: Biological Crystallography, D66:486-501 (2010).
Felsenstein, Joseph "Confidence Limits on Phylogenies: An Approach Using the Bootstrap" Evolution, 39 (4):783-791 (1985).

(Continued)

*Primary Examiner* — Christopher M Babic
*Assistant Examiner* — Kimberly A Aron
(74) *Attorney, Agent, or Firm* — Myers Bigel, P.A.

(57) ABSTRACT

The present disclosure provides AAV capsid proteins comprising a modification in the amino acid sequence and virus capsids and virus vectors comprising the modified AAV capsid protein. The disclosure also provides methods of administering the virus vectors and virus capsids of the disclosure to a cell or to a subject in vivo.

11 Claims, 19 Drawing Sheets

Specification includes a Sequence Listing.

(56) References Cited

OTHER PUBLICATIONS

Gao et al. "Adeno-associated viruses undergo substantial evolution in primates during natural infections" Proceedings of the National Academy of Sciences, 100(10):6081-6086 (2003).
Gao et al. "Clades of Adeno-associated viruses are widely disseminated in human tissues" Journal of Virology, 78 (12):6381-6388 (2004).
Gray et al. "Preclinical Differences of Intravascular AAV9 Delivery to Neurons and Glia: A Comparative Study of Adult Mice and Nonhuman Primates" Molecular Therapy, 19(6):1058-1069 (2011).
Grieger et al. "Separate Basic Region Motifs within the Adeno-Associated Virus Capsid Proteins Are Essential for Infectivity and Assembly" Journal of Virology, 80(11):5199-5210 (2006).
Hadaczek et al. "Transduction of Nonhuman Primate Brain with Adeno-Associated Virus Serotype 1: Vector Trafficking and Immune Response" Human Gene Therapy, 20(3):225-237 (2009).
Huang et al. "Parvovirus glycan interactions" Current Opinion in Virology, 7:108-118 (2014).
Huang et al. "Characterization of the Adeno-Associated Virus 1 and 6 Sialic Acid Binding Site" Journal of Virology, 90 (11):5219-5230 (2016).
International Preliminary Report on Patentability corresponding to International Patent Application No. PCT/US2018/018381 (10 pages) (dated Aug. 29, 2019).
Kashiwakura et al. "Hepatocyte Growth Factor Receptor Is a Coreceptor for Adeno-Associated Virus Type 2 Infection" Journal of Virology, 79(1)609-614 (2005).
Krissinel et al. "Secondary-structure matching (SSM), a new tool for fast protein structure alignment in three dimensions" Acta Crystallographica Section D: Biological Crystallography, D60:2256-2268 (2004).
Kumar et al. "MEGA7: Molecular Evolutionary Genetics Analysis Version 7.0 for Bigger Datasets" Molecular Biology and Evolution, 33(7):1870-1874 (2016).
Lein et al. "Genome-wide atlas of gene expression in the adult mouse brain" Nature, 445(7124):168-176 (2007) (Abstract only).
Li et al. "Single Amino Acid Modification of Adeno-Associated Virus Capsid Changes Transduction and Humoral Immune Profiles" Journal of Virology, 86(15):7752-7759 (2012).
Madigan et al. "Engineering AAV receptor footprints for gene therapy" Current Opinion in Virology, 18:89-96 (2016).
Miller et al. "Production, purification and preliminary X-ray crystallographic studies of adeno-associated virus serotype 1" Acta Crystallographica Section F: Structural Biology and Crystallization Communications, 62(Pt 12):1271-1274 (2006).
Mingozzi et al. "Immune responses to AAV vectors: overcoming barriers to successful gene therapy" Blood, 122 (1):23-36 (2013).
Murlidharan et al. "Biology of adeno-associated viral vectors in the central nervous system" Frontiers in Molecular Neuroscience, 7(76):1-9 (2014).
Murlidharan et al. "CNS-restricted Transduction and CRISPR/Cas9-mediated Gene Deletion with an Engineered AAV Vector" Molecular Therapy: Nucleic Acids, 5:e338 (2016).
Murlidharan et al. "Glymphatic fluid transport controls paravascular clearance of AAV vectors from the brain" JCI Insight, 1(14):e88034 (2016).
Nam et al. "Structure of Adeno-Associated Virus Serotype 8, a Gene Therapy Vector" Journal of Virology, 81 (22):12260-12271 (2007).
Nathwani et al. "Long-Term Safety and Efficacy of Factor IX Gene Therapy in Hemophilia B" The New England Journal of Medicine, 371(21):1994-2004 (2014).
Pillay et al. "An essential receptor for adeno-associated virus infection" Nature, 530(7588):108-112 (2016).
Pulicherla et al. "Engineering Liver-detargeted AAV9 Vectors for Cardiac and Musculoskeletal Gene Transfer" Molecular Therapy, 19(6):1070-1078 (2011).
Rosenberg et al. "Comparative Efficacy and Safety of Multiple Routes of Direct CNS Administration of Adeno-Associated Virus Gene Transfer Vector Serotype rh.10 Expressing the Human Arylsulfatase A cDNA to Nonhuman Primates" Human Gene Therapy Clinical Development, 25(3):164-177 (2014).
Saitou et al. "The Neighbor-joining Method: A New Method for Reconstructing Phylogenetic Trees" Molecular Biology and Evolution, 4(4):406-425 (1987).
Salinas et al. "A hitchhiker's guide to the nervous system: the complex journey of viruses and toxins" Nature Reviews Microbiology, 8(9):645-655 (2010) (Abstract only).
Sonntag et al. "Adeno-Associated Virus Type 2 Capsids with Externalized VP1/VP2 Trafficking Domains Are Generated prior to Passage through the Cytoplasm and Are Maintained until Uncoating Occurs in the Nucleus" Journal of Virology, 80(22):11040-11054 (2006).
Weller et al. "Epidermal growth factor receptor is a co-receptor for adeno-associated virus serotype 6" Nature Medicine, 16(6):662-664 (2010).
Williams et al. "Monocyte maturation, HIV susceptibility, and transmigration across the blood brain barrier are critical in HIV neuropathogenesis" Journal of Leukocyte Biology, 91(3):401-415 (2012).
Wu et al. "Alpha2,3 and alpha2,6 N-Linked Sialic Acids Facilitate Efficient Binding and Transduction by Adeno-Associated Virus Types 1 and 6" Journal of Virology, 80(18):9093-9103 (2006).
Xiao et al. "Interpretation of Electron Density with Stereographic Roadmap Projections" Journal of Structural Biology, 158(2):182-187 (2007).
Yang et al. "Global CNS Transduction of Adult Mice by Intravenously Delivered rAAVrh.8 and rAAVrh.10 and Nonhuman Primates by rAAVrh.10" Molecular Therapy, 22(7):1299-1309 (2014).
Zhang et al. "Several rAAV Vectors Efficiently Cross the Blood-brain Barrier and Transduce Neurons and Astrocytes in the Neonatal Mouse Central Nervous System" Molecular Therapy, 19(8):1440-1448 (2011).
Extended European Search Report corresponding to European Patent Application No. 18754551.2 (11 pages) (dated Jun. 4, 2021).
International Search Report and the Written Opinion of the International Searching Authority corresponding to International Patent Application No. PCT/US2018/018381 (15 pages) (dated Jul. 5, 2018).

* cited by examiner

|          | 260 | 260 | 270 | 280 |
|----------|-----|-----|-----|-----|
| AAV1RX   | 259 | QISNGTSGGSTNDNTYFGYSTPW |||
| AAV1     | 259 | QISSASTG-ASNDNHYFGYSTPW |||
| AAV2     | 259 | QISSQS---GASNDNHYFGYSTPW |||
| AAV3     | 259 | QISSQS---GASNDNHYFGYSTPW |||
| AAV4     | 254 | RLGESLQS------NTYNGFSTPW |||
| AAV5     | 249 | EIKSGS-VDGSNANAYFGYSTPW |||
| AAV6     | 259 | QISSASTG-ASNDNHYFGYSTPW |||
| AAV7     | 260 | QISSETAG-STNDNTYFGYSTPW |||
| AAV8     | 260 | QISNGTSGGATNDNTYFGYSTPW |||
| AAV9     | 259 | QISNSTSGGSSNDNAYFGYSTPW |||
| AAVrh.8  | 259 | QISNGTSGGSTNDNTYFGYSTPW |||
| AAVrh.10 | 260 | QISNGTSGGSTNDNTYFGYSTPW |||
| AAVrh.39 | 260 | QISNGTSGGSTNDNTYFGYSTPW |||
| AAVrh.43 | 259 | QISNGTSGGATNDNTYFGYSTPW |||
| Consensus| 260 | QISNGTSGGATNDNTYFGYSTPW |||

FIG. 14

| | |
|---|---|
| AAV1    | MAADGYLPDWLEDNLSEGIREWWDLKPGAPKPKANQQKQDDGRGLVLPGY |
| AAV1R7  | MAADGYLPDWLEDNLSEGIREWWDLKPGAPKPKANQQKQDDGRGLVLPGY |
| AAVrh.10| MAADGYLPDWLEDNLSEGIREWWDLKPGAPKPKANQQKQDDGRGLVLPGY |
| | |
| AAV1    | KYLGPFNGLDKGEPVNAADAAALEHDKAYDQQLKAGDNPYLRYNHADAEF |
| AAV1R7  | KYLGPFNGLDKGEPVNAADAAALEHDKAYDQQLKAGDNPYLRYNHADAEF |
| AAVrh.10| KYLGPFNGLDKGEPVNAADAAALEHDKAYDQQLKAGDNPYLRYNHADAEF |
| | |
| AAV1    | QERLQEDTSFGGNLGRAVFQAKKRVLEPLGLVEEGAKTAPGKKRPVEQSP |
| AAV1R7  | QERLQEDTSFGGNLGRAVFQAKKRVLEPLGLVEEGAKTAPGKKRPVEPSP |
| AAVrh.10| QERLQEDTSFGGNLGRAVFQAKKRVLEPLGLVEEGAKTAPGKKRPVEPSP |
| | |
| AAV1    | Q-EPDSSSGIGKTGQQPAKKRLNFGQTGDSESVPDPQPLGEPPATPAAVG |
| AAV1R7  | QRSPDSSTGIGKKGQQPAKKRLNFGQTGDSESVPDPQPIGEPPATPAAVG |
| AAVrh.10| QRSPDSSTGIGKKGQQPAKKRLNFGQTGDSESVPDPQPIGEPPAGPSGLG |
| | |
| AAV1    | PTTMASGGGAPMADNNEGADGVGNASGNWHCDSTWLGDRVITTSTRTWAL |
| AAV1R7  | PTTMAAGGGAPMADNNEGADGVGSSSGNWHCDSTWLGDRVITTSTRTWAL |
| AAVrh.10| SGTMAAGGGAPMADNNEGADGVGSSSGNWHCDSTWLGDRVITTSTRTWAL |
| | |
| AAV1    | PTYNNHLYKQISSASTG-ASNDNHYFGYSTPWGYFDFNRFHCHFSPRDWQ |
| AAV1R7  | PTYNNHLYKQISNGTSGGSTNDNTYFGYSTPWGYFDFNRFHCHFSPRDWQ |
| AAVrh.10| PTYNNHLYKQISNGTSGGSTNDNTYFGYSTPWGYFDFNRFHCHFSPRDWQ |
| | |
| AAV1    | RLINNNWGFRPKRLNFKLFNIQVKEVTTNDGVTTIANNLTSTVQVFSDSE |
| AAV1R7  | RLINNNWGFRPKRLNFKLFNIQVKEVTQNEGTKTIANNLTSTIQVFTDSE |
| AAVrh.10| RLINNNWGFRPKRLNFKLFNIQVKEVTQNEGTKTIANNLTSTIQVFTDSE |
| | |
| AAV1    | YQLPYVLGSAHQGCLPPFPADVFMIPQYGYLTLNNGSQAVGRSSFYCLEY |
| AAV1R7  | YQLPYVLGSAHQGCLPPFPADVFMIPQYGYLTLNNGSQAVGRSSFYCLEY |
| AAVrh.10| YQLPYVLGSAHQGCLPPFPADVFMIPQYGYLTLNNGSQAVGRSSFYCLEY |
| | |
| AAV1    | FPSQMLRTGNNFTFSYTFEEVPFHSSYAHSQSLDRLMNPLIDQYLYYLNR |
| AAV1R7  | FPSQMLRTGNNFTFSYTFEEVPFHSSYAHSQSLDRLMNPLIDQYLYYLNR |
| AAVrh.10| FPSQMLRTGNNFEFSYQFEDVPFHSSYAHSQSLDRLMNPLIDQYLYYLSR |
| | |
| AAV1    | TQNQSGSAQNKDLLFSRGSPAGMSVQPKNWLPGPCYRQQRVSKTKTDNNN |
| AAV1R7  | TQNQSGSAQNKDLLFSRGSPAGMSVQPKNWLPGPCYRQQRVSKTKTDNNN |
| AAVrh.10| TQSTGGTAGTQQLLFSQAGPNNMSAQAKNWLPGPCYRQQRVSTTLSQNNN |
| | |
| AAV1    | SNFTWTGASKYNLNGRESIINPGTAMASHKDDEDKFFPMSGVMIFGKESA |
| AAV1R7  | SNFTWTGASKYNLNGRESIINPGTAMASHKDDEDKFFPMSGVMIFGKESA |
| AAVrh.10| SNFAWTGATKYHLNGRDSLVNPGVAMATHKDDEERFFPSSGVLMFGKQGA |
| | |
| AAV1    | GASNTALDNVMITDEEEIKATNPVATERFGTVAVNFQSSSTDPATGDVHA |
| AAV1R7  | GASNTALDNVMITDEEEIKATNPVATERFGTVAVNFQSSSTDPATGDVHA |
| AAVrh.10| GKDNVDYSSVMLTSEEEIKTTNPVATEQYGVVADNLQQQNAAPIVGAVNS |
| | |
| AAV1    | MGALPGMVWQDRDVYLQGPIWAKIPHTDGHFHPSPLMGGFGLKNPPPQIL |
| AAV1R7  | MGALPGMVWQDRDVYLQGPIWAKIPHTDGHFHPSPLMGGFGLKNPPPQIL |
| AAVrh.10| QGALPGMVWQNRDVYLQGPIWAKIPHTDGNFHPSPLMGGFGLKHPPPQIL |
| | |
| AAV1    | IKNTPVPANPPAEFSATKFASFITQYSTGQVSVEIEWELQKENSKRWNPE |
| AAV1R7  | IKNTPVPANPPAEFSATKFASFITQYSTGQVSVEIEWELQKENSKRWNPE |
| AAVrh.10| IKNTPVPADPPTTFSQAKLASFITQYSTGQVSVEIEWELQKENSKRWNPE |
| | |
| AAV1    | VQYTSNYAKSANVDFTVDNNGLYTEPRPIGTRYLTRPL |
| AAV1R7  | VQYTSNYAKSANVDFTVDNNGLYTEPRPIGTRYLTRPL |
| AAVrh.10| IQYTSNYYKSTNVDFAVNTDGTYSEPRPIGTRYLTRNL |

FIG. 15

METHODS AND COMPOSITIONS FOR GENE TRANSFER ACROSS THE VASCULATURE

CROSS REFERENCE

This application is a 35 U.S.C. § 371 national phase application of International Application Serial No. PCT/US2018/018381 filed Feb. 15, 2018, which claims the benefit, under 35 U.S.C. § 119(e), of U.S. Provisional Application No. 62/459,286 filed Feb. 15, 2017, the entire contents of each of which are incorporated by reference herein in their entirety for all purposes.

STATEMENT OF GOVERNMENT SUPPORT

This invention was made with government support under Grant Numbers HL112761 and HL089221 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470.804_09152022_ST25.txt, 224,307 bytes in size, generated on Sep. 15, 2022 and filed via EFS-Web, is provided in lieu of a paper copy. This Sequence Listing is incorporated by reference into the specification for its disclosures.

FIELD OF THE INVENTION

The present invention relates to modified capsid proteins from adeno-associated virus (AAV) and virus capsids and virus vectors comprising the same. In particular, the invention relates to modified AAV capsid proteins and capsids comprising the same that can be incorporated into virus vectors to confer a desirable transduction profile with respect to a target tissue(s) of interest.

BACKGROUND OF THE INVENTION

New adeno-associated virus (AAV) strains isolated from animal tissues and adenoviral stocks have expanded the panel of AAV vectors available for therapeutic gene transfer applications. Comprehensive efforts to map tissue tropisms of these AAV isolates in animal models are currently underway. The ability to direct homing of AAV vectors to selective organs is useful for gene therapy and other therapeutic applications.

The present invention addresses a need in the art for nucleic acid delivery vectors with desirable targeting features.

SUMMARY OF THE INVENTION

In some embodiments, the present disclosure provides an adeno-associated virus (AAV) capsid protein, wherein the AAV capsid protein comprises a modification at amino acid residues S262, A263, S264, T265, A267, S268 and H272, and a single amino acid residue insertion between residues G266 and A267, (VP1 numbering), wherein the numbering of each residue is based on the amino acid sequence of AAV1 (SEQ ID NO:1) or the equivalent amino acid residue in AAV2 (SEQ ID NO:2), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the AAV capsid protein of this invention can further comprise a modification at amino acid residues Q148, E152, S157, T162, T326, D328, V330, T331, V341 and S345, and a single amino acid residue insertion between residues E152 and P153 (VP1 numbering) wherein the numbering of each residue is based on the amino acid sequence of SEQ ID NO:1 or the equivalent amino acid residue in SEQ ID NOs:2, 3, 4, 5, 6, 7 or 8. In further embodiments, the AAV capsid protein of this invention can further comprise a modification of amino acid residues L188, S205, N223 and A224 (VP1 numbering), wherein the numbering of each residue is based on the amino acid sequence of SEQ ID NO:1 or the equivalent amino acid residue in SEQ ID NOs:2, 3, 4, 5, 6, 7 or 8.

In some embodiments, the present disclosure provides an adeno-associated virus (AAV) capsid protein, wherein the AAV capsid protein comprises a modification at amino acid residues S262, A263, S264, T265, and A267 (VP1 numbering), and a single amino acid residue insertion between residues S268 and N269, wherein the amino acid residues are based on the amino acid sequence of AAV1 (SEQ ID NO:1) or the equivalent amino acid residues in AAV2 (SEQ ID NO:2), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the capsid protein further comprises a modification at amino acid residue H272. In some embodiments, the AAV capsid protein further comprises a modification at amino acid residues Q148, E152, S157, T162, H272, T326, D328, V330, T331, V341 and S345, and a single amino acid residue insertion between residues E152 and P153. In further embodiments, the AAV capsid protein further comprises a modification at amino acid residues L188, S205, N223, A224, and H272.

In some embodiments, the disclosure provides an adeno-associated virus (AAV) capsid protein, wherein the AAV capsid protein comprises a modification resulting in the amino acid sequence: $X^1$-$X^2$-$X^3$-$X^4$ (SEQ ID NO:35) at the amino acids corresponding to amino acid positions 262 to 265 (VP1 numbering) of the native AAV1 capsid protein (SEQ ID NO:1), wherein $X^1$ is any amino acid other than S; wherein $X^2$ is any amino acid other than A; wherein $X^3$ is any amino acid other than S; and wherein $X^4$ is any amino acid other than T.

In some embodiments, the disclosure provides an adeno-associated virus (AAV) capsid protein, wherein the AAV capsid protein comprises a modification at amino acid residues S262, A263, S264, T265, A267, and H272, and a single amino acid residue insertion between residues S268 and N269, (VP1 numbering), wherein the numbering of each residue is based on the amino acid sequence of AAV1 (SEQ ID NO:2) or the equivalent amino acid residue in AAV1 (SEQ ID NO:1), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8).

In some embodiments, the disclosure provides an adeno-associated virus (AAV) capsid protein, wherein the AAV capsid protein comprises a modification at amino acid residues S262, Q263, S264, A266, S267, and H271, and a insertion of at least one amino acid residue between residues S261 and S262, (VP1 numbering), wherein the numbering of each residue is based on the amino acid sequence of AAV2 (SEQ ID NO:2) or the equivalent amino acid residue in AAV1 (SEQ ID NO:1), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8).

In some embodiments, the disclosure provides an adeno-associated virus (AAV) capsid protein, wherein the AAV capsid protein comprises a modification at amino acid residues S262, Q263, S264, A266, A267, H271, and a single amino acid residue insertion between residues S261 and S262, wherein the numbering of each residue is based on the amino acid sequence of AAV3 (SEQ ID NO:3) or the equivalent amino acid residue in AAV1 (SEQ ID NO:1), AAV2 (SEQ ID NO:2), AAV6 (SEQ ID NO:4), AAV7 (SEQ ID NO:5), AAV8 (SEQ ID NO:6), AAV9 (SEQ ID NO:7) or AAVrh10 (SEQ ID NO:8).

In some embodiments, the disclosure provides an adeno-associated virus (AAV) capsid protein, wherein the AAV capsid protein comprises a modification at amino acid residues S263, S269, A237 (VP1 numbering), wherein the numbering of each residue is based on the amino acid sequence of AAV9 (SEQ ID NO:9) or the equivalent amino acid residue in AAV1 (SEQ ID NO:1), AAV2 (SEQ ID NO:2), AAV3 (SEQ ID NO:3), AAV6 (SEQ ID NO:4), AAV7 (SEQ ID NO:5), AAV8 (SEQ ID NO:6), or AAVrh10 (SEQ ID NO:8).

In some embodiments, the disclosure provides an adeno-associated virus (AAV) capsid protein, wherein the AAV capsid protein comprises the sequence of any one of SEQ ID NO:9 to SEQ ID NO:34.

The present disclosure additionally provides an AAV capsid comprising a capsid protein of the disclosure, as well as a virus vector comprising an AAV capsid of the disclosure. In some embodiments, the virus vector comprises an AAV capsid of the disclosure and a nucleic acid comprising at least one terminal repeat sequence, wherein the nucleic acid is encapsidated by the AAV capsid.

The present disclosure additionally provides pharmaceutical compositions comprising the AAV capsids and/or the virus vectors disclosed herein.

Also provided herein is a method of introducing a nucleic acid molecule into a cell, comprising contacting the cell with a virus vector of the disclosure, as well as a method of delivering a nucleic acid molecule to a subject, comprising administering to the subject a virus vector of the disclosure.

Furthermore, the present disclosure provides a method of selectively delivering a nucleic acid molecule of interest to a neuronal cell, comprising contacting the neuronal cell with the virus vector of this invention, wherein the virus vector comprises the nucleic acid molecule of interest.

In yet another embodiment, the present disclosure provides a method of treating a neurological disorder or defect in a subject, comprising administering to the subject a virus vector of the disclosure, wherein the virus vector comprises a nucleic acid molecule that encodes a therapeutic protein or therapeutic RNA effective in treating the neurological disorder or defect.

These and other aspects are addressed in more detail in the description set forth below.

BRIEF DESCRIPTION OF THE DRAWINGS

FIG. 4A. Schematic of the panel of representative AAV1/rh.10 chimeric capsids isolated from the library demonstrating sequence diversity, at the amino acid level, of domain swaps obtained through shuffling. Individual parental or chimeric capsids are listed vertically, while the VP1 capsid sequence with different domain swaps is displayed horizontally, from the N-terminus on the left to the C-terminus on the right. AAV1-derived residues are shown in gray, AAVrh.10 residues in light gray and consensus residues between the two in black. FIG. 4B. Neighbor-joining phylogeny of the VP1 capsid sequences of AAV1/rh.10 chimeric capsids. Capsid amino acid sequences were aligned with ClustalW and the phylogeny was generated using a neighbor-joining algorithm. A Poisson correction was used to calculate amino acid distances, represented as units of the number of amino acid substitutions per site. The tree is drawn to scale, with branch lengths in the same units as those of the evolutionary distances used to infer the tree. Bootstrap values were calculated with 1000 replicates and the percentage of replicate trees in which the associated taxa clustered together are shown next to the branches. FIG. 4C. Three-dimensional surface models of capsid subunit trimer/3-fold symmetry axis regions of parental and representative chimeric AAV capsid mutants selected for in vivo screening. Structural models were visualized and generated using PyMol.

(FIG. 9A) The sequence alignment of residues 140-172, 260-282 and 320-352 of each of AAV1R6 (SEQ ID NO:16), AAV1 (SEQ ID NO:1) and AAVrh.10 (SEQ ID NO:8) wherein the numbering corresponds to AAV1R6 numbering highlights the amino acid residues that are uniquely derived from AAVrh.10. The three-dimensional structural model of the chimeric AAV1R6 VP3 subunit (FIG. 9B) monomer was generated using SWISS-MODEL with the crystal structure of AAV8 serving as the template for homology modeling (PDB ID: 2QAO). Surface models of the AAV1R6 VP3 subunit (FIG. 9C) trimer dimer/2-fold axis of symmetry, (FIG. 9D) trimer/three-fold axis of symmetry, (FIG. 9E) pentamer/5-fold axis of symmetry and (FIG. 9F) surface rendering of an intact AAV1R6 capsid (60mer) were generated via the VIPERdb oligomer generator and were visualized using PyMol. Residues derived from AAV1 are colored in dark gray while residues derived from AAVrh.10, clustered at the base of the protrusions at the 3-fold axis of symmetry, depression at the 2-fold axis of symmetry and at the 5-fold pore, are colored in light gray.

FIG. 10A. GFP fluorescence for cardiac (top panel) and liver (bottom panel) tissues in mice treated with either PBS (Mock), AAV1, AAVrh.10, AAV1R6 or AAV1R7. FIG. 10B. Transduction levels for cardiac (top) and liver (bottom) measured by quantifying relative fluorescence across multiple images taken for each treatment. The bars represent the range from lowest to highest values with the center line representing the average across samples. Relative fluorescence was normalized to mock treated tissues. Error bars represent standard deviation (n=3). One-way ANOVA and unpaired two-tailed T-test with Welch's correction for each group were carried out and significance relative to AAVrh.10 is shown. ns, not significant. *, $P<0.05$.

FIG. 11A The sequence alignment of AAV1RX (SEQ ID NO:9) with AAV1 (SEQ ID NO:1) and AAVrh.10 (SEQ ID NO:8) shows the numbered amino acid residues within and adjacent to the neurotropic footprint. Residues shown correspond to residues 260 to 282 of SEQ ID NO:1, 8 and 9, wherein the numbering corresponds to AAVrh.10 numbering (SEQ ID NO:8). Conserved residues are highlighted in light gray, the residues composing the footprint are highlighted in dark gray and non-conserved residues are highlighted in either black lettering or white. Structural models of the engineered AAV1RX chimeric capsid were generated using SWISS-MODEL software for homology-based modelling and VIPERdb was used to generate oligomers. PyMol was used to generate surface rendered models of the AAV1RX VP3 subunit monomer (FIG. 11B), trimer dimer/2-fold axis of symmetry (FIG. 11C), trimer/three-fold axis of symmetry (FIG. 11D), pentamer/5-fold axis of symmetry (FIG. 11E) and the full capsid (60-mer) (FIG. 11F). AAV1-derived amino acids and those homologous between AAV1 and AAVrh.10 are represented in dark gray while the residues comprising the neurotropic footprint from AAVrh.10 for crossing the BBB are depicted in light gray. FIG. 11G. The stereographic roadmap projection shows the neurotropic footprint as viewed down the threefold symmetry axis on the AAV1RX capsid and was generated using RIVEM. Only surface-exposed amino acid residues are shown, with the boundaries between each delineated with black lines. The light regions depict the topological protrusions at the threefold axis of symmetry while the dark regions represent topological depressions. The key amino acid residues of this footprint are labeled (AAVrh.10 VP1 numbering). FIG. 11H. CNS transduction profile of AAV1RX packaging a CBh-scGFP transgene administered via tail vein injection at a dose of $5\times10^{11}$. vg. Sections taken at 21 days post injection were immunostained and imaged. Scale bar=100 µm.

FIG. 14. Sequence alignment of 1RX footprint, and Variable Region I (VR-I) across common AAV serotypes. The sequence alignment of AAV1RX with common AAV serotypes highlights the amino acid residues (VP1 numbering) of the 1RX footprint, within the larger context of variable region I (VR-I), compared across common natural AAV serotypes. Black lines above and below demarcate the specific residues within the 1RX footprint. This sequence alignment was generated using Vector NTI Advance 11.5.2 software and shows residues 260 to 282 of SEQ ID NO:9 (AAV1RX), SEQ ID NO:1 (AAV1), SEQ ID NO:2 (AAV2), SEQ ID NO:3 (AAV3), SEQ ID NO:4 (AAV6), SEQ ID NO:5 (AAV7), SEQ ID NO:6 (AAV8), SEQ ID NO:7 (AAV9), and SEQ ID NO:8 (AAVrh.10), wherein the numbering corresponds to AAV1RX (SEQ ID NO:9). The sequences corresponding to the same residues are shown for AAV4 (SEQ ID NO:47), AAV5 (SEQ ID NO:48), AAVrh.8 (SEQ ID NO:49), AAVrh.39 (SEQ ID NO:50), and AAVrh.43 (SEQ ID NO:51).

FIG. 15. Sequence alignment of AAV1 (SEQ ID NO: 1), AAV1R7 (SEQ ID NO:16), and AAVrh.10 (SEQ ID NO:8) VP1 capsid protein.

DETAILED DESCRIPTION

Figure 1:
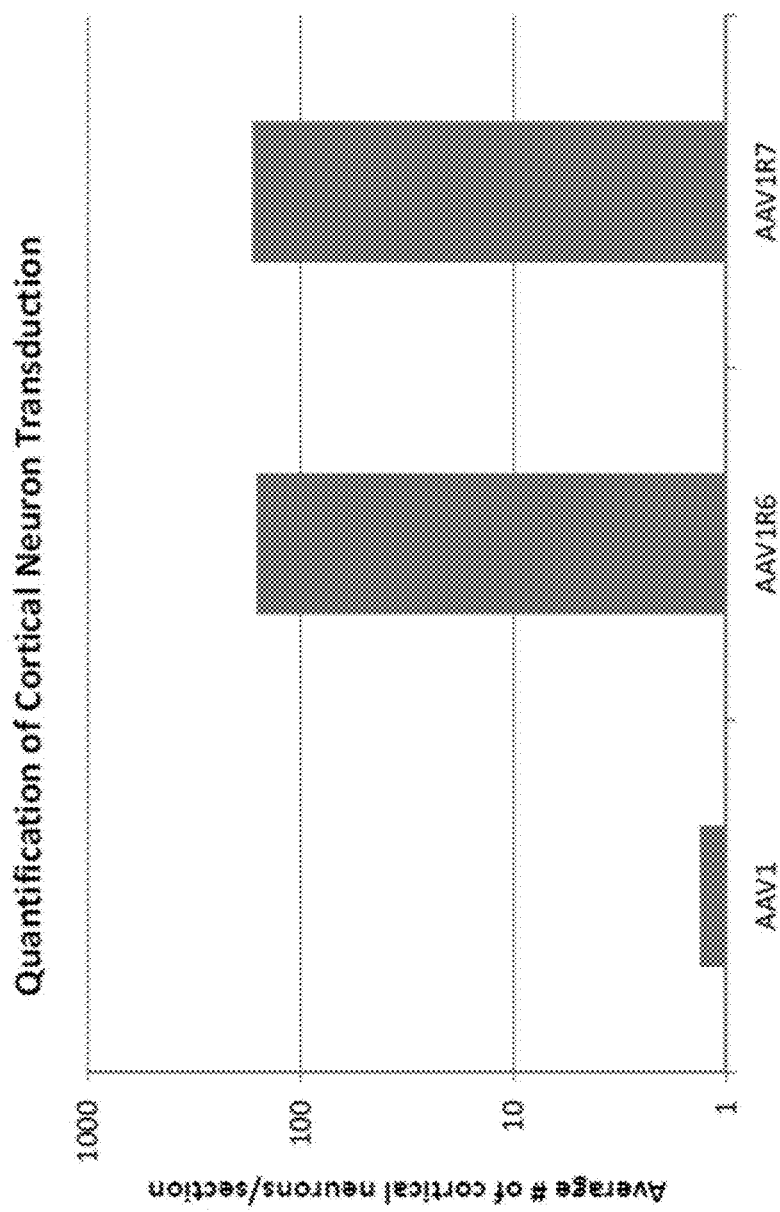
FIG. 1. Quantification of cortical neuron transduction. 6-8 week old female BL6 mice were administered systemically via tail vein injections with a dose of $5 \times 10^{11}$ vg (vector genomes) of vectors packaging CBh-scGFP (AAV1, AAV1R6 or AAV1R7) or with PBS as a negative control. Mice were sacrificed 21 days post injection and tissues were harvested, fixed, and sectioned. Tissues were immunostained for GFP using a DAB substrate, GFP expression was visualized via slide scanning and ImageScope software. GFP positive neurons in the cerebral cortex were manually counted, quantified and averaged across multiple coronal brain sections per mouse. N=2 for AAV1; n=3 for AAV1R6 and AAV1R7.
Figure 2:
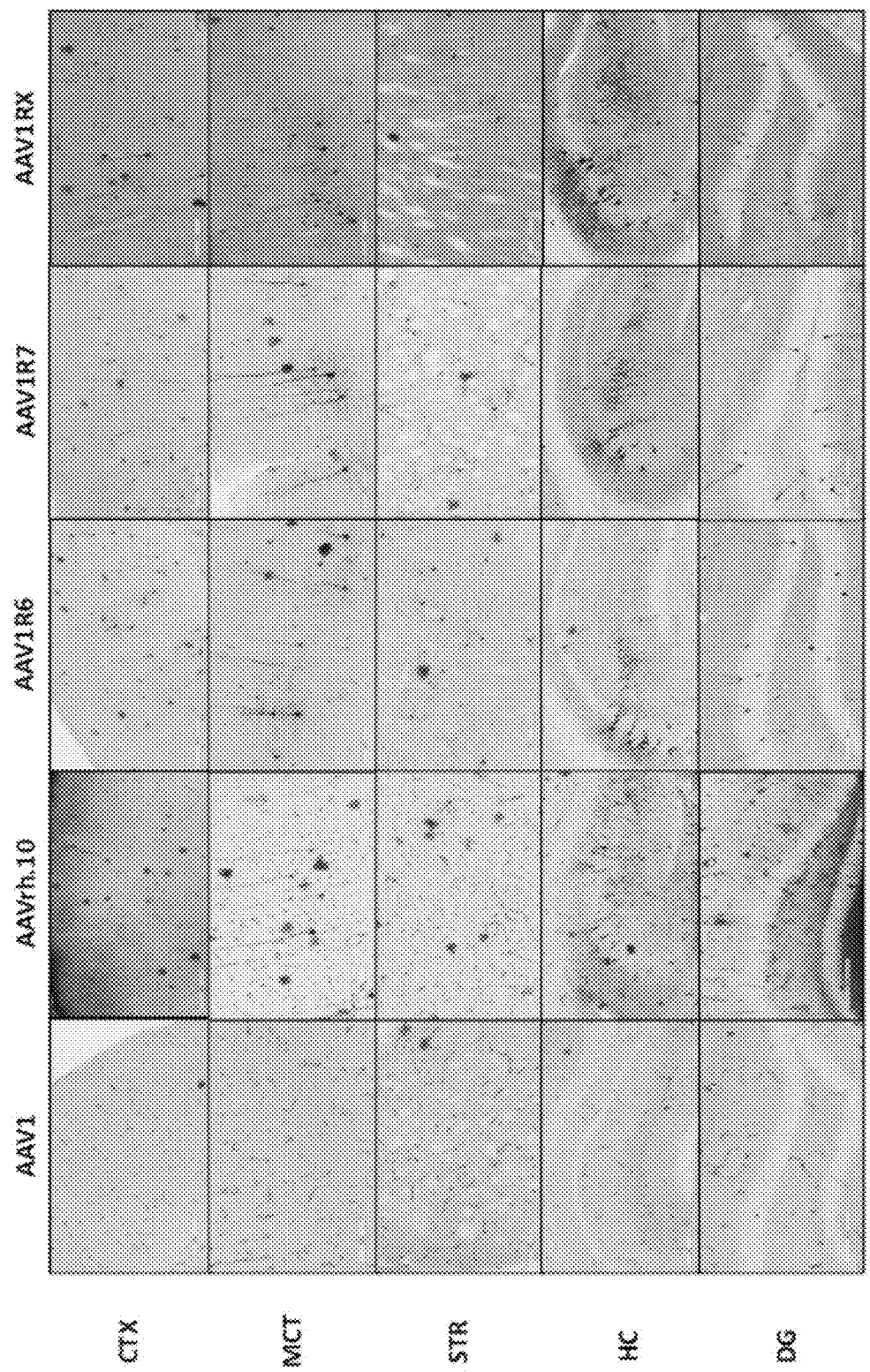
FIG. 2. Crossing the brain vasculature and neuronal expression. AAV vectors packaging a Cbh-scGFP transgene were administered to C57/B16 mice via tail vein injection at a dose of $5 \times 10^{11}$ vg. Mice were sacrificed at 21 days post injection, tissues were harvested, fixed, sectioned, DAB-stained to detect GFP, imaged via Aperio Scanner and image processing performed with ImageScope software. Abbreviations: Cortex (CTX), motor cortex (MCT), striatum (STR), hippocampus (HC), dentate gyrus (DG). N=3.

Unless otherwise defined, all technical and scientific terms used herein have the same meaning as commonly understood by one of ordinary skill in the art to which this disclosure belongs. The terminology used herein is for the purpose of describing particular embodiments only and is not intended to be limiting. All publications, patent applications, patents, and other references mentioned herein are incorporated by reference herein in their entirety.

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, 10%, +5%, +1%, +0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 USPQ 461, 463 (CCPA 1976) (emphasis in the original); see also MPEP § 2111.03. Thus, the term "consisting essentially of" when used in a claim herein is not intended to be interpreted to be equivalent to "comprising."

Unless the context indicates otherwise, it is specifically intended that the various features of the capsid proteins, vectors, compositions, and methods described herein can be used in any combination.

Moreover, the present disclosure also contemplates that in some embodiments, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more, relative to a control or reference.

As used herein, the terms "increase," increases" "increasing," "enhance," "enhances," "enhancement" and similar terms indicate an increase or enhancement of at least about 5%, 10%, 20%, 25%, 50%, 75%, 100%, 150%, 200%, 300%, 400%, 500% or more, relative to a control or reference.

The term "parvovirus" as used herein encompasses the family Parvoviridae, including autonomously replicating parvoviruses and dependoviruses. The autonomous parvoviruses include members of the genera *Parvovirus, Erythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type rh10, AAV type 11, AAV type 12, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al. (2004) *J. Virology* 78:6381-6388; Moris et al. (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as the GenBank© Database. See, e.g., GenBank Accession Numbers NC_044927, NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J. Virol.* 58:921; Gao et al. (2002) *Proc. Nat. Acad. Sci. USA* 99:11854; Moris et al. (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 and 70 (4th ed., Lippincott-Raven Publishers). See also, description of the crystal structure of AAV2 (Xie et al. (2002) *Proc. Nat. Acad. Sci.* 99:10405-10), AAV4 (Padron et al. (2005) *J. Virol.* 79: 5047-58), AAV5 (Walters et al. (2004) *J. Virol.* 78: 3361-71) and CPV (Xie et al. (1996) *J. Mol. Biol.* 6:497-520; Tsao et al. (1991) *Science* 251:1456-64; Drouin et al. (2013) *Future Virol.* 8(12):1183-1199).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest. Those skilled in the art will appreciate that, in some embodiments, transcription of a heterologous nucleic acid sequence from a viral genome may not be initiated in the absence of trans-acting factors, e.g., for an inducible promoter or otherwise regulated nucleic acid sequence. In the case of a recombinant AAV (rAAV) genome, gene expression from the viral genome may be from a stably integrated provirus and/or from a non-integrated episome, as well as any other form the virus may take within the cell.

As used here, "systemic tropism" and "systemic transduction" (and equivalent terms) indicate that the virus capsid or virus vector of the disclosure exhibits tropism for and/or transduces, respectively, tissues throughout the body (e.g., brain, lung, skeletal muscle, heart, liver, kidney and/or pancreas). In embodiments, systemic transduction of the central nervous system (e.g., brain, neuronal cells, etc.) is observed. In other embodiments, systemic transduction of cardiac muscle tissues is achieved.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 125%, 150%, 175%, 200%, 250%, 300%, 350%, 400%, 500% or more of the transduction or tropism, respectively, of the control). In particular embodiments, the virus vector efficiently transduces or has efficient tropism for neuronal cells and cardiomyocytes. Suitable controls will depend on a variety of factors including the desired tropism profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less as compared with the level of transduction of the desired target tissue(s) (e.g., cells of the central nervous system; cardiomyocytes).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), but in representative embodiments are either single or double stranded DNA sequences.

As used herein, an "isolated" polynucleotide (e.g., an "isolated DNA" or an "isolated RNA") means a polynucleotide that is at least partially separated from at least some of the other components of the naturally occurring organism or virus, for example, the cell or viral structural components or other polypeptides or nucleic acids commonly found associated with the polynucleotide. In representative embodiments an "isolated" nucleic acid molecule is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments, an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

As used herein, "neuronal cell" includes sensory neurons, pseudo-unipolar neurons, motor neurons, multipolar neurons, interneurons, and/or bipolar neurons located in brain sub-structures such as the cortex, motor cortex, hippocampus, hypothalamus, striatum, basal ganglia, amygdala, cerebellum, dorsal root ganglia and/or spinal cord.

A "therapeutic protein" is a protein that can alleviate, reduce, prevent, delay and/or stabilize symptoms that result from an absence of or defect in a protein in a cell or subject and/or is a protein that otherwise confers a benefit to a subject.

A "therapeutic RNA molecule" or "functional RNA molecule" as used herein can be an antisense nucleic acid, a ribozyme (e.g., as described in U.S. Pat. No. 5,877,022), an RNA that effects spliceosome-mediated trans-splicing (see, Puttaraju et al. (1999) *Nature Biotech.* 17:246; U.S. Pat. Nos. 6,013,487; 6,083,702), an interfering RNA (RNAi) including siRNA, shRNA or miRNA, which mediate gene silencing (see, Sharp et al., (2000) *Science* 287:2431), and any other non-translated RNA, such as a "guide" RNA (Gorman et al. (1998) *Proc. Nat. Acad. Sci. USA* 95:4929; U.S. Pat. No. 5,869,248 to Yuan et al.) and the like as are known in the art.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the disclosure. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present disclosure.

A "treatment effective" amount as used herein is an amount that is sufficient to provide some improvement or benefit to the subject. Alternatively stated, a "treatment effective" amount is an amount that will provide some alleviation, mitigation, decrease and/or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the disclosure. Those skilled in the art will appreciate that the level of prevention need not be complete, as long as some benefit is provided to the subject.

The terms "heterologous nucleotide sequence" and "heterologous nucleic acid molecule" are used interchangeably herein and refer to a nucleic acid molecule and/or nucleotide sequence that is not naturally occurring in the virus. Generally, the heterologous nucleic acid molecule or nucleotide sequence comprises an open reading frame that encodes a protein or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is a recombinant AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, and/or by stably integrating the sequences into a packaging cell). In embodiments, the rAAV vector genome comprises at least one terminal repeat (TR) sequence (e.g., AAV TR sequence), optionally two TRs (e.g., two AAV TRs), which typically will be at the 5' and 3' ends of the vector genome and flank the heterologous nucleic acid sequence, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, 12 or any other AAV now known or later discovered (see, e.g., Table 1). An AAV terminal repeat need not have the native terminal repeat sequence (e.g., a native AAV TR sequence may be altered by insertion, deletion, substitution, truncation and/or missense mutations), as long as the terminal repeat mediates the desired functions, e.g., replication, virus packaging, integration, and/or provirus rescue, and the like.

The virus vectors of the disclosure can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al. (2000) *Molecular Therapy* 2:619.

The virus vectors of the disclosure can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the disclosure.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 3.

Further, the non-naturally occurring amino acid can be an "unnatural" amino acid as described by Wang et al. *Annu Rev Biophys Biomol Struct.* 35:225-49 (2006)). These unnatural amino acids can advantageously be used to chemically link molecules of interest to the AAV capsid protein.

Modified AAV Capsid Proteins and Virus Capsids and Virus Vectors Comprising the Same.

The present disclosure provides AAV capsid proteins comprising a mutation (i.e., a modification, which can be a substitution or an insertion or a deletion) in the amino acid sequence and virus capsids and virus vectors comprising the modified AAV capsid protein. The mutated AAV capsid proteins, and the nucleic acids encoding them, are not found in nature (i.e., are non-natural) and have neither the sequence of the wild-type sequences found in nature nor the function of those sequences. Rather, the inventors have discovered that modifications at the amino acid positions described herein can confer one or more desirable properties to virus vectors comprising the modified AAV capsid protein including without limitation: (i) selective transduction of neuronal cells after crossing the blood-brain barrier following systemic injection; (ii) simultaneous transduction of cardiac tissue and neuronal tissue following systemic injection; and (iii) detargeting from the liver, spleen, kidney and other peripheral organs.

Figure 7:
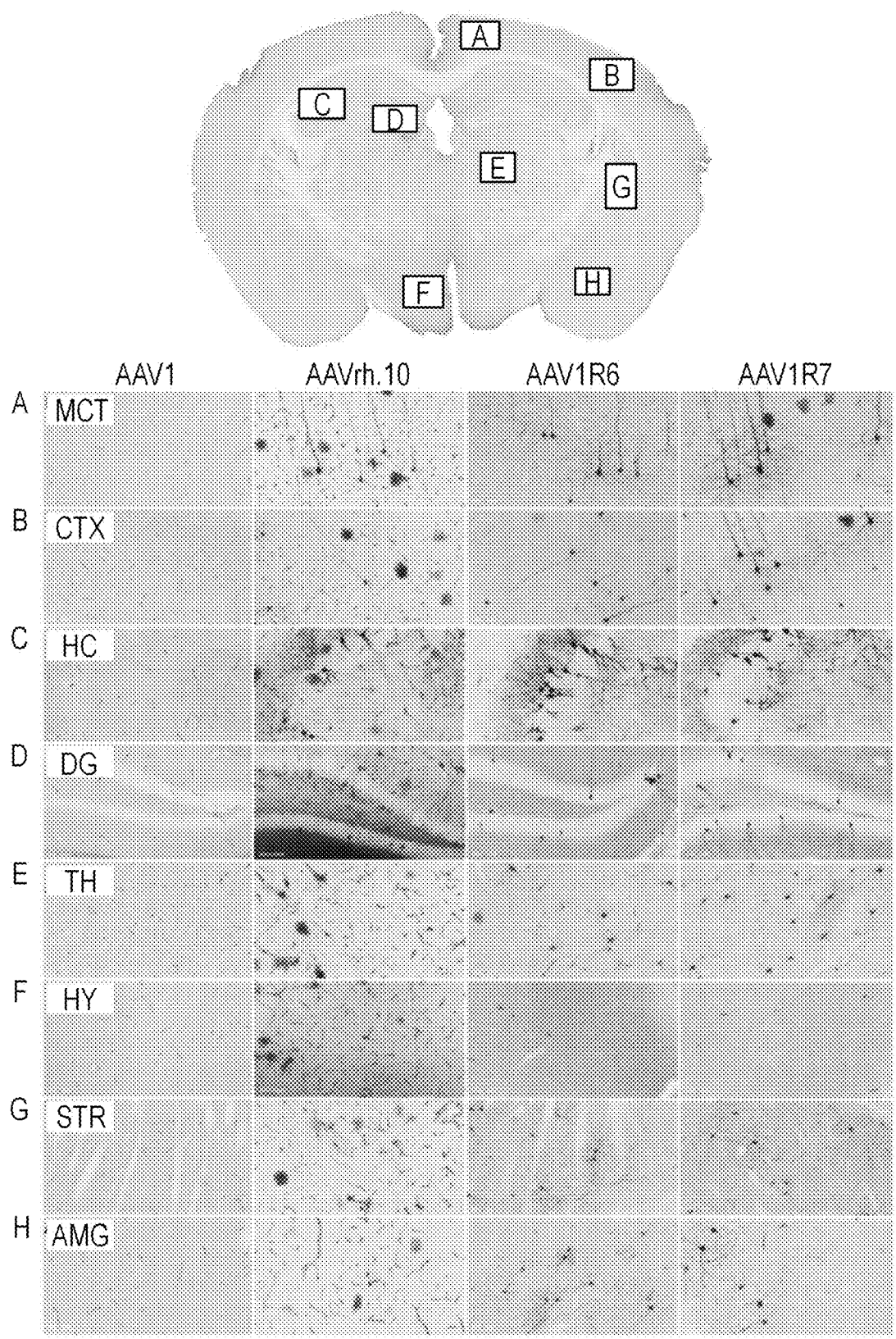
FIGS. 7A-7H. CNS transduction profile of AAV1R6 and AAV1R7 compared to parental AAV1 and AAVrh.10 in the brain. Transduction profiles at three weeks post tail vein injection of AAV vectors packaging a CBh-scGFP transgene at a dose of $5\times10^{11}$ vg for parental serotypes, AAV1 and AAVrh.10 (left columns), and for AAV1R6 and AAV1R7 (right columns) across various brain regions are shown, including the motor cortex (FIG. 7A), cerebral (somatosensory) cortex (FIG. 7B), hippocampus (FIG. 7C), dentate gyrus (FIG. 7D), thalamus (FIG. 7E), hypothalamus (FIG. 7F), striatum (FIG. 7G), and amygdala (FIG. 7H). Scale bar=100 µm.

In particular embodiments, the modified AAV capsid protein of the disclosure comprises one or more mutations (i.e., modifications) in the amino acid sequence of the native AAV1 capsid protein or the corresponding amino acid residue(s) of a capsid protein from another AAV serotype, including but not limited to AAV2, AAV3, AAV6, AAV7, AAV8, AAV9 and AAVrh.10. The amino acid positions in other AAV serotypes or modified AAV capsids that "correspond to" these positions in the native AAV1 capsid protein will be apparent to those skilled in the art and can be readily determined using sequence alignment techniques (see, e.g., FIG. 7 of WO 2006/066066) and/or crystal structure analysis (Padron et al. (2005) J. Virol. 79:5047-58).

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV1, the specific amino acid position(s) may be different than the position in AAV1 (using VP1 numbering. As discussed elsewhere herein, the corresponding amino acid position(s) will be readily apparent to those skilled in the art using well-known techniques.

As used herein, a "mutation" or "modification" in an amino acid sequence includes substitutions, insertions and/or deletions, each of which can involve one, two, three, four, five, six, seven, eight, nine, ten or more amino acids. In particular embodiments, the modification is a substitution. In other embodiments, the modification is an insertion (e.g., of a single amino acid residue between two amino acid residues in an amino acid sequence.)

Thus, in one embodiment, the present disclosure provides an adeno-associated virus (AAV) capsid protein, wherein the AAV capsid protein comprises, consists essentially of or consists of a modification at amino acid residues S262, A263, S264, T265, A267, and S268, and a single amino acid residue insertion between residues 266 and 267 (VP1 numbering), wherein the numbering of each residue is based on the amino acid sequence of AAV1 (SEQ ID NO:1) or the equivalent amino acid residue in AAV2 (SEQ ID NO:2), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the AAV capsid protein may comprise a modification at amino acid residue H272. In particular embodiments, the modification is S262N, A263G, S264T, T265S, A267S, S268T, H272T, and combinations thereof. In particular embodiments, the single amino acid residue insertion between residues 266 and 267 is G (designated -267G).

In some embodiments, the AAV capsid protein described above can further comprise, consist essentially of or consist of a modification at amino acid residues Q148, E152, S157, T162, H272, T326, D328, V330, T331, V341 and S345, and a single amino acid residue insertion between residues 152 and 153 (VP1 numbering), wherein the numbering of each residue is based on the amino acid sequence of SEQ ID NO:1 or the equivalent amino acid residue in SEQ ID NOs:2, 3, 4, 5, 6, 7 or 8. In particular embodiments, the modification is Q148P, E152R, S157T, T162K, H272T, T326Q, D328E, V330T, T331K, V341I and S345T. In particular embodiments, the single amino acid residue insertion between residues 152 and 153 is S (designated -153S).

In some embodiments, the AAV capsid protein described above can further comprise, consist essentially of or consist of a modification of amino acid residues L188, S205, N223, A224, and H272 (VP1 numbering), wherein the numbering of each residue is based on the amino acid sequence of SEQ ID NO:1 or the equivalent amino acid residue in SEQ ID NOs:2, 3, 4, 5, 6, 7 or 8. In particular embodiments, the modification is L188I, S205A, N223S, A224S, and H272T.

In some embodiments, the disclosure provides an adeno-associated virus (AAV) capsid protein, wherein the AAV capsid protein comprises, consists essentially of, or consists of a modification at amino acid residues S262, A263, S264, T265, and A267 (VP1 numbering), and a single amino acid residue insertion between residues S268 and N269, wherein the numbering of each residue is based on the amino acid sequence of AAV1 (SEQ ID NO:1) or the equivalent amino acid residue in AAV2 (SEQ ID NO:2), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the modification is at least one of S262N, A263G, S264T, T265S, and A267S. In some embodiments, the AAV capsid can further comprise, consist essentially of, or consist of a modification at amino acid residue H272. In some embodiments, the AAV capsid protein can further comprise, consist essentially of, or consist of a modification at amino acid residues Q148, E152, S157, T162, H272, T326, D328, V330, T331, V341 and S345, and a single amino acid residue insertion between residues E152 and P153. In some embodiments, the AAV capsid protein further comprises a modification at amino acid residues L188, S205, N223, A224, and H272. In some embodiments, the modification is at least one of L188I, S205A, N223S, A224S and H272T. In some embodiments, the amino acid residue insertion between residues S268 and N269 is an insertion of a single T residue. In some embodiments, the amino acid residue insertion between residues E152 and P153 is an insertion of a single S residue.

In some embodiments, the disclosure provides an adeno-associated virus (AAV) capsid protein, wherein the AAV capsid protein comprises, consists of, or consists essentially of a modification resulting in the amino acid sequence: $X^1$-$X^2$-$X^3$-$X^4$ (SEQ ID NO:35) at the amino acids corresponding to amino acid positions 262 to 265 (VP1 numbering) of the native AAV1 capsid protein (SEQ ID NO:1), wherein $X^1$ is any amino acid other than S; wherein $X^2$ is any amino acid other than A; wherein $X^3$ is any amino acid other than S; and wherein $X^4$ is any amino acid other than T. 45. In some embodiments, the amino acid $X^1$ is N, the amino acid $X^2$ is G, the amino acid $X^3$ is T, or the amino acid $X^4$ is S. In some embodiments, the amino acid $X^1$ is N, the amino acid $X^2$ is G, the amino acid $X^3$ is T, and the amino acid X⁴ is S. In some embodiments, the AAV capsid protein further comprises a modification at amino acid residue H272. In some embodiments, the modification is H272T. In some embodiments, the AAV capsid protein further comprises an amino acid residue insertion between amino acid residues S268 and N269. In some embodiments, the amino acid residue insertion is an insertion of a single T residue.

In some embodiments, the disclosure provides an adeno-associated virus (AAV) capsid protein, wherein the AAV capsid protein comprises, consists essentially of, or consists of a modification at amino acid residues S262, A263, S264, T265, A267, and H272, and a single amino acid residue insertion between residues S268 and N269, (VP1 numbering), wherein the numbering of each residue is based on the amino acid sequence of AAV1 (SEQ ID NO:2) or the equivalent amino acid residue in AAV1 (SEQ ID NO:1), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the modification comprises at least one of S262N, A263G, S264T, T265S, A267G, and H272T. In some embodiments, the natural single amino acid residue insertion between residues S268 and N269 is an insertion of a single T residue.

In some embodiments, the disclosure provides an adeno-associated virus (AAV) capsid protein, wherein the AAV capsid protein comprises, consists essentially of, or consists of a modification at amino acid residues S262, Q263, S264, A266, S267, and H271, and an insertion of at least one amino acid residue between residues S261 and S262, (VP1 numbering), wherein the numbering of each residue is based on the amino acid sequence of AAV2 (SEQ ID NO:2) or the equivalent amino acid residue in AAV1 (SEQ ID NO:1), AAV3 (SEQ ID NO:3), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the modification comprises at least one of S262T, Q263S, S264G, A266S, S267T, and H271T. In some embodiments, the insertion between residues SS61 and S262 is an insertion of a single amino acid residue. In some embodiments, the insertion between residues S251 and S252 is an insertion more than one amino acid residue. In some embodiments, the insertion between residues S251 and S252 is an insertion of an N and a G residue.

In some embodiments, the disclosure provides an adeno-associated virus (AAV) capsid protein, wherein the AAV capsid protein comprises, consists essentially of, or consists of a modification at amino acid residues S262, Q263, S264, A266, A267, H271, and a single amino acid residue insertion between residues S261 and S262, wherein the numbering of each residue is based on the amino acid sequence of AAV3 (SEQ ID NO:3) or the equivalent amino acid residue in AAV1 (SEQ ID NO:1), AAV2 (SEQ ID NO:2), AAV6 (SEQ ID NO:4), AAV7 (SEQ ID NO:5), AAV8 (SEQ ID NO:6), AAV9 (SEQ ID NO:7) or AAVrh10 (SEQ ID NO:8). In some embodiments, the modification comprises at least one of S262T, Q263S, S264G, A266S, A267T, H271T. In some embodiments, the insertion between residues SS61 and S262 is an insertion of a single amino acid residue, or more than one amino acid residue. In some embodiments, the insertion between residues S251 and S252 is an insertion of an N and a G residue.

In some embodiments, the disclosure provides an adeno-associated virus (AAV) capsid protein, wherein the AAV capsid protein comprises, consists essentially of, or consists of a modification at amino acid residues S263, S269, A237 (VP1 numbering), wherein the numbering of each residue is based on the amino acid sequence of AAV9 (SEQ ID NO:9) or the equivalent amino acid residue in AAV1 (SEQ ID NO:1), AAV2 (SEQ ID NO:2), AAV3 (SEQ ID NO:3), AAV6 (SEQ ID NO:4), AAV7 (SEQ ID NO:5), AAV8 (SEQ ID NO:6), or AAVrh10 (SEQ ID NO:8). In some embodiments, the modification comprises at least one of S263G, S269T, and A273T.

In some embodiments, the disclosure provides an adeno-associated virus (AAV) capsid protein, wherein the AAV capsid protein comprises, consists essentially of, or consists of the sequence of any one of SEQ ID NO:9 to SEQ ID NO:34.

Nonlimiting examples of modifications to produce the capsid proteins of this disclosure in AAV serotypes 1, 2, 3, 6, 7, 8, and 9, respectively, are shown in Table 2, wherein the equivalent amino acid residues in the respective AAV serotypes are identified.

In further embodiments, the capsid proteins of this disclosure can comprise, consist essentially of or consist of: the amino acid sequence of SEQ ID NO:9 (AAV1RX); the amino acid sequence of SEQ ID NO:10 (AAV2RX); the amino acid sequence of SEQ ID NO:11 (AAV3RX); the amino acid sequence of SEQ ID NO:12 (AAV6RX); the amino acid sequence of SEQ ID NO:13 (AAV7RX); the amino acid sequence of SEQ ID NO:14 (AAV8RX); the amino acid sequence of SEQ ID NO:15 (AAV9RX); the amino acid sequence of SEQ ID NO: 16 (AAV1R6); the amino acid sequence of SEQ ID NO:17 (AAV2R6); the amino acid sequence of SEQ ID NO:18 (AAV3R6); the amino acid sequence of SEQ ID NO:19 (AAV6R6); the amino acid sequence of SEQ ID NO:20 (AAV7R6); the amino acid sequence of SEQ ID NO:21 (AAV8R6); the amino acid sequence of SEQ ID NO:22 (AAV9R6); the amino acid sequence of SEQ ID NO:23 (AAV1R7); the amino acid sequence of SEQ ID NO:24 (AAV2R7); the amino acid sequence of SEQ ID NO:25 (AAV3R7); the amino acid sequence of SEQ ID NO:26 (AAV6R7); the amino acid sequence of SEQ ID NO:27 (AAV7R7); the amino acid sequence of SEQ ID NO:28 (AAV8R7); and the amino acid sequence of SEQ ID NO:29 (AAV9R7). In one embodiment, a capsid protein of this disclosure has the amino acid sequence of SEQ ID NO:9 (AAV1RX). In one embodiment, a capsid protein of this disclosure has the amino acid sequence of SEQ ID NO:16 (AAV1R6). In one embodiment, a capsid protein of this disclosure has the amino acid sequence of SEQ ID NO:23 (AAV1R7).

In some embodiments, the present disclosure provides AAV capsid proteins having at least 80%, at least 85%, at least 90%, at least 95%, at least 99%, inclusive of all ranges and subranges therebetween, sequence identity to the amino acid sequence of SEQ ID NO:9 (AAV1RX); the amino acid sequence of SEQ ID NO:10 (AAV2RX); the amino acid sequence of SEQ ID NO:11 (AAV3RX); the amino acid sequence of SEQ ID NO:12 (AAV6RX); the amino acid sequence of SEQ ID NO:13 (AAV7RX); the amino acid sequence of SEQ ID NO:14 (AAV8RX); and the amino acid sequence of SEQ ID NO:15 (AAV9RX).

In some embodiments, the present disclosure provides AAV capsid proteins having at least 80%, at least 85%, at least 90%, at least 95%, at least 99%, inclusive of all ranges and subranges therebetween, sequence identity to the amino acid sequence of SEQ ID NO: 16 (AAV1R6); the amino acid sequence of SEQ ID NO:17 (AAV2R6); the amino acid sequence of SEQ ID NO:18 (AAV3R6); the amino acid sequence of SEQ ID NO:19 (AAV6R6); the amino acid sequence of SEQ ID NO:20 (AAV7R6); the amino acid sequence of SEQ ID NO:21 (AAV8R6); the amino acid sequence of SEQ ID NO:22 (AAV9R6).

In some embodiments, the present disclosure provides AAV capsid protein having at least 80%, at least 85%, at least 90%, at least 95%, at least 99%, inclusive of all ranges and subranges therebetween, sequence identity to the amino acid sequence of the amino acid sequence of SEQ ID NO:23 (AAV1R7); the amino acid sequence of SEQ ID NO:24 (AAV2R7); the amino acid sequence of SEQ ID NO:25 (AAV3R7); the amino acid sequence of SEQ ID NO:26 (AAV6R7); the amino acid sequence of SEQ ID NO:27 (AAV7R7); the amino acid sequence of SEQ ID NO:28 (AAV8R7); and the amino acid sequence of SEQ ID NO:29 (AAV9R7).

The present disclosure also provides an adeno-associated virus (AAV) capsid protein, wherein the AAV capsid protein comprises one or more substitution at all positions or in any combination of fewer than all positions, resulting in the amino acid sequence: $X^1$-$X^2$-$X^3$-$X^4$ (SEQ ID NO:35). In some embodiments, the modification of the amino acid sequence: $X^1$-$X^2$-$X^3$-$X^4$ is at the amino acids corresponding to amino acid positions 262 to 265 (VP1 numbering) of the native AAV1 capsid protein (SEQ ID NO:1). In some embodiments, $X^1$ can be any amino acid other than S. In some embodiments, $X^2$ can be any amino acid other than A. In some embodiments, $X^3$ can be any amino acid other than S. In some embodiments, $X^4$ can be any amino acid other than T. In one embodiment, the amino acid $X^1$ is N. In one embodiment, the amino acid $X^2$ is G. In one embodiment, the amino acid $X^3$ is T. In one embodiment, the amino acid $X^4$ is S. In another embodiment, $X^1$ is N, $X^2$ is G, $X^3$— is T, and $X^4$ is S. In some embodiments, one of $X^1$ through $X^4$ is not substituted, and the amino acid residue at the unsubstituted position is the wild type amino acid residue.

Examples of amino acid residues that can be substituted for the native amino acid at the respective positions described herein are set forth in Table 3.

It is to be understood that the substitutions and insertions described in the AAV capsid proteins of this disclosure can include substitutions and/or insertions with conservative amino acid residues. Such conservative substitutions are well known in the art and include, e.g., nonpolar amino acids Gly, Ala, Val, Leu, Ile, Met, Phe, Trp and Pro can be substituted for one another; polar amino acids Ser, Thr, Cys, Tyr, Asn and Gln can be substituted for one another; negatively charged amino acids Asp and Glu can be substituted for one another; and positively charged amino acids Lys, Arg and His can be substituted for one another, in any combination.

The present disclosure also provides an AAV capsid comprising a capsid protein of this disclosure as well as a virus vector comprising an AAV capsid of this disclosure. In some embodiments, the virus vector can comprise, consist essentially of or consist of a virus vector comprising: an AAV capsid of this disclosure; and a nucleic acid molecule comprising at least one terminal repeat sequence, wherein the nucleic acid is encapsidated by the AAV capsid. In some embodiments, the terminal repeat is an AAV terminal repeat. In some embodiments, the terminal repeat is a non-AAV terminal repeat.

Also provided herein is a composition comprising the capsid protein and/or virus vector of this disclosure in a pharmaceutically acceptable carrier.

Several methods are provided in this disclosure as well, including a method of introducing a nucleic acid molecule into a cell, comprising contacting the cell with the virus vector of and/or composition of this disclosure, e.g., under conditions whereby the virus vector is taken into or internalized by the cell and a nucleic acid molecule introduced via the virus vector is expressed in the cell.

Also provided herein is a method of delivering a nucleic acid molecule to a subject, comprising administering to the subject the virus vector and/or the composition of this disclosure. In particular embodiments, the virus vector and/or composition are administered to the central nervous system of the subject. In particular embodiments, the virus vector and/or composition is delivered across the blood brain barrier.

In some embodiments, the virus vector of this disclosure can comprise a nucleic acid molecule of interest. In some embodiments, the nucleic acid molecule of interest can encode a therapeutic protein or therapeutic RNA molecule.

The present disclosure also provides a method of selectively delivering a nucleic acid molecule of interest to a neuronal cell, comprising contacting the neuronal cell with the virus vector of this disclosure, wherein the virus vector comprises the nucleic acid molecule of interest. In further embodiments, the method can additionally comprise selectively delivering a nucleic acid molecule of interest to a cardiomyocyte, e.g., when the method is carried out in a subject (e.g., a human subject). In some embodiments, the composition is selectively delivered to a neuronal cell. In some embodiments, the composition is selectively delivered to a cardiomyocyte.

In additional embodiments, the present disclosure provides a method of treating a neurological disorder or defect in a subject, comprising administering to the subject the virus vector of this disclosure, wherein the virus vector comprises a nucleic acid molecule that encodes a therapeutic protein or therapeutic RNA effective in treating the neurological disorder or defect.

Additionally provided herein is a method of treating a neurological and cardiovascular disorder or defect in a subject, comprising administering to the subject the virus vector of this disclosure, wherein the virus vector comprises a nucleic acid molecule that encodes a therapeutic protein or therapeutic RNA effective in treating the neurological and cardiological disorder or defect.

In the methods described herein, the virus vector and/or composition of this disclosure can be administered/delivered to a subject of this disclosure via a systemic route (e.g., intravenously, intraarterially, intraperitoneally, etc.). In some embodiments, the virus vector and/or composition can be administered to the subject via an intracerebroventrical, intracisternal, intraparenchymal, intracranial and/or intrathecal route.

In some embodiments, the systemic administration of the virus vector and/or composition to the subject results in lower transduction in off-target tissues (e.g., other than the central nervous system). In some embodiments of this disclosure, the virus vector is detargeted from the spleen, the liver, and/or the kidney. In some embodiments, the virus vector is detargeted from splenocytes, hepatocytes and/or kidney cells. In some embodiments, the virus vector transduces the liver, spleen, and/or kidney at a level that is reduced by at least 10%, 20%, 30%, 40%, 50%, 60%, 70%, 75%, 80%, 85%, 90%, 95%, 96%, 97%, 98%, 99% or 100% compared to transduction by AAVrh.10, wherein viral transduction is optionally determined by luciferase or GFP expression. Preferably, the virus vector transduces the liver, spleen, and/or kidney at a level that reduced by at least 50%-100%, or 80-90% compared to transduction by AAVrh.10, wherein viral transduction is optionally determined by luciferase or GFP expression.

In some embodiments, the virus vector transduces the brain at a level that is increased by at least 10%, 20%, 30%, 40%, 50%, 60%, 70%, 75%, 80%, 85%, 90%, 95%, 96%, 97%, 98%, 99% or 100% compared to transduction by AAV1, wherein viral transduction is optionally determined by luciferase or GFP expression. Preferably, the virus vector transduces brain at a level that is increased by at least 2-fold, 2.5-fold, 3-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold compared to transduction by AAV1, wherein viral transduction is optionally determined by luciferase or GFP expression. In some embodiments, the virus vector selectively transduces neurons.

The disclosure contemplates that the modified capsid proteins of the disclosure can be produced by modifying the capsid protein of any AAV now known or later discovered. Further, the AAV capsid protein that is to be modified can be a naturally occurring AAV capsid protein (e.g., an AAV2, AAV3a or 3b, AAV6, AAV7, AAV8, AAV9, AAVrh.10 or any of the AAV serotypes shown in Table 1), but is not so limited. Those skilled in the art will understand that a variety of manipulations to the AAV capsid proteins are known in the art and the disclosure is not limited to modifications of naturally occurring AAV capsid proteins. For example, the capsid protein to be modified may already have modifications as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11 and/or AAV12 or any other AAV now known or later discovered). Such AAV capsid proteins are also within the scope of the present disclosure.

Thus, in particular embodiments, the AAV capsid protein to be modified can be derived from a naturally occurring AAV but can further comprise one or more foreign sequences (e.g., that are exogenous to the native virus) that are inserted and/or substituted into the capsid protein and/or have been altered by deletion of one or more amino acids.

Accordingly, when referring herein to a specific AAV capsid protein (e.g., an AAV1, AAV2, AAV3, AAV4, AAV5, AAV6, AAV7, AAV8, AAV9, AAV10, AAV11 or AAV12 capsid protein or a capsid protein from any of the AAV serotypes shown in Table 1, etc.), it is intended to encompass the native capsid protein as well as capsid proteins that have alterations other than the modifications of the disclosure. Such alterations include substitutions, insertions and/or deletions. In particular embodiments, the capsid protein can comprise 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present disclosure) as compared with the native AAV capsid protein sequence. In embodiments of the disclosure, the capsid protein can comprise 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments, the capsid protein can comprise a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the disclosure) as compared with the native AAV capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence.

For example, in particular embodiments, an AAV1, AAV2, AAV3, AAV4, AAV5, AAV6, AAV7, AAV8, AAV9, AAV10, AAV11, AAV12, etc. capsid protein encompasses the native AAV1, AAV2, AAV3, AAV4, AAV5, AAV6, AAV7, AAV8, AAV9, AAV10, AAV11, AAV12 capsid protein sequence as well as sequences that are at least about 80%, 85%, 90%, 95%, 97%, 98% or 99% similar or identical to the native AAV1, AAV2, AAV3, AAV4, AAV5, AAV6, AAV7, AAV8, AAV9, AAV10, AAV11, AAV12 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith and Waterman, *Adv. Appl. Math.* 2, 482 (1981), by the sequence identity alignment algorithm of Needleman and Wunsch *J. Mol. Biol.* 48,443 (1970), by the search for similarity method of Pearson and Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al. *Nucl. Acid Res.* 12, 387-395 (1984), or by inspection.

Another suitable algorithm is the BLAST algorithm, described in Altschul et al. J. *Mol. Biol.* 215, 403-410, (1990) and Karlin et al. *Proc. Natl. Acad. Sci. USA* 90, 5873-5787 (1993). A particularly useful BLAST program is the WU-BLAST-2 program which was obtained from Altschul et al. *Methods in Enzymology,* 266, 460-480 (1996); http://blast.wustl/edu/blast/README.html. WU-BLAST-2 uses several search parameters, which are optionally set to the default values.

Further, an additional useful algorithm is gapped BLAST as reported by Altschul et al., (1997) *Nucleic Acids Res.* 25, 3389-3402.

The modified virus capsids can be used as "capsid vehicles," as have been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the disclosure, the therapeutically useful molecule is covalently linked (i.e., conjugated or chemically coupled) to the capsid proteins. Methods of covalently linking molecules are known by those skilled in the art.

The modified virus capsids of the disclosure also find use as templates for further modification of antigenicity to evade neutralizing antibodies in any mammalian serum, as described, e.g., in PCT Application Serial No. PCT/2016/054143.

The modified virus capsids of the disclosure also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid molecule encoding a polypeptide, peptide and/or functional RNA of interest. For example, the inventive capsids can be delivered to block cellular receptors on particular cells and a delivery vector can be administered subsequently or concurrently, which may reduce transduction of the blocked cells, and enhance transduction of other targets.

According to representative embodiments, modified virus capsids can be administered to a subject prior to and/or concurrently with a modified virus vector according to the present disclosure. Further, the disclosure provides compositions and pharmaceutical formulations comprising the inventive modified virus capsids; optionally, the composition also comprises a modified virus vector of the disclosure.

The disclosure also provides nucleic acid molecules (optionally, isolated nucleic acid molecules) encoding the modified virus capsids and capsid proteins of the disclosure. Further provided are vectors comprising the nucleic acid molecules and cells (in vivo or in culture) comprising the nucleic acid molecules and/or vectors of the disclosure. Suitable vectors include without limitation viral vectors (e.g., adenovirus, AAV, herpesvirus, alphavirus, vaccinia, poxviruses, baculoviruses, and the like), plasmids, phage, YACs, BACs, and the like. Such nucleic acid molecules, vectors and cells can be used, for example, as reagents (e.g., helper packaging constructs or packaging cells) for the production of modified virus capsids or virus vectors as described herein.

Virus capsids according to the disclosure can be produced using any method known in the art, e.g., by expression from a baculovirus (Brown et al. (1994) *Virology* 198:477-488).

The modifications to the AAV capsid protein according to the present disclosure are "selective" modifications. This approach is in contrast to previous work with whole subunit or large domain swaps between AAV serotypes (see, e.g., international patent publication WO 00/28004; Hauck et al. (2003) *J. Virology* 77:2768-2774; Shen et al. (2007) *Mol Ther.* 15(11):1955-62; and Mays et al. (2013) *J. Virol.* 87(17):9473-85). The AAV capsid proteins of this disclosure are, to the inventors' knowledge, the first examples of specific amino acid changes to enable crossing the blood brain barrier.

In some embodiments, an AAV capsid protein contains specific amino acid changes that enable crossing the blood brain barrier. In some embodiments, the AAV capsid protein comprises substitutions of 8, 9, 10, 11, 12, 13, 14, 15, 16, 17, 18, 19, 20, 21, or 22 amino acids, wherein the substituted amino acids are derived from AAVrh.10, wherein the amino acid substitutions enable crossing the blood brain barrier. In some embodiments, the AAV capsid protein is derived from an AAV1 capsid protein, and comprises substitutions of 8, 9, 10, 11, 12, 13, 14, 15, 16, 17, 18, 19, 20, 21, or 22 amino acids, wherein the substituted amino acids are derived from AAVrh.10, wherein the amino acid substitutions enable crossing the blood brain barrier. In some embodiments, the specific amino acids that enable crossing the blood brain barrier are 262N, 263G, 264T, 265S, 267G, 268S, 269T and 273T (VP1 numbering), wherein the numbering of each residue is based on the amino acid sequence of SEQ ID NO:9 or SEQ ID NO:30.

In some embodiments, an AAV capsid protein contains specific amino acid changes that enable detargeting from the liver, kidney, and/or spleen. In some embodiments, the AAV capsid protein comprises substitutions of 8, 9, 10, 11, 12, 13, 14, 15, 16, 17, 18, 19, 20, 21, or 22 amino acids, wherein the substituted amino acids are derived from AAVrh.10, wherein the amino acid substitutions enable detargeting from the liver, kidney, and/or spleen. In some embodiments, the AAV capsid protein is derived from an AAV1 capsid protein, and comprises 8, 9, 10, 11, 12, 13, 14, 15, 16, 17, 18, 19, 20, 21, or 22 amino acids, wherein the substituted amino acids are derived from AAVrh.10, wherein the amino acid substitutions enable detargeting from the liver, kidney, and/or spleen.

In some embodiments, the substituted amino acids are located in the VR-I region of the capsid. In some embodiments, the substituted amino acids are located on the surface of the capsid. In some embodiments, the substituted amino acids are located at the base of the protrusions at a 3-fold axis of symmetry of the capsid. In some embodiments, the substituted amino acids are located in the depression at a 2-fold axis of symmetry of the capsid. In some embodiments, the substituted amino acids are located within the VR-II region of the capsid protein, within the DE-loop. In some embodiments, the substituted amino acids are located within beta-strand E of the capsid.

In particular embodiments, a "selective" modification results in the insertion and/or substitution and/or deletion of less than about 20, 18, 15, 12, 10, 9, 8, 7, 6, 5, 4, 3 or 2 contiguous amino acids.

The modified capsid proteins and capsids of the disclosure can further comprise any other modification, now known or later identified.

For example, the AAV capsid proteins and virus capsids of the disclosure can be chimeric in that they can comprise all or a portion of a capsid subunit from another virus, optionally another parvovirus or other AAV serotype, e.g., as described in international patent publication WO 00/28004.

The virus capsid can comprise a targeting sequence (e.g., substituted and/or inserted in the viral capsid) that directs the virus capsid to interact with cell-surface molecules present on a desired target tissue(s) (see, e.g., International patent publication WO 00/28004 and Hauck et al. (2003) *J. Virology* 77:2768-2774); Shi et al. *Human Gene Therapy* 17:353-361 (2006) [describing insertion of the integrin receptor binding motif RGD at positions 520 and/or 584 of the AAV capsid subunit]; U.S. Pat. No. 7,314,912 [describing insertion of the P1 peptide containing an RGD motif following amino acid positions 447, 534, 573 and 587 of the AAV2 capsid subunit] and International Patent Publication No. WO 2015038958 [describing selective recovery of AAV vectors containing peptide sequences showing increased CNS transduction]). Other positions within the AAV capsid subunit that tolerate insertions are known in the art (e.g., positions 449 and 588 described by Grifman et al. *Molecular Therapy* 3:964-975 (2001)).

For example, some of the virus capsids of the disclosure have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described by Wang et al. (*Annu Rev Biophys Biomol Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques*, 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind heparan sulfate (HS) receptors (e.g., AAV 4, AAV5) to confer heparin binding to the resulting mutant.

As another nonlimiting example, amino acid footprints that can enable binding to glycans such as galactose, sialic acid, mannose, lactose, sulfo-N-lactosamine, galactosamine, glucose, glucosamine, fructose, fucose, gangliosides, chitotriose, chondroitin sulfate, keratin sulfate, dermatan sulfate may be grafted onto a capsid subunit that does not typically bind one or more of the sugars listed above [e.g., US Patent Publication No. US20160017005, entitled Methods and compositions for dual glycan binding AAV vectors].

B19 infects primary erythroid progenitor cells using globoside as its receptor (Brown et al. (1993) *Science* 262:114). The structure of B19 has been determined to 8 Å resolution (Agbandje-McKenna et al. (1994) *Virology* 203:106). The region of the B19 capsid that binds to globoside has been mapped between amino acids 399-406 (Chapman et al. (1993) *Virology* 194:419), a looped out region between β-barrel structures E and F (Chipman et al. (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties, polysialic acid moieties, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

As yet a further alternative, the targeting sequence may be a peptide that can be used for chemical coupling (e.g., can comprise arginine and/or lysine residues that can be chemically coupled through their R groups) to another molecule that targets entry into a cell.

The modifications described above can be incorporated into the capsid proteins or capsids of the disclosure in combination with each other and/or with any other modification now known or later discovered.

The disclosure also encompasses virus vectors comprising the modified capsid proteins and capsids of the disclosure. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the disclosure and a vector genome.

For example, in representative embodiments, the virus vector comprises: (a) a modified virus capsid (e.g., a modified AAV capsid) comprising a modified capsid protein of the disclosure; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid molecule encoding a protein or functional RNA of interest. Recombinant virus vectors are described in more detail below.

It will be understood by those skilled in the art that the modified capsid proteins, virus capsids and virus vectors of the disclosure exclude those capsid proteins, capsids and virus vectors that have the indicated amino acids at the specified positions in their native state (i.e., are not mutants).

Methods of Producing Virus Vectors

The present disclosure further provides methods of producing the inventive virus vectors. In one representative embodiment, the present disclosure provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the disclosure). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski (1992) Curr. Top. Microbiol. Immun. 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector.

In particular embodiments, the nucleic acid template is supplied by a herpesvirus or adenovirus vector (e.g., inserted into the E1a or E3 regions of a deleted adenovirus). As another illustration, Palombo et al. (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al. ((2001) Gene Ther. 18:704-12) describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) Gene Therapy 6:986 and WO 00/17377.

As a further alternative, the virus vectors of the disclosure can be produced in insect cells using baculovirus vectors to deliver the rep/cap genes and rAAV template as described, for example, by Urabe et al. (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity chromatography [e.g., for a heparin substrate (Zolotukhin et al. (1999) *Gene Therapy* 6:973) or using affinity resin (Wang et al., (2015), *Mol Ther Methods C/in Dev* 2:15040) or for e.g., other methods (reviewed in Qu et al. (2015) *Curr Pharm Biotechnol.* 16(8):684-95)]. Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The virus vectors of the present disclosure are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present disclosure. Nucleic acids of interest include nucleic acids encoding polypeptides, including therapeutic (e.g., for medical or veterinary uses) or immunogenic (e.g., for vaccines) proteins and/or functional or therapeutic RNA molecules.

Therapeutic polypeptides include, but are not limited to, cystic fibrosis transmembrane regulator protein (CFTR), dystrophin (including mini- and micro-dystrophins, see, e.g., Vincent et al. (1993) *Nature Genetics* 5:130; U.S. Patent Publication No. 2003/017131; International publication WO/2008/088895, Wang et al. *Proc. Natl. Acad. Sci. USA* 97:13714-13719 (2000); and Gregorevic et al. *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al. (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factorα soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, green fluorescent protein (GFP), β-galactosidase, alkaline phosphatase, luciferase, and chloramphenicol acetyltransferase gene.

Optionally, the heterologous nucleic acid molecule can encode a secreted polypeptide (e.g., a polypeptide that is a secreted polypeptide in its native state or that has been engineered to be secreted, for example, by operable association with a secretory signal sequence as is known in the art).

Alternatively, in particular embodiments of this disclosure, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al. (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al. (2000) *Science* 287:2431), and other non-translated RNAs, such as "guide" RNAs (Gorman et al. (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al. *J Gene Med.* 10:132-142 (2008) and Li et al. *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the disclosure.

The virus vector may also comprise a heterologous nucleic acid molecule that shares homology with and recombines with a locus on a host chromosome. This approach can be utilized, for example, to correct a genetic defect in the host cell.

The present disclosure also provides virus vectors that express an immunogenic polypeptide, e.g., for vaccination. The nucleic acid molecule may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) *Proc. Natl. Acad. Sci. USA* 91:3515; Kawakami et al., (1994) *J. Exp. Med.,* 180:347; Kawakami et al. (1994) *Cancer Res.* 54:3124), MART-1, gp100 MAGE-1, MAGE-2, MAGE-3, CEA, TRP-1, TRP-2, β-15, tyrosinase (Brichard et al. (1993) *J Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

In additional embodiments, the heterologous nucleic acid can encode (a) a site-directed modifying polypeptide based on zinc finger nucleases or meganucleases or endonucleases or TALENs or CRISPR/Cas system based nucleases that contain an RNA-binding portion that interacts with a DNA-targeting RNA molecule (gRNA), or an mRNA encoding such polypeptide; (b) one or more guide RNA molecules (gRNAs) comprising a nucleotide sequence that is complementary to a sequence in a target DNA, and a second segment that interacts with a site-directed modifying polypeptide; and/or (c) one or more DNA donor template molecules comprising a single or double stranded DNA sequence designed for homologous recombination into the target site of a mammalian genome. For example, the virus vectors may be introduced into stem cells and/or T lymphocytes ex vivo, cultured cells, tissues and/or whole organisms in vivo and the expressed gene product enables editing, disruption, transcriptional activation and/or repression of target genes in the host.

It will be understood by those skilled in the art that the heterologous nucleic acid molecule(s) of interest can be operably associated with appropriate control sequences. For example, the heterologous nucleic acid molecule can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid molecule(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element can be a mammalian promoter/enhancer element. The promoter/enhancer element can be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present disclosure provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present disclosure can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (B-globin), anemia (erythropoietin) and other blood disorders, Alzheimer's disease (GDF; neprilysin), multiple sclerosis (B-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knock-down such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), spinal muscular atrophy (SMA), Batten's disease, spinal cerebral ataxias including Friedreich's ataxia, SCAT, SCA2 and SCA3, phenylketonuria (phenylalanine hydroxylase), autoimmune diseases, and the like. The disclosure can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BMP 2, 7, etc., RANKL and/or VEGF) can be administered with a bone allograft, for example, following a break or surgical removal in a cancer patient.

The disclosure can also be used to produce induced pluripotent stem cells (iPS). For example, a virus vector of the disclosure can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The disclosure can also be practiced to treat and/or prevent epilepsy, stroke, traumatic brain injury, cognitive disorders, behavioral disorders, psychiatric disorders, Huntington's disease, Alzheimer's disease, amyotrophic lateral sclerosis (ALS), as well as any other neurodegenerative condition that might benefit from or require axonal/neuronal regeneration or repair.

In particular embodiments, the present disclosure can be practiced to promote axonal regeneration and neuronal repair, restore circuits and/or replenish lost neurons as a corrective therapy, e.g., by targeted regulation or overexpression of stem cell differentiation and reprogramming factors such as FoxJ1, Fox2, NeuroD2, NG2 or Olig2 and/or microRNAs such as miR-137, MiR124, as well as any other factors or miRNAs implicated in neuronal development and differentiation.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present disclosure permit the treatment and/or prevention of genetic diseases.

The virus vectors according to the present disclosure may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant disclosure find use in diagnostic and screening methods, whereby a nucleic acid of interest is transiently or stably expressed in a cell culture system, or alternatively, a transgenic animal model.

The virus vectors of the present disclosure can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present disclosure may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present disclosure can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the disclosure provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant disclosure. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-la, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present disclosure find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the disclosure.

In particular embodiments, the present disclosure provides a pharmaceutical composition comprising a virus vector and/or capsid of the disclosure in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present disclosure is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about 10 infectious units, optionally at least about 105 infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about 102 to about $10^8$ cells or at least about 103 to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the disclosure is a method of administering the virus vector and/or virus capsid to subjects. Administration of the virus vectors and/or capsids according to the present disclosure to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the disclosure can further be administered to elicit an immunogenic response (e.g., as a vaccine). Typically, immunogenic compositions of the present disclosure comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular, intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). In some embodiments, intramuscular includes administration to skeletal, diaphragm and/or cardiac muscle. Administration can also be to a tumor (e.g., in or near a tumor or a lymph node). The most suitable route in any given case will depend on the nature and severity of the condition being treated and/or prevented and on the nature of the particular vector that is being used.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present disclosure is administered to skeletal muscle, diaphragm muscle and/or cardiac muscle (e.g., to treat and/or prevent muscular dystrophy, heart disease). In some embodiments, a virus vector and/or virus capsid according to the present disclosure is administered to treat PAD or congestive heart failure.

The methods of the disclosure can also be practiced to produce antisense RNA, RNAi or other functional RNA (e.g., a ribozyme) for systemic delivery.

Injectables can be prepared in conventional forms, either as liquid solutions or suspensions, solid forms suitable for solution or suspension in liquid prior to injection, or as emulsions. Alternatively, one may administer the virus vector and/or virus capsids of the disclosure in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and virus capsids can be administered to tissues of the CNS (e.g., brain, eye) and may advantageously result in broader distribution of the virus vector or capsid than would be observed in the absence of the present disclosure.

In particular embodiments, the delivery vectors of the disclosure may be administered to treat diseases of the CNS, including genetic disorders, neurodegenerative disorders, psychiatric disorders and tumors.

Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis (ALS), progressive muscular atrophy, Pick's disease, muscular dystrophy, multiple sclerosis, myasthenia gravis, Binswanger's disease, trauma due to spinal cord and/or head injury (e.g., traumatic brain injury), Tay Sachs disease, Lesch-Nyan disease, epilepsy, stroke, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, any neurodegenerative condition that might benefit from or require axonal/neuronal regeneration and/or repair, cognitive disorders, behavioral disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present disclosure can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the disclosure.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present disclosure may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the disclosure can also be used to treat epilepsy, which is marked by multiple seizures over time.

In one representative embodiment, somatostatin (or an active fragment thereof) is administered to the brain using a delivery vector of the disclosure to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the disclosure, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intracerebroventricular, intracisternal, intraparenchymal, intracranial, intrathecal, intraocular, intracerebral, intraventricular, intravenous (e.g., in the presence of a sugar such as mannitol), intranasal, intraaural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201, 898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

The following examples, are included herein for illustration purposes only, and are not intended to be limiting.

EXAMPLES

Example 1. Discovery of a Neurotropic Footprint that Enables AAV Transport Across the Blood-Brain Barrier Adeno-associated viruses (AAV) are non-pathogenic parvoviruses composed of a small, 25 nm icosahedral capsid packaging an approximately 4.7 kb single-stranded DNA genome. A wide array of AAV capsid sequences have been isolated from human and primate tissues, which have been categorized into several distinct clades based upon sequence and structural diversity. Across these clades, different serotypes display broad tropism at the species, tissue and cellular levels. These diverse phenotypes are determined by capsid structure. The AAV capsid is assembled from 60 viral protein (VP) subunits. The core VP monomer (VP3) has a jellyroll, beta barrel structure comprised of 7 anti-parallel beta strands connected by interdigitating loop regions. Portions of these highly variable loops are surface exposed and define the topology of the AAV capsid, which in turn determines tissue tropism, antigenicity and receptor usage across the various AAV serotypes. The surface loop residues on the AAV capsid are highly plastic and amenable to modification, affording control over antigenicity, transduction profile and tissue tropism.

The first step in the AAV lifecycle is recognition of and attachment to cell surface glycan receptors. These include heparan sulfate (HS) for AAV2, AAV3 and AAV6, $\alpha 2,3$- and $\alpha 2,6$-N-linked Sialic acid (Sia) for AAV1, AAV5 and AAV6, O-linked sialic acid for AAV4, and galactose (Gal) for AAV9. Secondary to glycan binding, cellular uptake of AAV implicates secondary co-receptors, including various growth factor receptors as well as integrins. Recently, a transmembrane protein, KIAA0319L (AAVR) has been identified as a universal receptor for multiple AAV serotypes. These factors, along with tissue glycosylation patterns, contribute to the varying tissue tropisms of different AAV serotypes. Particularly with regard to the CNS, different AAV serotypes display a spectrum of transduction profiles and cellular tropisms, depending on the route of administration. For example, when directly administered into the mouse CNS through either direct intra-parenchymal or intra-cerebrospinal fluid (CSF) injections, AAV capsids undergo axonal transport and transynaptic spread in the anterograde and/or retrograde directions, depending on the serotype. Furthermore, we have recently shown that glial-associated lymphatic (glymphatic) transport of CSF influences AAV spread within the mouse brain parenchyma and clearance from the CNS.

To achieve CNS gene transfer, intravenously administered AAV vectors must first cross the blood-brain barrier (BBB) in order to gain entry into the brain. Comprised of endothelial cell tight junctions along with associated astrocytic end-feet and pericytes, the BBB blocks the diffusion and paracellular flux of macromolecules/particles and regulates the transport of other molecules. Most viruses which infect the brain do so through disrupting or weakening the BBB; however, some viruses have devised strategies to gain entry into the CNS by methods such as hitchhiking within host immune cells (e.g., HIV), by infecting brain endothelial cells or by infecting peripheral nerves and exploiting axonal transport (e.g., Rabies). In the case of AAV, the BBB prevents entry of most serotypes into the brain with a few notable exceptions. For instance, intravascular administration of AAV serotypes 1-6 and 8 results in poor CNS transduction, while isolates AAV9, AAVrh.8 and AAVrh.10 have been shown, amongst others, to efficiently traverse the BBB in different animal models.

In order to achieve therapeutic levels of transgene expression in the CNS, high vector doses (e.g., $1 \times 10^{14}$ vg/kg in the spinal muscular atrophy trial NCT02122952) are often required. In addition to burden associated with scale up and costs, high vector doses have also been shown to cause undesirable side effects such as liver toxicity. In order to improve the specificity/efficiency of gene transfer to the CNS and lower the effective vector dose, a better understanding of the structural features that enable AAV capsids to penetrate the BBB is needed.

To dissect structure-function correlates for crossing the BBB, we generated a combinatorial library of variant capsid genes using only two serotypes—AAV1, which does not traverse the vasculature, and AAVrh.10, which is known to efficiently cross the BBB. Rather than evolve new variants, we selected individual variants by computational, phylogenetic and structural analyses for further screening in mice.
Generation of a Chimeric AAV Capsid Panel.

An AAV1/rh.10 domain swap capsid library was generated through DNA shuffling. Briefly, the Cap genes of AAV1 and AAVrh.10 were randomly fragmented by brief DNase digestion and reassembled using primerless PCR with Phusion High-Fidelity DNA polymerase (NEB Cat #M0530L) in which the partial homology of the short (<400 bp) fragments allows for self-priming of the fragments. A secondary PCR step using specific conserved primers flanking the Cap gene were then used to amplify the library of reassembled full-length Cap sequences and simultaneously insert flanking restriction sites to facilitate subsequent cloning into a pTR plasmid backbone used for virus production.
Phylogenetic and Sequence Analyses The amino acid sequences of different AAV capsid isolates were aligned using ClustalW and phylogenetic trees were generated using the MEGAv7.0.21 software package. The phylogeny was produced using the neighbor-joining algorithm and amino acid distances were calculated using a Poisson correction. Statistical testing was done by bootstrapping with 1,000 replicates to test the confidence of the phylogenetic analysis and to generate the bootstrap consensus tree. Branches corresponding to partitions reproduced in less than 50% of bootstrap replicates are collapsed. The percentage of replicate trees in which associated taxa clustered together in the bootstrap test is displayed next to the branches. All sequence alignments were performed using Invitrogen's Vector NTI Advance 11.5.2 software.
Virus Production and Titers An updated triple plasmid transfection protocol was used to produce recombinant AAV vectors. Specifically, the transfected plasmids include (i) a capsid-specific pXR helper plasmid (i.e. pXR1, pXRrh.10, or various plasmids encoding the various chimeric Cap genes used in this study), (ii) the adenoviral helper plasmid pXX680, and (iii) either pTR-CBh-scGFP or pTR-CBA-Luc plasmids (encoding either a self-complementary green fluorescent protein (GFP) reporter transgene driven by the chicken beta actin hybrid (CBh) promoter or a luciferase reporter transgene (Luc) driven by the chicken beta actin promoter (CBA), respectively, flanked by inverted terminal repeats (TRs) derived from the AAV2 genome). Viral vectors were purified using iodixanol density gradient ultracentrifugation. Vectors packaging a CBh-scGFP transgene were subsequently subjected to buffer exchange and concentration using Sartorius Vivaspin2 100 kDa molecular weight cut-off (MWCO) centrifugation columns (F-2731-100 Bioexpress, Kaysville, UT). Vectors packaging a CBA-Luc transgene were subjected to buffer exchange and de-salting using Zeba Spin Desalting Columns, 40K MWCO (Thermo Scientific, Cat #87770). Following purification, viral genome titers were determined via quantitative PCR using a Roche Lightcycler 480 (Roche Applied Sciences, Pleasanton, CA). Quantitative PCR primers were designed to specifically recognize the AAV2 inverted terminal repeats (forward, 5'-AACATGC-TACGCAGAGAGGGAGTGG -3'; (SEQ ID NO:36) reverse, 5'-CATGAGACAAGGAACCCCTAGTGATG-GAG -3') (SEQ ID NO:37) (IDT Technologies, Ames IA).

Animal Studies

All animal experiments were performed using 6-to-8-week-old female C57/BL6 mice purchased from Jackson Laboratories (BAR Harbor, ME). These mice were maintained and treated in compliance with NIH guidelines and as approved by the UNC Institutional Animal Care and Use Committee (IACUC). To investigate the ability of AAV vectors to cross the BBB and transduce CNS cell populations, AAV vectors packaging a CBh-scGFP transgene or 1×PBS (as mock treatment) were administered intravenously (i.v.) via tail vein injection at a dose of $5 \times 10^{11}$ vg. To assay for GFP reporter transgene expression, animals were sacrificed 21 days post injection with tribromoethanol (Avertin) (0.2 ml of 1.25% solution) followed by transcardial perfusion with 30 ml of 1×PBS followed by 30 ml of 4% paraformaldehyde in PBS. Tissues including the brain, heart and liver were removed and post fixed for 24 h, and 50-µm-thick sections were obtained for each tissue using a Leica VT 1200S vibrating blade microtome (Leica Biosystems, IL). The mouse brain sections were then immunostained as described below. For in vivo luciferase transduction and viral genome biodistribution experiments, mice were injected with either 1×PBS or viral vectors packaging a CBA-Luciferase transgene at a dose of $1 \times 10^{11}$ vg. Mice were sacrificed, as described above, at 14 days post injection and various tissues were removed. For these experiments, no fixation with 4% paraformaldehyde in 1×PBS was performed and instead tissues were dissected and frozen at −80° C. prior to use.

To quantify luciferase expression, mice injected with $1 \times 10^{11}$ viral genomes packaging a CBA-Luc transgene were sacrificed at 14 days post injection and tissues were harvested and frozen at −80° C. Tissues were later thawed, weighed and lysed by adding 150 µl of 2× passive lysis buffer (Promega, Madison WI) prior to mechanical lysis using a Tissue Lyser II 352 instrument (Qiagen, Valencia, CA) followed by centrifugation to remove any remaining tissue debris. To measure luciferase transgene expression, 50 µl of supernatant from each lysate was then loaded onto an assay plate along with 50 µl of luciferin and luminometric analysis was performed using a Victor2 luminometer (PerkinElmer, Waltham, MA). The relative light units obtained for each sample were then normalized to the input tissue weight for each sample, measured in grams. Data was graphed and statistical analyses carried out using an unpaired two-tailed T-test with Welch's correction as well as ANOVA followed by Tukey's multiple comparisons test where indicated. These statistical analyses were performed in GraphPad Prism 6® software.

Tissue Processing and Histological Analysis

For mouse experiments using virus packaging a GFP reporter transgene, free-floating 50-µm-thick coronal brain sections were stained in 24-well plates. Sections were incubated in blocking buffer containing 10% goat serum and 1% Triton X (Sigma-Aldrich) in 1×PBS for 1 hour at room temperature. The sections were then incubated at 4° C. overnight with a primary monoclonal rabbit α-GFP antibody (Life-Technologies-G10, 362 1:750) diluted in blocking buffer. The next day, three 10 minute washes were performed with 1×PBS. The subsequent histochemical analysis of GFP expression was performed using a Vectastain ABC kit (Rabbit IgG PK-4001 kit, Vector biolabs, Burlingame, CA) and tissues were mounted onto microscopy slides. The immunostained sections were digitally imaged in brightfield (20× objective) using an Aperio ScanScope XT instrument (Aperio Technologies, Vista, CA) by the UNC Translational Pathology Laboratory and images were obtained using Leica eSlide Manager (centralized image storage and data management software) and analyzed using Aperio ImageScope and WebViewer software. Quantifications were calculated by counting the number of GFP+ neuronal or glial cells, determined based upon morphology, per 50 µm coronal brain section. Data was graphed and statistical analyses were performed as outlined above. Specific brain regions were identified based upon comparison to a coronal mouse brain reference obtained from the Allen Mouse Brain Atlas. To assay for GFP expression in the heart and liver, tissues were stained for GFP with the anti-GFP primary antibody as described above; however, an anti-rabbit goat antibody conjugated to Alexa-488 was used as the secondary antibody at a dilution of 1:500 (anti-rabbit Abcam-96,883). Immunostained GFP in these tissues was then imaged using an EVOS FL epifluorescence cell imaging system (AMC/Life Technologies) using the GFP light cube (excitation 470 nm, emission 510 nm). Statistical analyses were carried out as outlined earlier.

Vector Genome Biodistribution

Animal studies were performed as described above. At 21 days post injection, mice were sacrificed and tissues were frozen at −80° C. Tissues were later thawed and viral genomes were extracted from the tissue lysates using the DNeasy kit (Qiagen, Valencia, CA). Viral genome copy numbers were then determined for each tissue using quantitative PCR with primers specific to the luciferase transgene (forward, 5'-AAAAGCACTCTGATTGACAAATAC-3' (SEQ ID NO:38); and reverse, 5'-CCTTCGCTT-CAAAAAATGGAAC-3' (SEQ ID NO:39)). These viral genome copy numbers were then normalized to the mouse lamin B2 housekeeping gene using the primers (forward, 5'-GGACCCAAGGACTACCTCAAGGG-3' (SEQ ID NO:40); and reverse, 5'-AGGGCACCTCCATCTCG-GAAAC -3' (SEQ ID NO:41)). The biodistribution of viral genomes are represented as the ratio of vector genomes per cell recovered for each tissue. Data was graphed and statistical analyses carried out as described earlier.

Molecular Modeling

Previously published coordinates (PDB ID, 3NG9) were used to generate three-dimensional structures of the AAV1 VP3 trimer/three-fold axis of symmetry. Homology models of AAVrh.10 and various AAV1/rh.10 chimeric capsid structures were obtained using the SWISS-Model server (swiss-model.expasy.org), with the crystal structure of AAV8 VP3 (PDB ID, 2QA0) used as a template and a structure-based alignment was generated using the secondary structure matching (SSM) application in the WinCoot software, with the AAV1 VP3 (PDB ID 3NG9) monomer being used as a template. The VP3 trimers/3-fold symmetry axes, VP3 trimer dimers/2-fold symmetry axes, VP3 pentamers/5-fold symmetry axes, and full capsids were generated using the VIPERd oligomer generator utility (viperdb.scripps.edu/oligomer_multi.php). Surface rendered depictions of these models were visualized using PyMOL (the PyMOL Molecular Graphics System, SchrOdingerLLC, pymol.org). Stereographic roadmap projections of the AAV1RX capsid surface highlighting surface-exposed amino acid residues within the AAVrh.10-derived neurotropic footprint were generated using RIVEM (Radial Interpretation of Viral Electron Density Maps) software.

Generation of an AAV1/Rh.10 Domain Swap Library and Isolation of Chimeric Capsid Variants We performed a comparative analysis of different capsid domains to ascertain structure-function correlates for traversing the BBB. We generated an AAV1/rh.10 domain swap library through DNA shuffling. We selected AAV1 and AAVrh.10 as parental capsid sequences for DNA shuffling since they differ markedly in their abilities to cross the BBB and because of the sequence homology (85%) shared by their capsid (Cap) genes. Thirty-six chimeric capsid sequences were then clonally isolated and sequenced. The variants generated from this library displayed substantial diversity at the DNA and amino acid level. Sequence alignment revealed a spectrum of domain swaps, which we then organized in order of increasing homology from AAV1 to AAVrh.10 (FIG. 4A, top to bottom). This panel of clones was further characterized phylogenetically by constructing a neighbor-joining tree, which broadly categorized these variants as either more AAV1-like (Clade A) or more AAVrh.10-like (Clade E) (FIG. 4B). Small-scale vector production was then used to establish relative titers to exclude capsids defective in assembly or packaging from the study. Homology-based structural models of the parental and representative chimeric capsid trimers highlighting key surface domains/residues at the three-fold axis of symmetry (FIG. 4C) were generated to further narrow the list of chimeric capsid variants for initial screening in vivo. Ten chimeric capsid variants were selected based on structural analyses, out of which six yielded recombinant vectors (packaging scGFP or ssLuc transgene cassettes) at titers similar to parental AAV1 and AAVrh.10 vectors. These variants were then screened further.

In Vivo Screening Identifies Two AAV1/Rh.10 Chimeric Capsids Capable of Crossing the BBB after Intravenous Administration in Adult Mice We then tested whether the selected panel of capsid variants would differ in their ability to cross the BBB and transduce the CNS after I.V. administration. It is important to note that our approach did not involve directed evolution, as this strategy is generally applicable for selecting optimal capsids and less suited for studying structure-function relationships. We injected 6-8-week-old mice with a dose of $5\times10^{11}$ viral genomes (vg) per mouse of AAV1, AAVrh.10, or one of six different chimeric AAV vectors packaging a self-complementary CBh-GFP reporter cassette via tail vein injection.

GFP positive neurons in the cerebral cortex were manually counted, quantified and averaged across multiple coronal brain sections per mouse. n=2 for AAV1; n=3 for AAV1R6 and AAV1R7 (FIG. 1). Immunostaining of coronal brain sections at three weeks post-injection revealed that AAV1 transduction in the cerebral cortex was limited to the vasculature while AAVrh.10 demonstrated robust transduction of various cell populations, including neurons, glia and endothelial cells, as determined morphologically (FIG. 2, FIG. 5). Further morphological assessment of GFP+ cells indicates differing phenotypes for the chimeric variants. AAV1R19.1 and AAV1R20 transduce predominantly microvascular endothelial cells in the cortex, while low to modest transduction of neuronal and glial cells is evident for AAV1R8 and AAV1R19d vectors (FIG. 5). In contrast, AAV1R6 and AAV1R7 demonstrate robust transduction of cortical neurons with modest transduction of glia and scarce, if any, transduction of the vasculature within the cortex. Representative images of the somatosensory area of the cortex at high magnification are shown. A similar trend for these chimeras was observed consistently across other regions of the brain (FIG. 6). These observations indicate that the chimeric capsids AAV1R6 and AAV1R7 likely possess the ability to cross the BBB, similar to the parental AAVrh.10 vector, although the mechanism is unknown. However, unlike either parent, AAV1 or AAVrh.10, neither chimera efficiently transduces the vasculature.

Intravenously Delivered AAV1R6 and AAV1R7 Chimeric Capsids Cross the BBB and Transduce Neurons Preferentially Throughout the Brain.

We then further characterized the transduction profiles of these variants across multiple functionally relevant structures of the brain. For each of the brain regions discussed below, representative images at higher magnification were obtained from mouse brain coronal sections immunostained for GFP and scanned in bright field at 20× magnification. Additionally, quantitative data for neuronal and glial transduction for each region were determined by counting GFP+ neuronal and glial cells, respectively, based on cellular morphology.

Cerebral Cortex.

AAVrh.10 displays robust transduction of neuronal, glial and vascular endothelial cells throughout the cortex and, in the case of intravascularly delivered AAV1, vascular transduction accompanied by the absence of neuronal expression and low expression levels in glia was observed (FIG. 7 and FIG. 8). We also observed that intravenously administered AAV1R6 and AAV1R7 (AAV1R6/7) vectors mediate robust GFP expression in cortical neurons and reduced expression in glia throughout the amygdalar, piriform, entorhinal, temporal association, auditory, somatosensory, motor, posterior parietal and retrosplenial areas of the cortex yet varied at consistently trending levels across the sections analyzed. Representative images of cortical regions transduced are shown for the motor cortex (FIG. 7A) and the somatosensory area of the cortex (FIG. 7B). Furthermore, AAV1R6/7 seem to display a preferentially neuronal cellular tropism across the entire cortex, showing moderate glial transduction and remarkably reduced vascular transduction. This profile is in stark contrast to the vasculotropic AAV1 as well as AAVrh.10, which transduces neuronal, glial, and vascular endothelial cells with high efficiency (FIGS. 7A and 7B). While AAV1R6/7 mediate robust neuronal and moderate glial expression throughout the cortex, their expression levels are nonetheless lower than those achieved by AAVrh.10. These trends are corroborated by quantitation of our morphological analysis of GFP+ cells (FIGS. 8A and 8B), which show a statistically significant difference in cortical transduction relative to AAV1 for AAVrh.10, AAV1R6 and AAV1R7. One last difference to note is that AAVrh.10 transduction across the cortex has a tendency to be concentrated at the peripheries of the tissue, around cortical layers 1-3, particularly within the retrosplenial, motor, somatosensory and visual cortical areas. While this can be attributed to differential immunostaining, we observed this phenomenon with high consistency across the stained AAVrh.10 sections in our analysis. This trend does not hold true for AAV1R6/7, which appear to mediate more uniformly distributed expression across the cortical layers.

Hippocampus.

Figure 8:
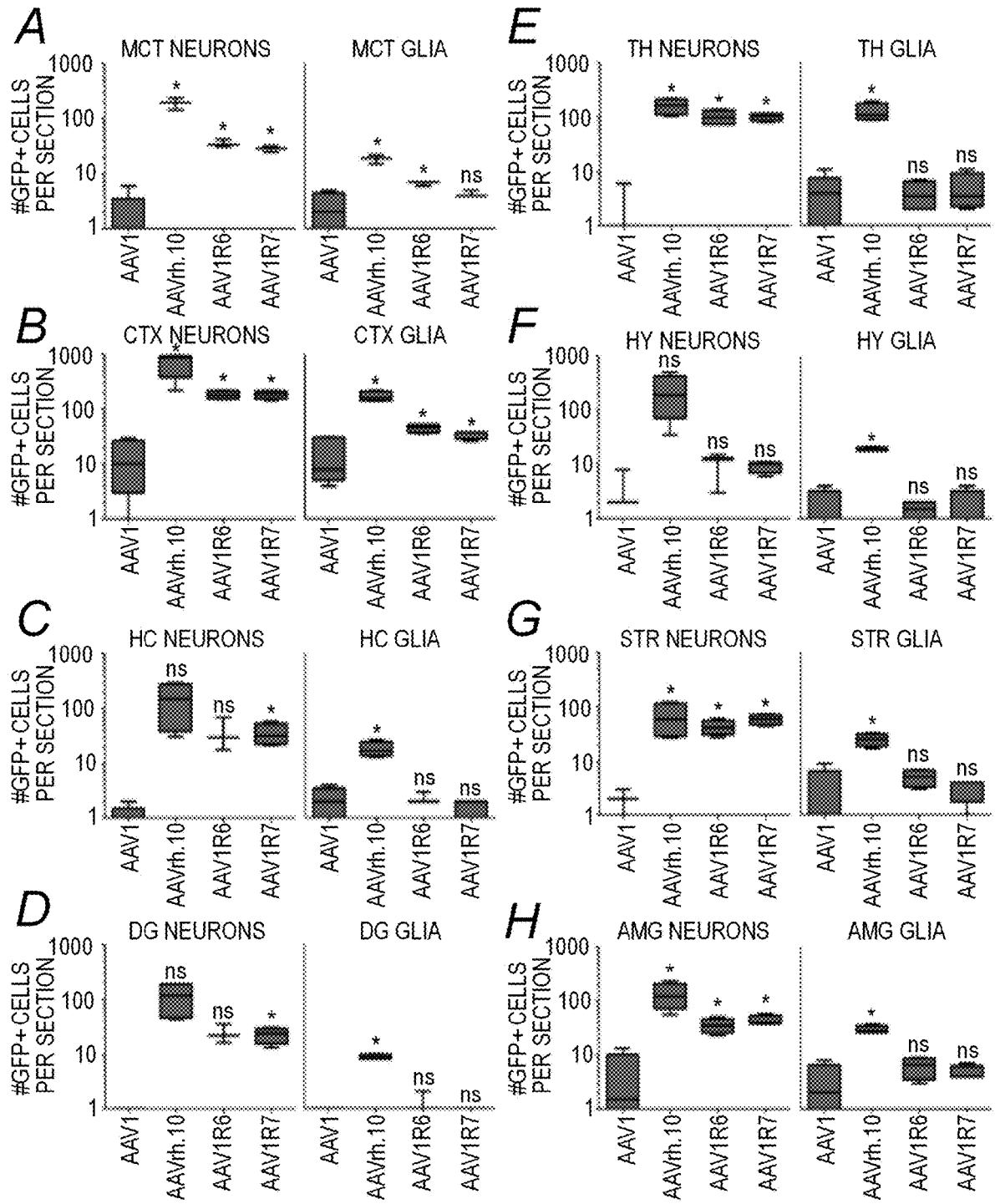
FIGS. 8A-8H. Quantitative comparison of neuronal and glial transduction levels for parental and chimeric capsid variants. Relative neuronal transduction levels at 3 weeks post administration of vectors packaging a CBh-scGFP transgene via tail vein injection at a dose of $5\times10^{11}$ vg were quantified by counting the number of transduced neurons and glia, identified based on morphology, for each brain region, per 50 µm coronal section. Transduction of parental serotypes, AAV1 and AAVrh.10, are shown alongside the chimeric variants, AAV1R6 and AAV1R7, across various regions of the brain, including the motor cortex (FIG. 8A), cerebral (somatosensory) cortex (FIG. 8B), hippocampus (FIG. 8C), dentate gyrus (FIG. 8D), thalamus (FIG. 8E), hypothalamus (FIG. 8F), striatum (FIG. 8G), and amygdala (FIG. 8H). Error bars represent standard deviation (n> or =3). An unpaired two-tailed T-test with Welch's correction and one-way ANOVA were used to demonstrate statistical significance for neuronal and glial transduction by each group relative to AAV1, and that differences between the means were statistically significant, respectively. ns, not significant; *, $P<0.05$.

Following intravenous delivery, the chimeric AAV1R6/7 vectors appear to mediate robust GFP expression in neurons throughout the hippocampus, bilaterally across brain hemispheres. GFP+ hippocampal neurons are observed within the CA1, CA2 and CA3 pyramidal layers (FIG. 7C, CA2 and partial CA1 shown). AAV1R6/7 also appear to be effective at transducing neurons within the dentate gyrus, showing a large number of GFP+ neurons which appear to be granular cells based on morphology (FIG. 7D). The neuronal transduction profile displayed by AAV1R6/7 in the hippocampus is similar to that seen for AAVrh.10. In contrast to AAVrh.10, however, AAV1R6/7 do not appear to transduce either glia or endothelial cells in either region at any appreciable level, with no significant difference in GFP+ glial cells observed between AAV1 and AAV1R6/7 (FIGS. 8C and 8D). AAV1 transduction observed in the hippocampus is again limited to the vasculature. Furthermore, these qualitative trends are corroborated by quantitative data for neuronal and glial cell transduction in the hippocampus (FIG. 8C) and dentate gyrus (FIG. 8D).

Thalamus.

GFP+ neurons were detected in the thalamus for AAV1R6/7 at levels comparable to AAVrh.10 (FIG. 7E). Furthermore, AAV1R6/7 demonstrate minimal transduction of the endothelium and dramatically reduced levels of glial transduction in the thalamus compared to AAVrh.10. These trends are further corroborated by quantitative data (FIG. 8E) in which transduction of thalamic neurons was found to be significantly different for AAVrh.10, AAV1R6 and AAV1R7, relative to AAV1. Contrarily, no significant difference was found for thalamic glial transduction for AAV1R6/7 relative to AAV1.

Hypothalamus.

Although somewhat variable, we observed consistently low levels of GFP expression, regardless of cell type, within the hypothalamus for parental and chimeric vectors when administered systemically (FIG. 7F). Variation in neuronal transduction levels in the hypothalamus was observed for AAVrh.10, revealing high as well as low numbers of GFP+ neurons across mice. This transduction profile is illustrated by the deviation shown for AAVrh.10 transduction in our quantitative data (FIG. 8F). AAV1 displays moderate hypothalamic transduction that is restricted to the vasculature. AAV1R6/7 vectors demonstrate low numbers of GFP+ neurons and glial cells in the hypothalamus, and a small number of GFP+ endothelial cells (FIG. 7F and FIG. 8F).

Striatum.

AAV1R6/7 transduce neurons in the striatum (specifically, the caudate putamen) as efficiently as AAVrh.10 (FIG. 7G), as corroborated further by our quantitative data demonstrating a significant difference for each relative to AAV1; however, these vectors transduce ~2-fold fewer glial cells and lower numbers of endothelial cells in the striatum (FIG. 8G) despite some observed variation.

Amygdala.

The amygdalar transduction profiles for AAV1R6/7 show robust neuronal GFP expression, significantly different compared to AAV1. Few GFP+ glial cells were detected, which were not significantly different compared to AAV1 (FIG. 7H and FIG. 8H), and barely detectable GFP+ endothelial cells were observed, similarly to other brain regions such as the striatum and thalamus.

Taken together, the morphological assessment of immunostained brain regions derived from mice following intravenous delivery of AAV1R6 and AAV1R7 demonstrates robust and selective neuronal transduction comparable to parental AAVrh.10. Furthermore, these chimeras display reduced glial transduction and their ability to transduce endothelial cells of the brain microvasculature appears diminished. Furthermore, these results appear to be consistent across various brain regions, with the exception of the hypothalamus, where low transduction levels in general are observed.

AAV1R6 and AAV1R7 are De-Targeted from the Liver while Retaining Parental Cardiac Transduction Profiles We analyzed the relative cardiac and liver transduction of these variants compared to parental serotypes by immunostaining cardiac and liver sections. 6-8 week old female BL6 mice were administered systemically via tail vein injections with a dose of $5\times10^{11}$ vg of vectors packaging a hybrid chicken beta actin promoter (CBh) linked to a green fluorescent protein (GFP) coding sequence (CBh-scGFP) (either AAV1, AAV1R6 or AAV1R7) or with PBS as a negative control. Mice were sacrificed 21 days post injection and tissues were harvested, fixed, and sectioned. Microscopy was used to visualize GFP reporter transduction. GFP expression was quantified by averaging relative fluorescence for multiple images per mouse using ImageJ software. n=1 for mock, n=2 for AAV1 and n=3 for AAV1R6 and AAV1R7.

Figure 10:
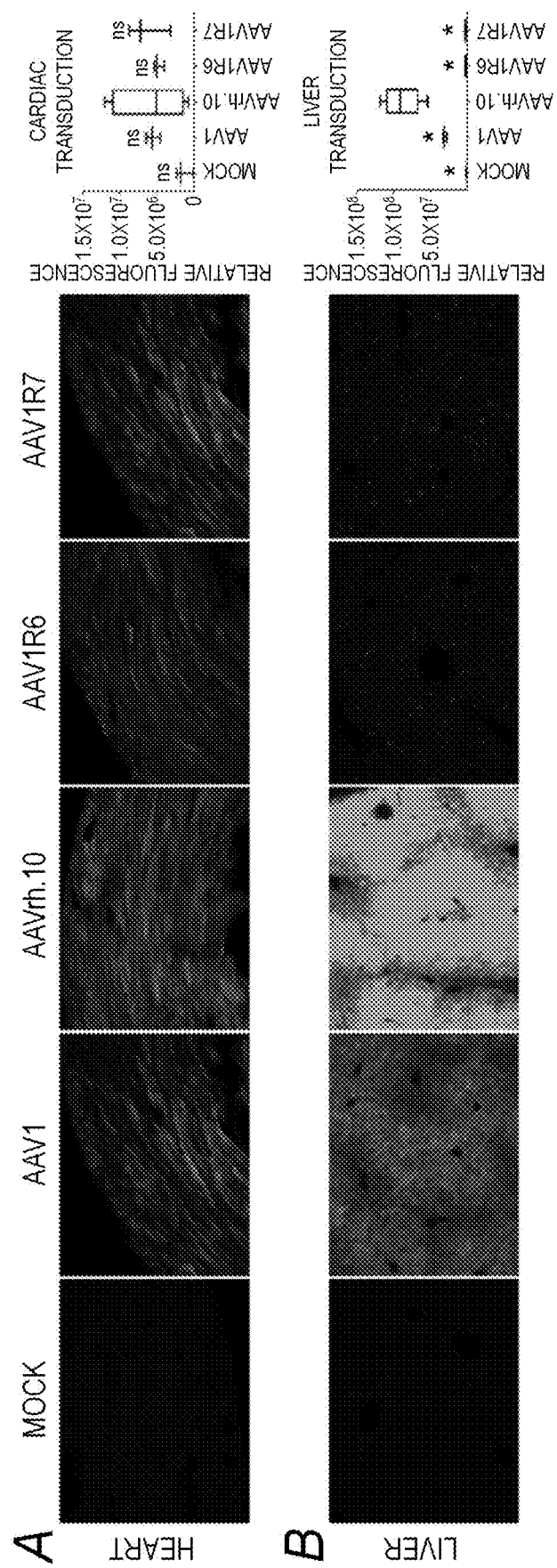
FIGS. 10A-10B. Relative cardiac and liver transduction by AAV1R6 and AAV1R7 compared to parental capsids. Either parental (AAV1 or AAVrh.10) or chimeric (AAV1R6 or AAV1R7) vectors packaging a CBh-scGFP transgene were administered at a dose of $5\times10^{11}$ vg via tail vein injection. At 21 days post injection, heart and liver sections were immunostained for GFP and imaged.

As shown in FIG. 10, both chimeric vectors demonstrate comparable levels of GFP expression in the heart relative to the parental serotypes, AAV1 and AAVrh.10, with no significant difference found for AAVrh.10, AAV1R6 or AAV1R7, relative to AAV1; however, AAVrh.10 expression levels in cardiac tissue showed substantial variation across mice (FIGS. 10A and 10B). In the liver, AAV1 demonstrated moderate transduction levels while AAVrh.10 performed exceptionally well, demonstrating a log-fold higher transduction. In contrast, AAV1R6 and AAV1R7 mediated negligible GFP expression in the liver at background levels comparable to mock-treated mice (FIG. 10B) that were significantly reduced relative to AAVrh.10. Thus, we conclude that AAV1R6 and AAV1R7 are liver-de-targeted relative to their parental serotypes.

Figure 3:
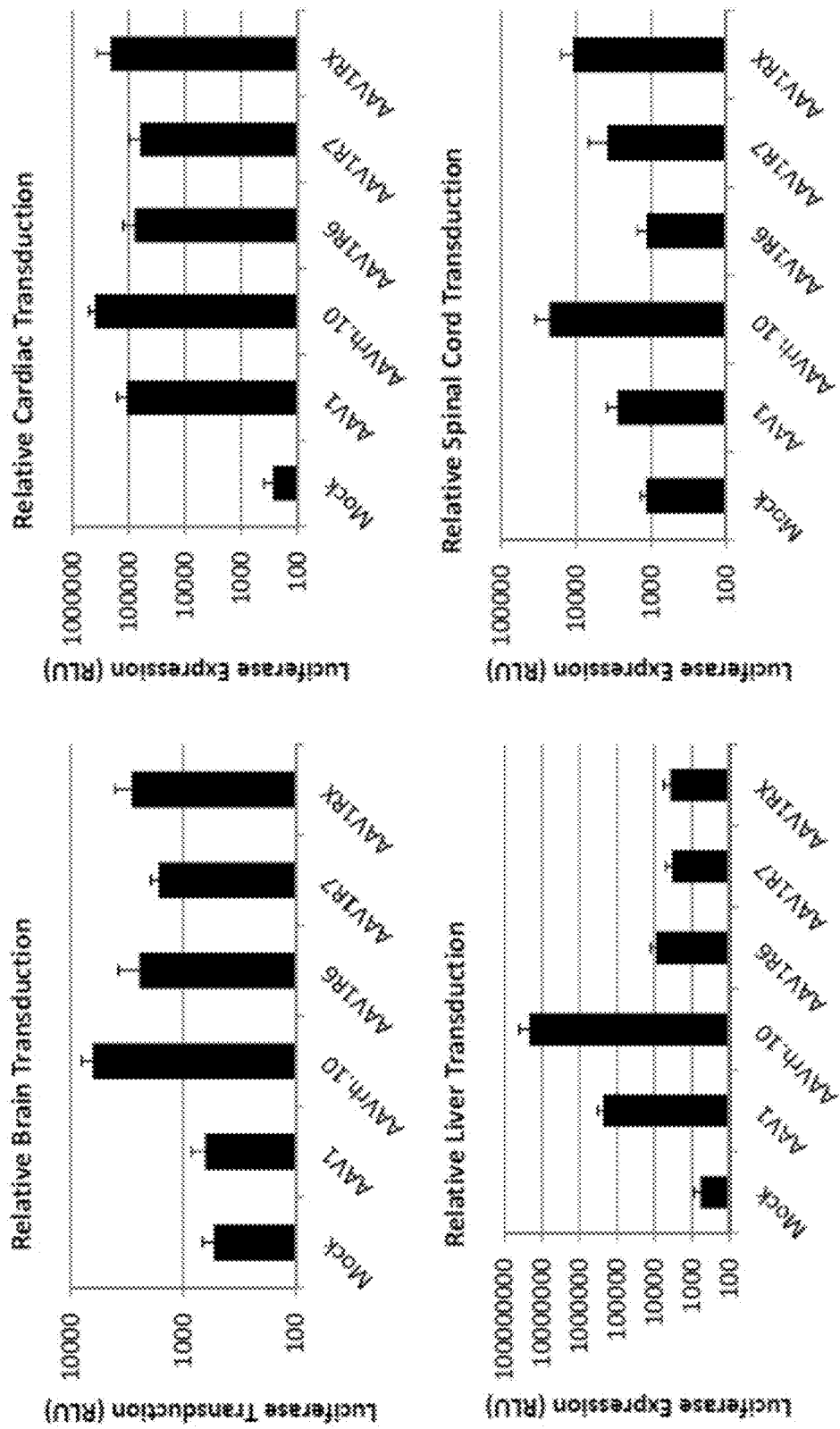
FIG. 3. Liver detargeting. AAV vectors packaging a CBA-luciferase transgene were administered to C57/B16 mice via tail vein injection at a dose of $1 \times 10^{11}$ vg. Mice were sacrificed at 14 days post injection, tissues were harvested, chopped up, lysed and luciferase assays were performed to detect relative transduction levels for brain, cardiac, liver, and spinal cord tissues. Data were normalized as relative light units per gram tissue. N=3.
Figure 4:
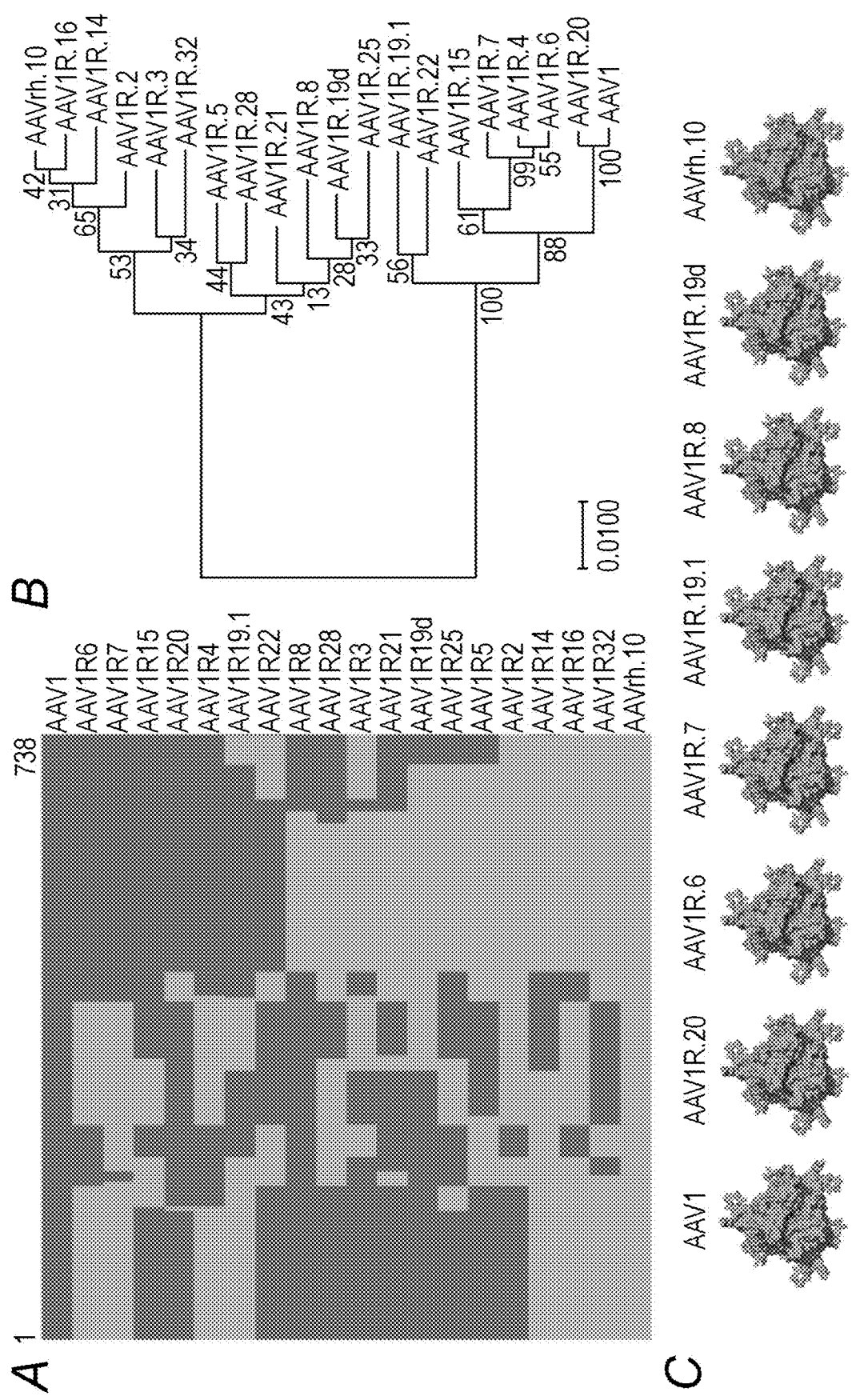
FIGS. 4A-4C. Phylogenetic and structural analyses of the AAV1/rh.10 domain swap capsid library.
Figure 5:
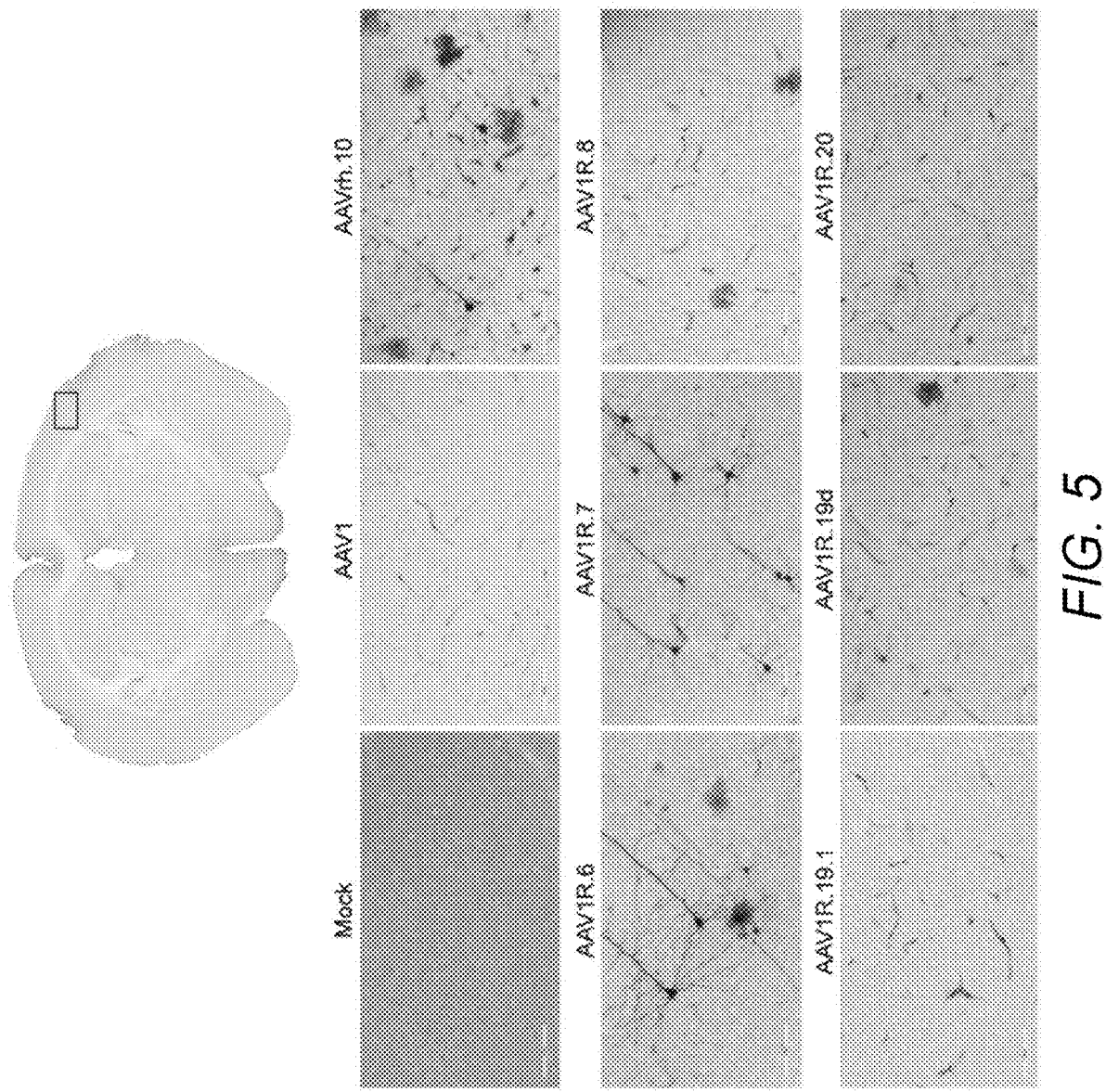
FIG. 5. In vivo screen yields AAV1/rh.10 chimeras capable of crossing the blood-brain barrier following intravenous administration. Scans of immunostained brain sections showing GFP expression in the cerebral cortex mediated by parental or chimeric vectors packaging a CBh-scGFP transgene at three weeks post-administration via tail vein injection at a dose of $5 \times 10^{11}$ vg (or PBS in the case of mock treatment). The global coronal brain section (top) indicates the boxed region of the cortex seen in the insets shown for each parental or chimeric vector, representing their individual transduction profiles. Scale bar=100 μm.
Figure 6:
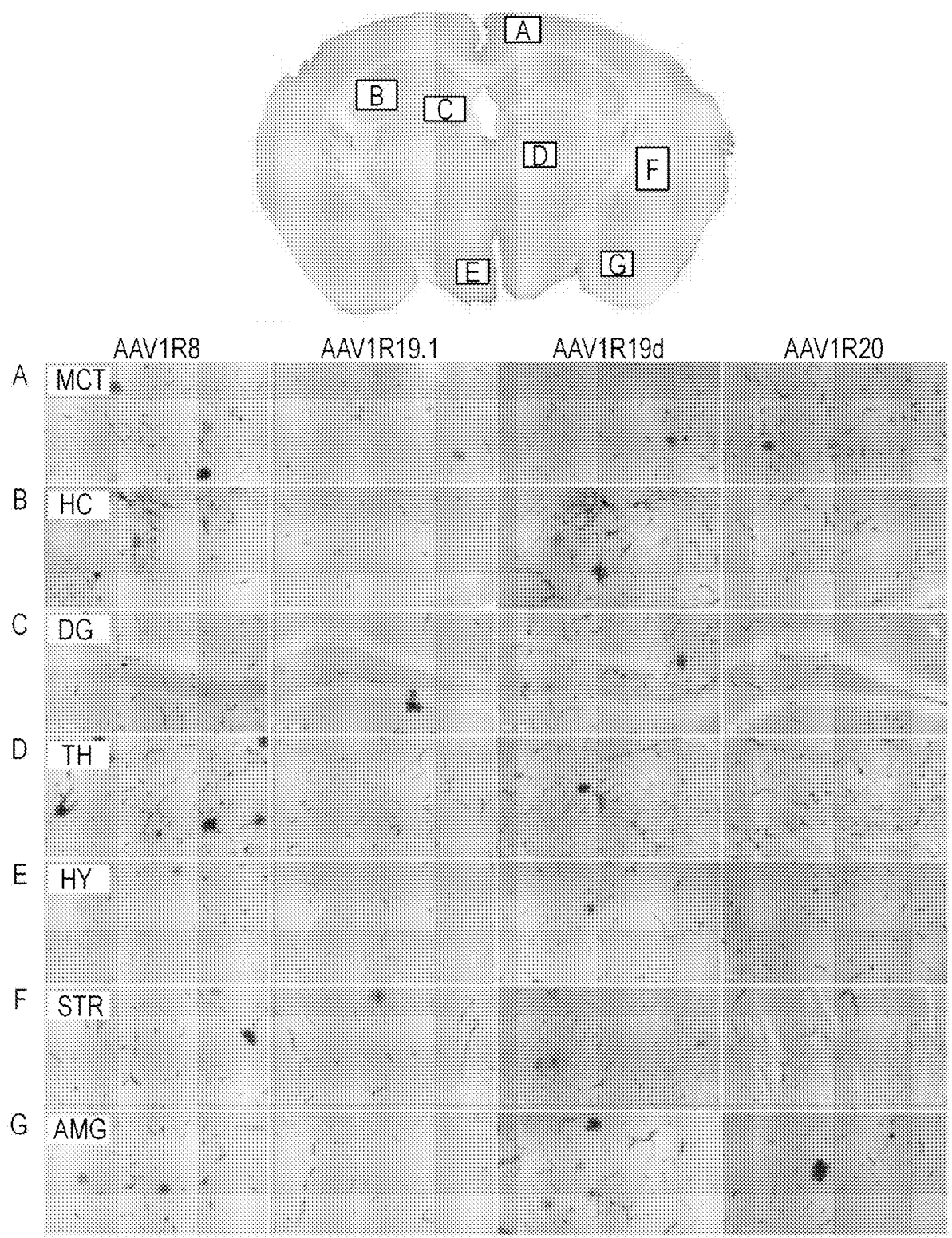
FIGS. 6A-6G. In vivo screen of AAV1/rh.10 chimeras for their ability to cross the blood-brain barrier and transduce various brain regions following intravascular administration. Mice received a dose of $5 \times 10^{11}$ vg of either parental (AAV1 or AAVrh.10) or chimeric vector packaging a CBh-scGFP transgene via tail vein injection. Immunostained and imaged mouse brain sections show GFP expression, as black/dark staining, at 21 days post injection. Scale bar=100 μm. The global coronal brain section at the top of the figure indicates the various brain regions shown in the insets: MCT, motor cortex (FIG. 6A); HC, hippocampus (FIG. 6B); DG, dentate gyrus (FIG. 6C); TH, thalamus (FIG. 6D); HY, hypothalamus (FIG. 6E); STR, striatum (FIG. 6F); Amg, amygdala (FIG. 6G). n=3 for each.

Separately, AAV vectors packaging a chicken beta actin (CBA) promoter linked to a luciferase coding sequence to produce a CBA-luciferase transgene were administered to C57/B16 mice via tail vein injection at a dose of $1\times10^{11}$ vg. Mice were sacrificed at 14 days post injection, tissues were harvested, chopped up, lysed and luciferase assays were performed to detect relative transduction levels for brain, cardiac, liver, and spinal cord tissues. Data was normalized as relative light units per gram tissue. In the brain, AAV1R6, AAV1R7 and AAV1RX display considerable transduction levels, albeit not as high as AAVrh.10 (FIG. 3). The chimeric capsids additionally display transduction levels comparable to the parental AAV1 and AAVrh.10 capsids in the heart. In the spinal cord, transduction levels for the chimeras appear to be intermediate between the parents. Strikingly, this data further demonstrates that AAV1R6, AAV1R7 are AAV1RX are all liver-detargeted. N=3.

Structural Analysis of the AAV1R6 Chimeric Capsid Identifies Three Potential Domains from AAVrh.10 that Might Enable Crossing the BBB Sequence analyses revealed that AAV1R6 is 97-98% identical to AAV1 with 18 unique amino acid residues derived from AAVrh.10. AAV1R7 is also largely identical to AAV1, but with a total of 22 AAVrh.10-derived residues, including the 18 present in AAV1R6. Of the 4 additional residues unique to AAV1R7, two are located within the VP1 unique (VP1u) N-terminal region (189I, 206A) and the other two are located at the buried VP3 N-terminal region (224S and 225S). Since these residues are not exposed on the capsid surface and since the in vivo data suggests that the transduction profiles displayed by AAV1R6 and AAV1R7 are equivalent (FIGS. 7 and 8), we excluded AAV1R7 from the remainder of our analyses and focused on AAV1R6 alone.

Figure 9:
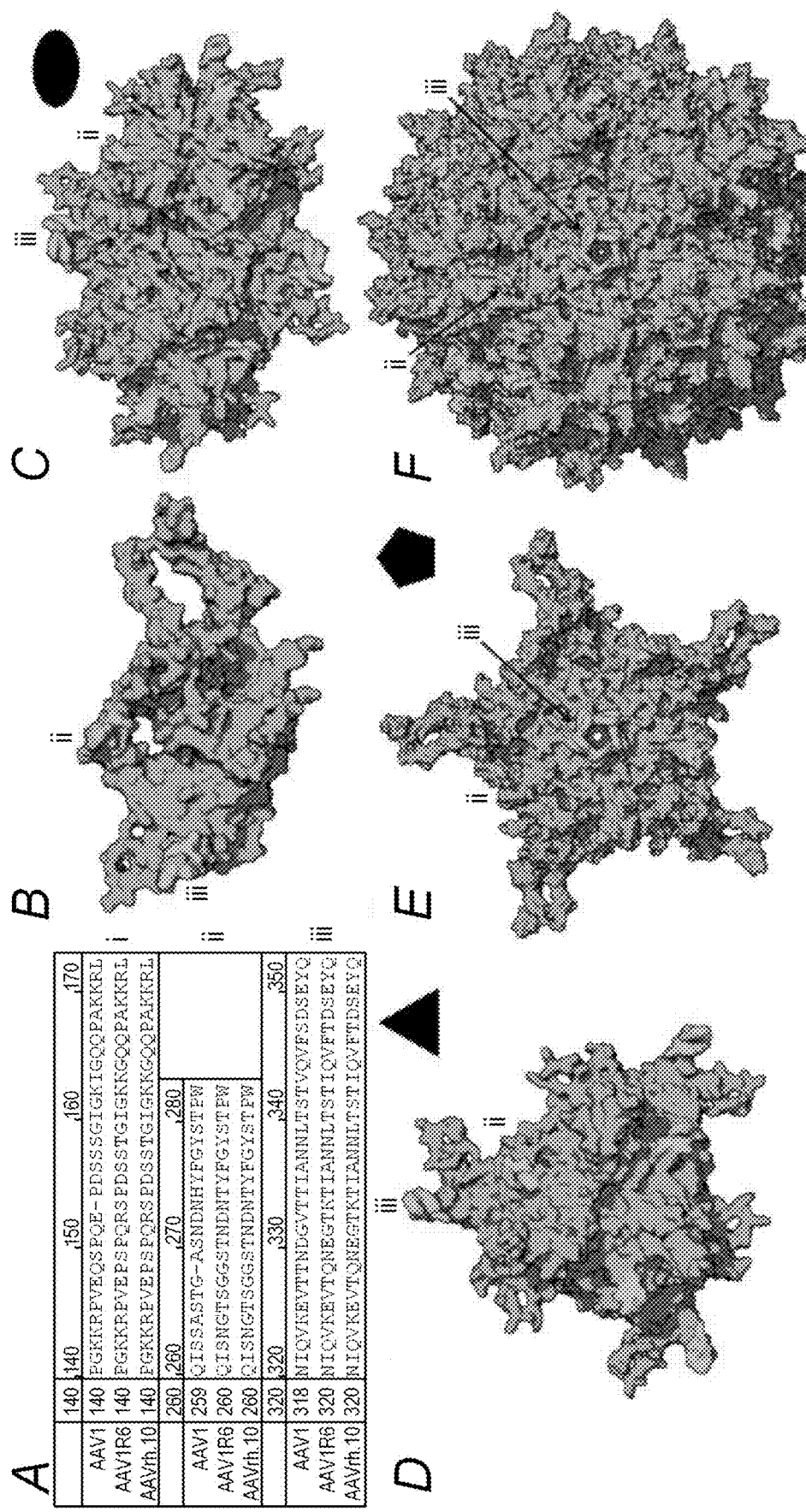
FIGS. 9A-9F. Structural analysis of the AAV1R6 chimeric capsid variant.

AAV1R6 possesses 3 stretches of non-consecutive residues derived from the AAVrh.10 parental strain. The first group of residues (group i) includes three amino acids (148P, 152R and 153S) within the VP1u region (FIG. 9A). Specifically, one residue is located adjacent to basic region 1 (BR1), which contains the first nuclear localization signal (NLS) of VP1. Additionally, group i contains two residues (158T and 163K) also near the NLS located within the VP2 N-terminal region (FIG. 9A) As mentioned earlier, these residues are not surface-exposed and instead remain internalized within the capsid until later in the intracellular trafficking pathway.

The second group of AAVrh.10-derived residues on AAV1R6 (group ii) consists of 8 amino acids comprising the BC loop, located within variable region I (VR-I) (FIGS. 9A and 9B). These residues are exposed on the surface of the capsid at the base of the protrusions at the 3-fold axis of symmetry (FIGS. 9D and 9F) and are also localized to the depression at the 2-fold symmetry axis (FIGS. 9C and 9F). It is also important to note that this group of amino acid residues on AAVrh.10 is substituted with AAV1 residues in the chimeric AAV1R8/19/20 capsids that are unable to penetrate the CNS after systemic administration.

The third group of AAVrh.10-derived residues present in AAV1R6 (group iii) includes a total of 6 amino acids. Four of these residues (328Q, 330E, 332T and 333K) are located at VR-II, within the DE loop, which contributes to formation of the pore at the 5-fold axis of symmetry (FIG. 9A, 9B, 9E, 9F). The last two remaining residues within this group (343I and 347T) are located within R-strand E, positioned within the interior of the capsid (FIGS. 9A and 9B). Although these residues differ between AAV1 and AAVrh.10, it should be noted that they are relatively conserved across different AAV serotypes.

Figure 11:
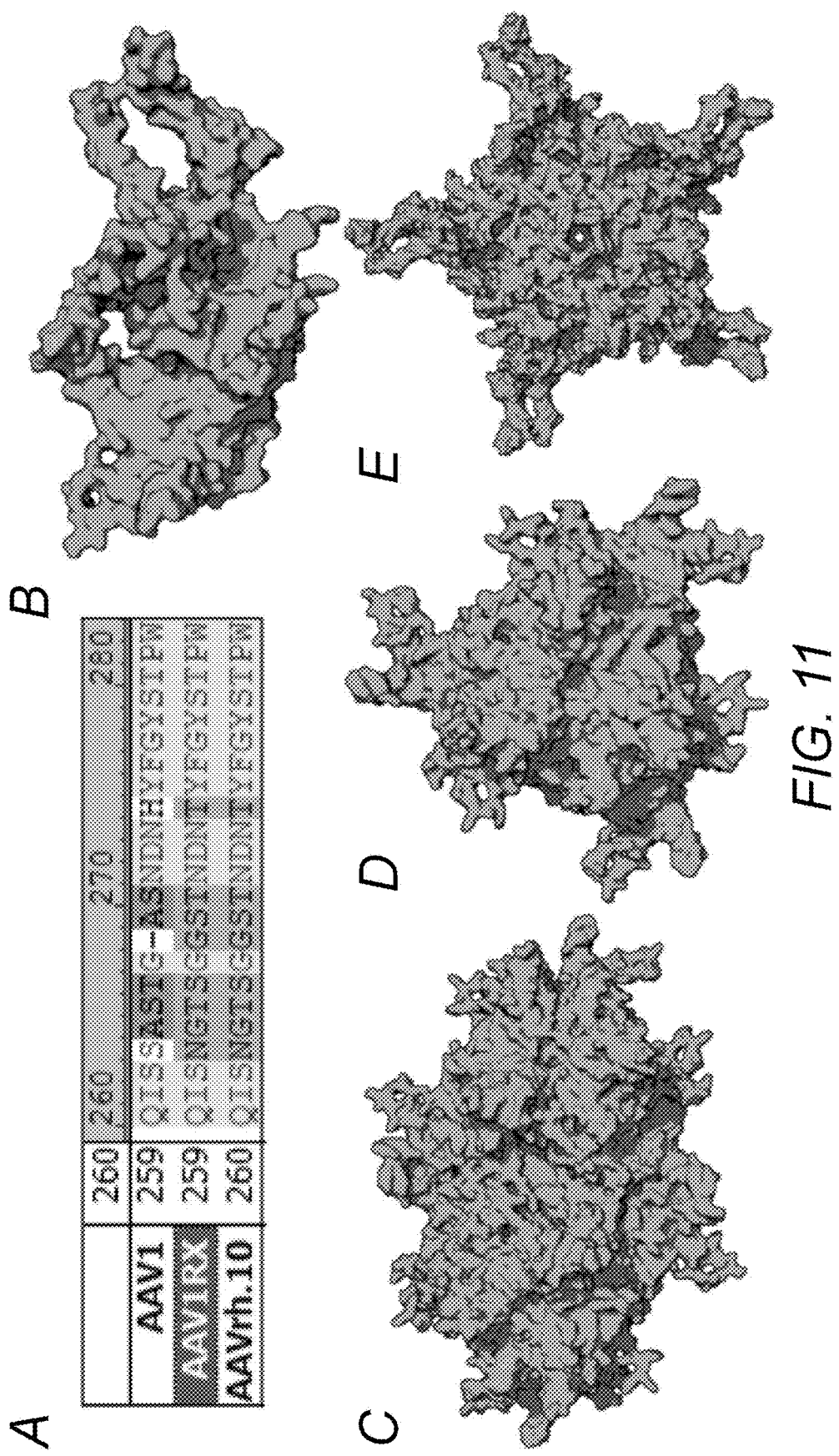
FIGS. 11A-11H. Rational design and functional mapping of a minimal AAVrh.10 footprint for crossing the BBB.
Figure 11:
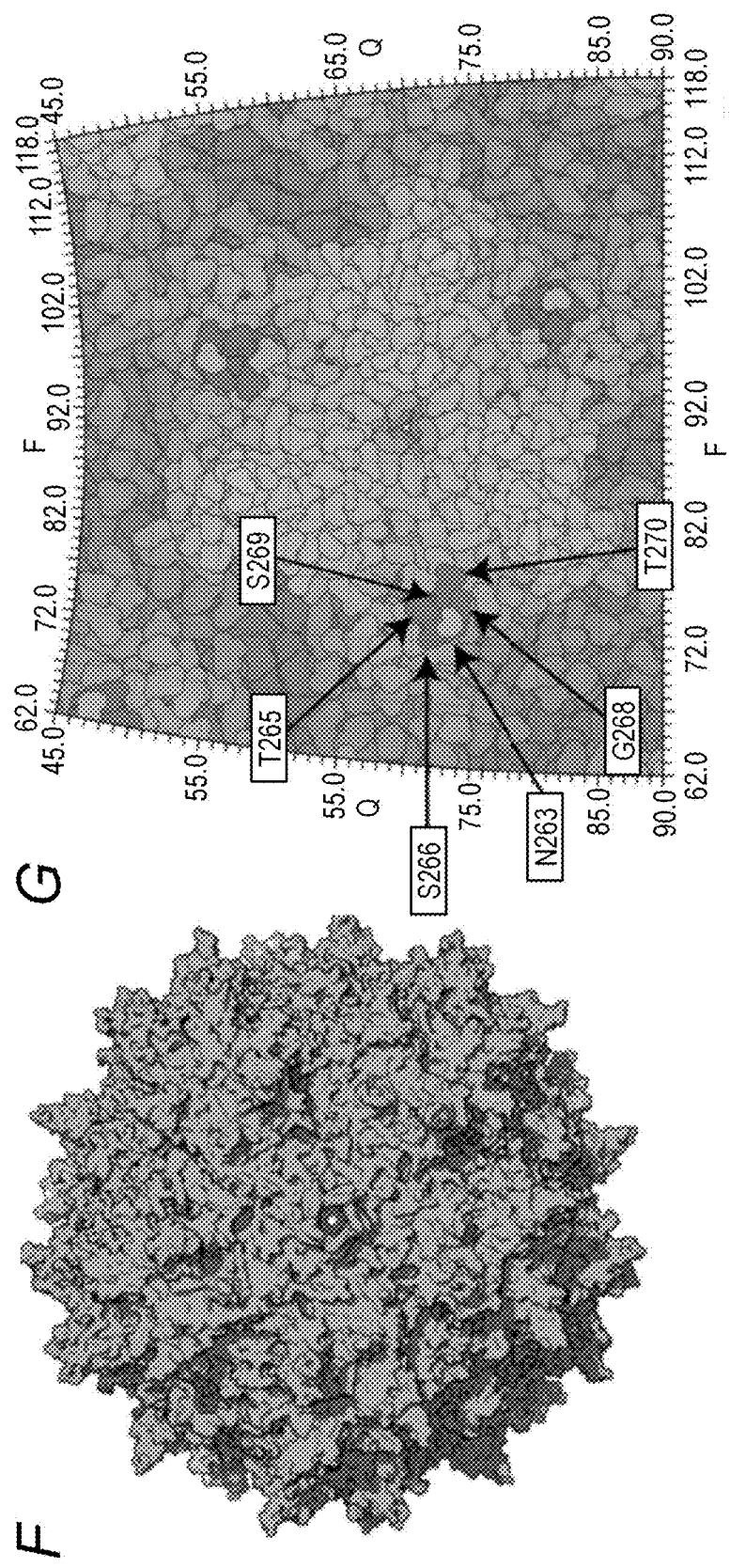
Figure 11:
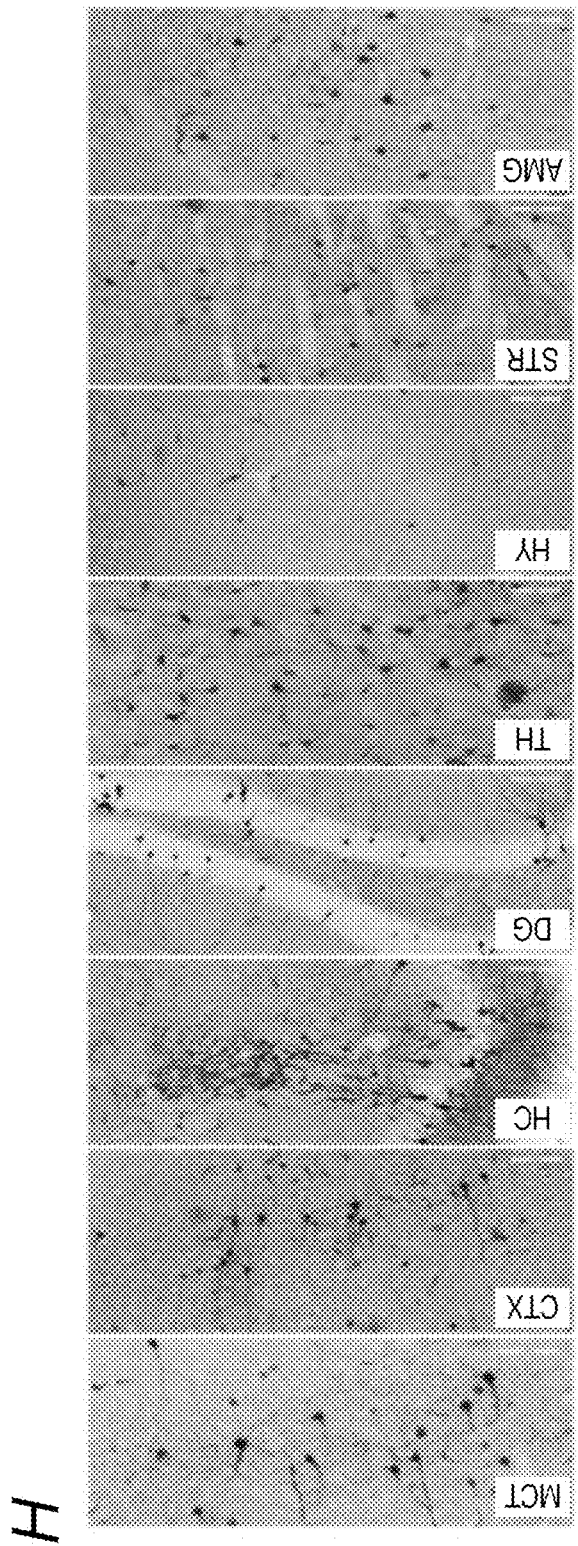

Rational Design of AAV1RX, a Chimeric Capsid with a Minimal Footprint from AAVrh.10 for Crossing the BBB Using a rational approach, we narrowed down the minimum number of AAVrh.10-derived amino acid residues in the 1R6 footprint that enable crossing the BBB and impart CNS tropism. We first excluded any amino acids that were not exposed on the capsid surface, eliminating stretches of residues located within the VP1/2 N-terminal regions of the capsid sequence (148P, 152R, 153S, 158T and 163K). Using the same rationale, we also excluded residues within the conserved β-strand E (343I and 347T) as well as those residing within VR-II, which is the pore-forming loop connecting β-strands D and E (328Q, 330E, 332T and 333K). Through this approach, the footprint containing 8 amino acids (263N, 264G, 265T, 266S, 268G (an insertion relative to the AAV1 sequence), 269S, 270T and 274T) found within VR-I, the loop bridging β-strands B and C, on AAV1R6 was chosen for further evaluation (FIGS. 11A and 11B). These surface-exposed residues are located near the depression at the 2-fold axis of symmetry (FIGS. 11C and 11F) and at the base of the three-fold protrusions (FIGS. 11D and 11F). The stereographic roadmap projection of surface-exposed residues at the 3-fold axis of symmetry highlights the topological orientation of these 8 residues in relation to the surrounding amino acids at the capsid surface (FIG. 11G). As mentioned earlier, we also took into account that these amino acids were absent in the AAV1R8/19/20 vari-ants that were unable to transduce the brain parenchyma following systemic administration.

Figure 13:
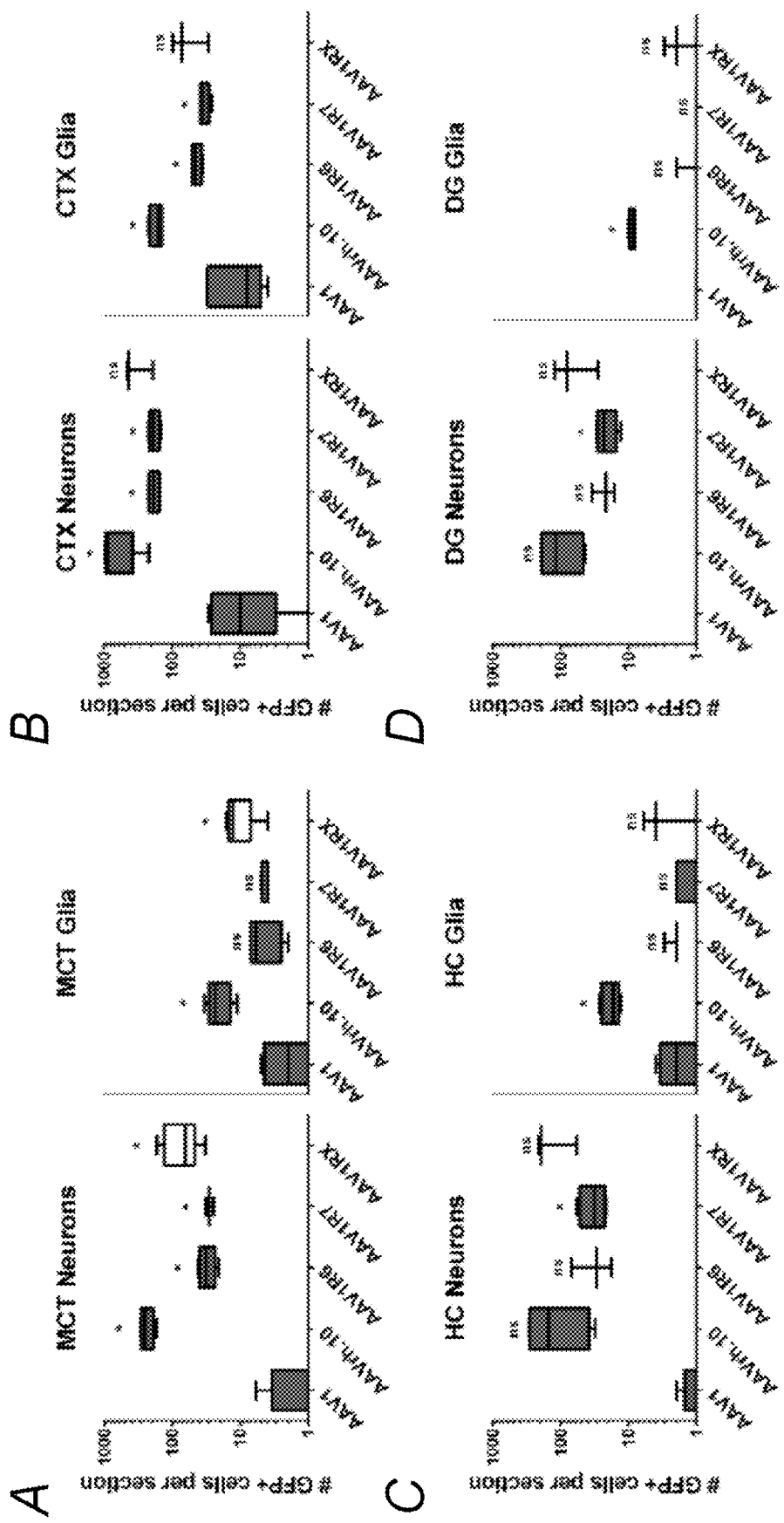
FIGS. 13A-13H. Quantification of neuronal and glial transduction levels mediated by AAV1RX compared to parental and other chimeric capsid variants. Mice received a dose of 5×10$^{11}$ vg of either parental (AAV1 or AAVrh.10) or chimeric vector packaging a CBh-scGFP transgene via tail vein injection. At 3 weeks post injection, brains were taken, sectioned, immunostained for GFP and imaged. Relative neuronal and glial transduction levels were immunostained for GFP and imaged. Relative neuronal and glial transduction levels were quantified by counting the number of transduced neurons and glia, identified based on morphology, for each region per 50 µm coronal section. AAV1RX transduction levels are shown alongside those for parental serotypes, AAV1 & AAVrh.10, as well as the chimeric variants, AAV1R6 and AAV1R7, across various regions, including the motor cortex (FIG. 13A), cerebral cortex (FIG. 13B), hippocampus (FIG. 13C), dentate gyrus (FIG. 13D), thalamus (FIG. 13E), hypothalamus (FIG. 13F), striatum (FIG. 13G), and amygdala (FIG. 13H). Error bars represent standard deviation (n=3). An unpaired two-tailed T-test with Welch's correction was used to demonstrate statistical significance of each group relative to AAV1. ns: not statistically significant; *, P<0.05. One-way ANOVA was also used to demonstrate that differences among means are statistically significant. *, P<0.05 for neuronal and glial transduction across all brain regions shown here.
Figure 13:
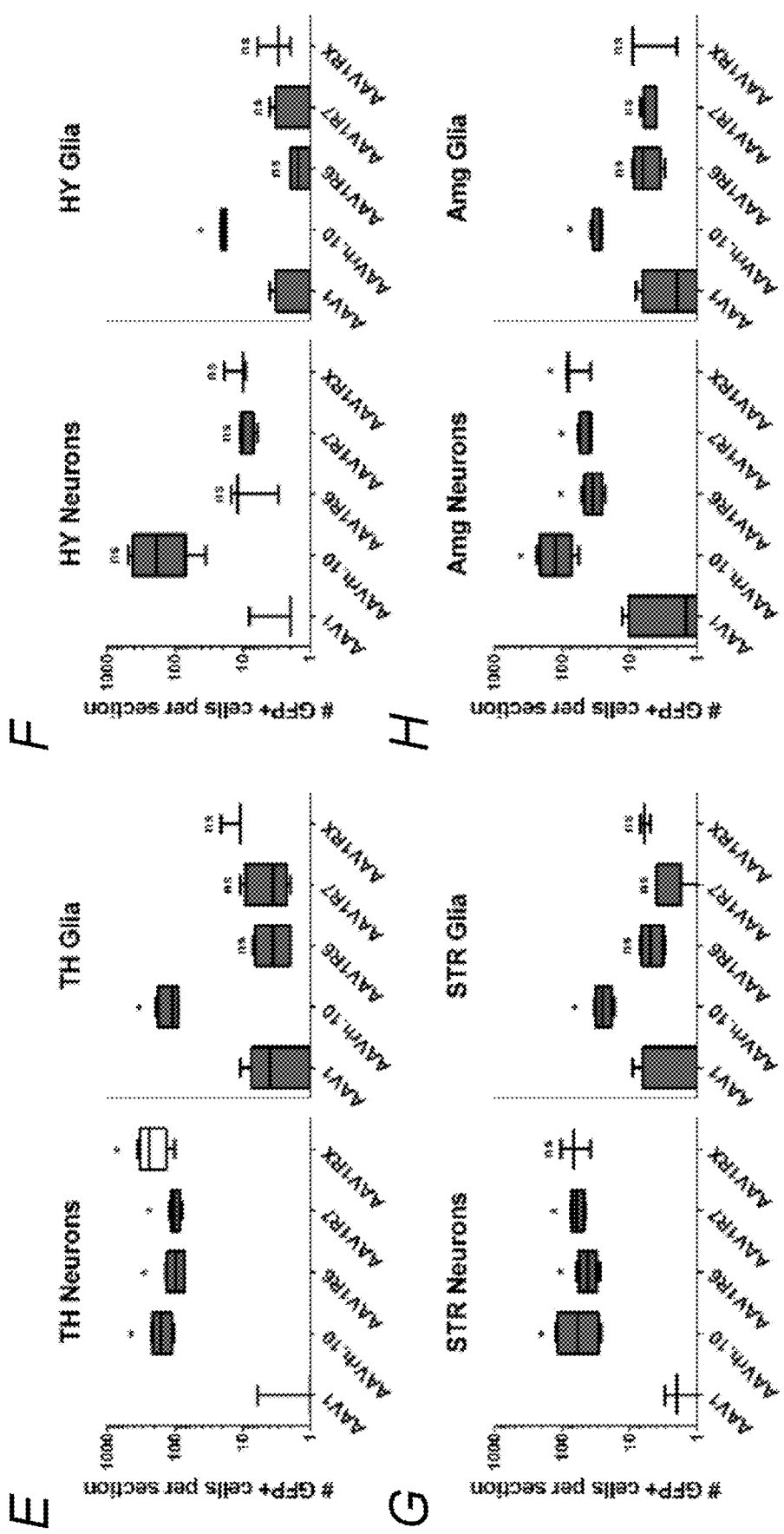

We then engineered a chimeric capsid by grafting the 8 amino acid residues from AAVrh.10 onto the AAV1 serotype, naming this chimera AAV1RX. We administered 6-8 week-old female C57/B16 mice with AAV1RX-CBh-scGFP vectors at a dose of $5\times10^{11}$ vg per mouse via tail vein injection. GFP reporter expression in the brain was assessed by immunostaining at 21 days post injection. As seen in FIG. 11H, AAV1RX transduces neurons within the motor cortex and cortical neurons across the entire cortex while demonstrating limited transduction of glia and reduced vascular transduction, as seen earlier with the chimeric capsids AAV1R6 and AAV1R7. Continuing this trend, numerous GFP+ pyramidal neurons are observed in the hippocampus along with an abundance of GFP+ granular cells in the dentate gyrus. Notably, GFP+ glial and endothelial cells in these regions are largely absent. In the thalamus, AAV1RX demonstrates robust neuronal transduction at levels comparable to AAV1R6 and AAV1R7 with modest transduction of glial and endothelial cells, albeit at levels higher than for other brain regions. In the hypothalamus, GFP+ neurons are sparse and few GFP+ glia and vascular endothelial cells are observed. Lastly, the preferentially neuronal transduction profile displayed by AAV1RX is also seen within the striatum (specifically, the caudate putamen) and amygdala (FIG. 11H). Quantitative analyses of these brain regions and comparisons to those seen for AAV1, AAVrh.10 and the chimeric AAV1R6 and AAV1R7 vectors suggest that this minimal footprint of 8 amino acid residues from AAVrh.10 is critical for crossing the BBB (FIG. 13).

AAV1R6, AAV1R7 and AAV1RX Mediate Low Transduction Levels and Biodistribution in Peripheral Tissues.

Figure 12:
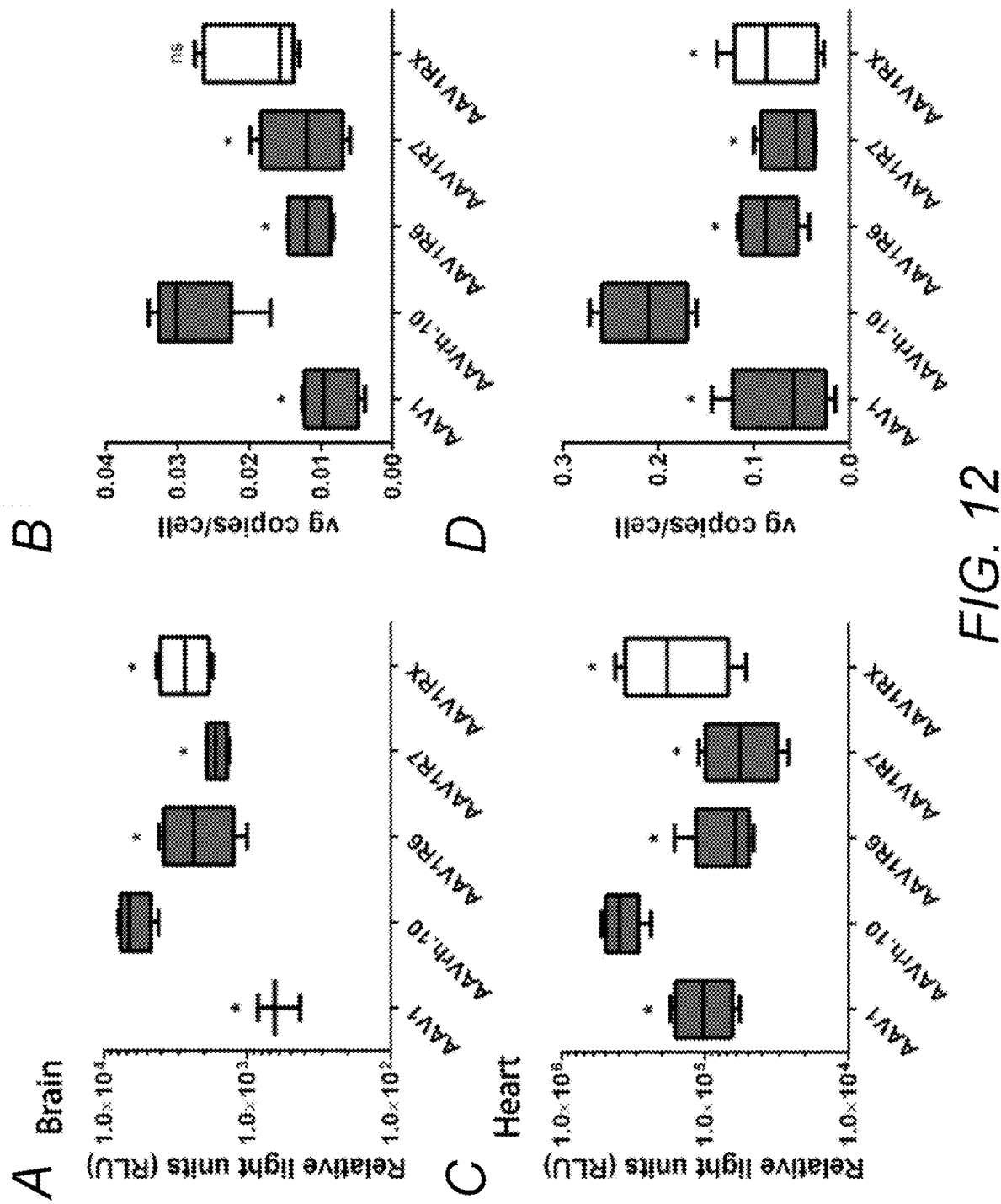
FIGS. 12A-12H. Peripheral tissue transduction and biodistribution of AAV1R6, AAV1R7 and AAV1RX following intravenous administration. Mice were injected via the tail vein with PBS or with either AAV1, AAVrh.10, AAV1R6, AAV1R7 or AAV1RX vectors packaging a CBA-Luc reporter transgene at a dose of $1\times10^{11}$ vg. At 2 weeks post-injection, luciferase reporter transgene expression levels (FIGS. 12A, 12C, 12E, 12G) and biodistribution of viral genome copies across various tissues (FIG. 12B, 12D, 12F, 12H) were quantified. Luciferase expression levels were normalized to grams of tissue lysate and are represented as relative light units. Vector genome (vg) copies are normalized to mouse lamin B (mLamB) as an endogenous housekeeping gene and are represented as vg copies per cell. Error bars represent standard deviation (n=3 for luciferase assays; n=4 for biodistribution). One-way ANOVA and an unpaired two-tailed T-test with Welch's correction for each group were carried out and significance relative to AAVrh.10 is shown. ns, not significant. *, P<0.05.
Figure 12:
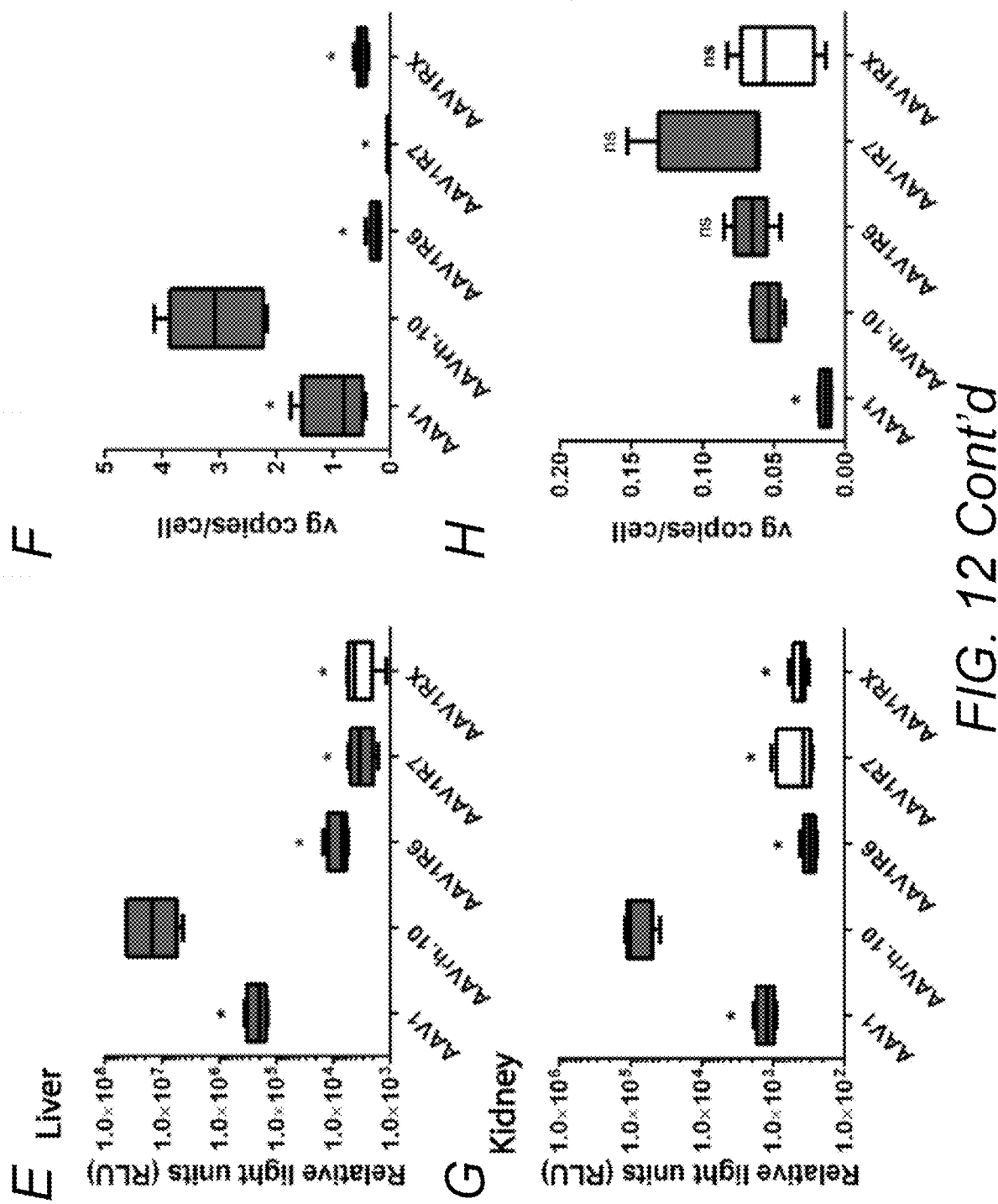

To carry out a comparative analysis of different chimeric capsids with parental serotypes, 6-8 week old female C57/B16 mice were injected via tail vein with either AAV1, AAVrh.10, AAV1R6, AAV1R7 or AAV1RX vectors packaging a single-stranded luciferase reporter transgene driven by a chicken beta actin promoter (ssCBA-Luc) at a dose of $1\times10^{11}$ vg per animal. At 2 weeks post injection, mice were sacrificed and tissues were harvested. Luciferase activity assays on tissue lysates as well as qPCR analyses to determine vector biodistribution were carried out (FIG. 12). All three chimeric vectors mediate higher luciferase transgene expression and a corresponding increase in viral genome copies, for each, is observed within the brain compared to AAV1 (FIGS. 12A and 12B). However, their transgene expression levels and viral genome copy numbers were ~2-to-3-fold lower in the brain compared to AAVrh.10, which were all found to be statistically significant, with the exception of AV1RX biodistribution (FIGS. 12A and 12B). Similar transduction levels and viral genome copy numbers were observed for AAV1R6, AAV1R7 and AAV1RX in the heart, comparable to those seen for AAV1, despite some variation in cardiac transduction levels observed for AAV1RX (FIGS. 12C and 12D). AAVrh.10 mediates ~2-4-fold higher cardiac luciferase expression and correspondingly ~2-fold higher viral genome copies in the heart compared to the other vectors (FIGS. 12C and 12D). As demonstrated by other groups, AAVrh.10 displayed several fold higher luciferase transgene expression levels and consistently high viral genome copies in the liver. In contrast, low to background levels of luciferase expression and significantly reduced viral genome copies were detected in the liver for AAV1, 1R6, 1R7 and 1RX (FIGS. 12E and 12F). It is noteworthy to mention that luciferase expression and a corresponding trend in viral genome copy numbers were detected for AAVrh.10 in the kidney (FIGS. 12G and 12H). Although the three chimeric vectors showed similar viral genome copy number levels, luciferase expression in the kidney was absent. Taken together, these data seem to suggest that the chimeric AAV1R6, 1R7 and 1RX vectors are de-targeted from the liver and may be cleared from the blood circulation by the kidney.

Following intravenous administration, we identified a subset of chimeric capsids capable of crossing the BBB and efficiently transducing the CNS. The ability to cross the BBB was found to inversely correlate with infectivity in cell culture and sensitivity to neuraminidase. Structural modeling and roadmap analysis further helped identify several key clusters of residues in AAVrh.10 that enable transport across the brain vasculature and widespread neuronal transduction. Subsequently, we were able to further narrow down the size of this footprint through a rational mutagenesis approach, which was then functionally validated in vivo. In conclusion, we have identified a minimal footprint from AAVrh.10 which, when grafted onto other AAV strains, permits transport across the BBB and enables a more targeted CNS transduction profile compared to AAVrh.10. Furthermore, the resulting capsids are detargeted from the brain vasculature, liver and other peripheral tissues. The functional mapping of this novel neurotropic footprint provides a roadmap for engineering synthetic AAV capsids for efficient CNS gene transfer with an improved safety profile.

AAV1 and AAVrh.10, the parental serotypes used to generate the chimeric capsid library in this study, are both non-human primate isolates that belong to two different clades—AAV1 belongs to cade A while AAVrh.10 falls within Clade E. Despite the evolutionary distance between them, they share -85% sequence homology between their Cap genes. AAV1 is known to recognize N-linked sialic acid (Sia) and the key residues composing the Sia recognition footprint on the AAV1 capsid have been recently reported. The current study identified 262N, 263G, 264T, 265S, 267G, 268S, 269T and 273T as key residues on the chimeric AAV1RX capsid, derived from AAVrh.10, that are essential for crossing the BBB. While none of the Sia contact residues for AAV1 are located within the chimeric 1RX footprint, the backbone carbonyl oxygen atoms of residues S268, D271, and N272 have been implicated in possibly stabilizing capsid-glycan interactions and increasing Sia binding affinity. Furthermore, residues at this position (D271 and N272) are located within the galactose-binding footprint on AAV9. Thus, the current study supports the notion that residues within VR-I are critical.

Alignment of the VP3 sequences of natural AAV isolates reveals that the 8 amino acid residues that confer the CNS phenotype to AAV1RX are conserved in AAVrh.8 and AAVrh.39, other neurotropic capsids in Clade E (FIG. 14). Similarly, AAV8 and AAVrh.43, also located within Clade E, demonstrate the ability to cross the BBB, albeit far less efficiently. Both possess 7 out of the 8 residues in this footprint; therefore, introducing the complete footprint onto these capsids will likely enhance their ability to cross the BBB.

Phenotypically, AAV1 and AAVrh.10 differ markedly in their ability to cross the BBB and transduce neurons and glia in the brain. When delivered intravenously, AAV1 demonstrates preferential uptake and transduction in vascular endothelial cells. In contrast, AAVrh.10 appears not only to be taken up by and transduce vascular endothelial cells, but also to traverse the vasculature and transduce underlying tissue such as the CNS or skeletal muscle. The current study identifies a minimum set of residues on the AAVrh.10 capsid that partially confers these traits to AAV1 capsids. While this minimal footprint on the AAV1RX chimera appears essential for traversing the BBB and transducing neurons, transduction in peripheral tissues such as the liver is markedly reduced, while cardiac expression remains similar to that of AAV1. These differences suggest that other structural domains on the AAVrh.10 capsid may play a role in imparting a systemic transduction profile. With regard to the brain parenchyma, it is important to note that after CNS entry, the post-entry transduction profile of AAV1RX is preferentially neuronal with decreased glial transduction compared to AAVrh.10. This can likely be attributed to the fact that the majority of the capsid is derived from AAV1, which is known to mediate a preferentially neuronal transduction following intracerebroventricular injections. It is also possible that the unknown mechanism by which 1RX crosses the BBB mediates preferential neuronal uptake or that additional motifs/amino acid residues on the AAVrh.10 capsid may mediate post-entry steps in glial transduction.

From a clinical perspective, capsids that can traverse the BBB, preferentially transduce neurons within the brain and that are simultaneously de-targeted from the liver may demonstrate an improved safety profile for CNS-targeted gene transfer applications from a systemic route of administration. Decreased vector uptake in peripheral organs, particularly the liver, could reduce the potential threat of hepatotoxicity, as evidenced by the transient elevation in transaminases in patient serum following systemic injection of certain AAV serotypes.

The AAV1R6/7/X vectors may be broadly used for global CNS gene transfer and in particular, for developing gene therapy strategies to treat neurological disorders such as Friedreich's Ataxia or spinal muscular atrophy.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |

TABLE 1-continued

| | GenBank Accession Number |
|---|---|
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

TABLE 2

AAV1R7 modifications in AAV serotypes 1, 2, 3, 6, 7, 8, 9, and rh10.

AAV1R7 Residue Changes

| AAV1 | AAV2 | AAV3 | AAV6 | AAV7 | AAV8 | AAV9 | AAVrh.10 |
|---|---|---|---|---|---|---|---|
| Q148P | H148P | Q148P | Q148P | P148P | P148P | Q148P | P148P |
| — | —151Q | —151Q | — | — | — | —151Q | — |
| E152R | V151R | Q152R | E152R | Q152R | R152R | Q152R | R152R |
| —153S | E152S | E153S | —153S | S153S | S153S | E153S | S153S |
| S157T | S158T | S158T | S157T | T158T | T158T | A158T | T158T |
| T162K | A163K | S163K | T162K | K163K | K163K | S163K | K163K |
| L188I | L189I | L189I | L188I | L189I | L189I | I189I | I189I |
| S205A | T206A | S206A | S205A | A206A | A206A | S206A | A206A |
| N223S | N224S | N224S | N223S | N224S | S224S | N224S | S224S |
| A224S | S225S | S225S | A224S | S225S | S225S | S225S | S225S |
| S262N | S263N | S263N | S262N | S263N | S263N | N263N | N263N |
| A263G | Q264G | Q264G | A263G | E264G | G264G | S264G | G264G |
| S264T | S265T | S265T | S264T | T265T | T265T | T265T | T265T |
| T265S | —266S | G266S | T265S | A266S | T266S | S266S | S266S |
| —267G | —267G | —267G | —267G | —267G | G267G | G267G | G267G |

TABLE 2-continued

AAV1R7 modifications in AAV serotypes 1, 2, 3, 6, 7, 8, 9, and rh10.
AAV1R7 Residue Changes

| AAV1 | AAV2 | AAV3 | AAV6 | AAV7 | AAV8 | AAV9 | AAVrh.10 |
|---|---|---|---|---|---|---|---|
| — | — | —268G | — | — | — | — | — |
| A267S | A269S | A269S | A267S | S269S | A269S | S269S | S269S |
| S268T | S270T | S270T | S268T | T270T | T270T | S270T | T270T |
| H272T | H274T | H274T | H272T | T274T | T274T | A274T | T274T |
| T326Q | Q328Q | Q328Q | T326Q | T328Q | Q328Q | D328Q | Q328Q |
| D328E | D330E | D330E | D328E | D330E | E330E | N330E | E330E |
| V330T | T332T | T332T | V330T | V332T | T332T | V332T | T332T |
| T331K | T333K | T333K | T331K | T333K | K333K | K333K | K333K |
| V341I | V343I | V343I | V341I | I343I | I343I | V343I | I343I |
| S345T | T347T | T347T | S345T | S347T | T347T | T347T | T347T |

*Numbering is relative to wild type.

TABLE 3

Amino acid residues and abbreviations.

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

REFERENCES

The following references are incorporated by reference herein in their entireties for all purposes.

1. Berns, K and Parrish, C (2007). Parvoviridae. Knipe D M, Howley P M, Griffin D E, Lamb R A, Martin M A, Roizman B, Straus S E (ed), *Fields Virol.* 5th ed, vol H., Lippincott Williams & Wilkins, Philadelphia, P A: pp 2437-2477.
2. Gao, G, Vandenberghe, L H, Alvira, M R, Lu, Y, Calcedo, R, Zhou, X, et al. (2004). Clades of Adeno-associated viruses are widely disseminated in human tissues. *J. Virol.* 78: 6381-8.
3. Gao, G, Alvira, M R, Somanathan, S, Lu, Y, Vandenberghe, L H, Rux, J J, et al. (2003). Adeno-associated viruses undergo substantial evolution in primates during natural infections. *Proc. Natl. Acad. Sci. U.S.A* 100: 6081-6086.
4. Agbandje-McKenna, M and Kleinschmidt, J (2011). AAV capsid structure and cell interactions. *Methods Mol. Biol.* 807: 47-92.
5. Madigan, V J and Asokan, A (2016). Engineering AAV receptor footprints for gene therapy. *Curr. Opin. Virol.* 18: 89-96.
6. Huang, L Y, Halder, S and Agbandje-McKenna, M (2014). Parvovirus glycan interactions. *Curr. Opin. Virol.* 7C: 108-118.
7. Kashiwakura, Y, Tamayose, K, Iwabuchi, K, Hirai, Y, Shimada, T, Matsumoto, K, et al. (2005). Hepatocyte Growth Factor Receptor Is a Coreceptor for Adeno-Associated Virus Type 2 Infection. *J. Virol.* 79: 609-614.
8. Weller, M L, Amomphimoltham, P, Schmidt, M, Wilson, P A, Gutkind, J S and Chiorini, J A (2010). Epidermal growth factor receptor is a co-receptor for adeno-associated virus 26 serotype 6. *Nat. Med.* 16: 662-4.
9. Di Pasquale, G, Davidson, B L, Stein, C S, Martins, I, Scudiero, D, Monks, A, et al. (2003). Identification of PDGFR as a receptor for AAV-5 transduction. *Nat. Med.* 9: 1306-12.
10. Asokan, A, Hamra, J B, Govindasamy, L, Agbandje-McKenna, M and Samulski, R J (2006). Adeno-associated virus type 2 contains an integrin alpha5beta1 binding domain essential for viral cell entry. *J. Virol.* 80: 8961-9.
11. Pillay, S, Meyer, N L, Puschnik, A S, Davulcu, O, Diep, J, Ishikawa, Y, et al. (2016). An essential receptor for adeno-associated virus infection. *Nature* 530: 108-112.
12. Murlidharan, G, Samulski, R J and Asokan, A (2014). Biology of adeno-associated viral vectors in the central nervous system. *Front. Mol. Neurosci.* 7: 1-9.
13. Murlidharan, G, Crowther, A, Reardon, R A, Song, J and Asokan, A (2016). Glymphatic fluid transport controls paravascular clearance of AAV vectors from the brain. *JCI Insight* 1: 1-11.
14. Ballabh, P, Braun, A and Nedergaard, M (2004). The blood-brain barrier: An overview: Structure, regulation, and clinical implications. *Neurobiol. Dis.* 16: 1-13.
15. Williams, D W, Eugenin, E A, Calderon, T M and Berman, J W (2012). Monocyte maturation, HIV susceptibility, and transmigration across the blood brain barrier are critical in HIV neuropathogenesis. *J Leukoc. Biol.* 91: 401-15.
16. Salinas, S, Schiavo, G and Kremer, E J (2010). A hitchhiker's guide to the nervous system: the complex journey of viruses and toxins. *Nat. Rev. Microbiol.* 8: 645-655.
17. Yang, B, Li, S, Wang, H, Guo, Y, Gessler, D J, Cao, C, et al. (2014). Global CNS transduction of adult mice by intravenously delivered rAAVrh.8 and rAAVrh.10 and nonhuman primates by rAAVrh.10. *Mol. Ther.* 22: 1299-1309.
18. Rosenberg, J B, Sondhi, D, Rubin, D G, Monette, S, Chen, A, Cram, S, et al. (2014). Comparative Efficacy and Safety of Multiple Routes of Direct CNS Administration of Adeno-Associated Virus Gene Transfer Vector Serotype rh.10 Expressing the Human Arylsulfatase A cDNA to Nonhuman Primates. *Hum. Gene Ther. Dev.* doi: 10.1089/humc.2013.239 [doi].

19. Gray, S J, Matagne, V, Bachaboina, L, Yadav, S, Ojeda, S R and Samulski, R J (2011). Preclinical differences of intravascular AAV9 delivery to neurons and glia: a comparative study of adult mice and nonhuman primates. *Mol. Ther.* 19: 1058-1069.
20. Zhang, H, Yang, B, Mu, X, Ahmed, S S, Su, Q, He, R, et al. (2011). Several rAAV vectors efficiently cross the blood-brain barrier and transduce neurons and astrocytes in the neonatal mouse central nervous system. *Mol. Ther.* 19: 1440-1448.
21. Cearley, C N, Vandenberghe, L H, Parente, M K, Carnish, E R, Wilson, J M and Wolfe, J H (2008). Expanded repertoire of AAV vector serotypes mediate unique patterns of transduction in mouse brain. *Mol. Ther.* 16: 1710-8.
22. Grieger, J C, Snowdy, S and Samulski, R J (2006). Separate Basic Region Motifs within the Adeno-Associated Virus Capsid Proteins Are Essential for Infectivity and Assembly. *J. Virol.* 80: 5199-5210.
23. Sonntag, F, Bleker, S, Leuchs, B, Fischer, R and Kleinschmidt, J A (2006). Adeno-associated virus type 2 capsids with externalized VP1/VP2 trafficking domains are generated prior to passage through the cytoplasm and are maintained until uncoating occurs in the nucleus. *J. Virol.* 80: 11040-11054.
24. Bowles, D E, McPhee, S W, Li, C, Gray, S J, Samulski, J J, Camp, A S, et al. (2012). Phase 1 gene therapy for Duchenne muscular dystrophy using a translational optimized AAV vector. *Mol. Ther.* 20: 443-455.
25. Li, C, Diprimio, N, Bowles, D E, Hirsch, M L, Monahan, P E, Asokan, A, et al. (2012). Single amino acid modification of adeno-associated virus capsid changes transduction and humoral immune profiles. *J. Virol.* 86: 7752-7759.
26. Bleker, S, Sonntag, F and Kleinschmidt, J A (2005). Mutational analysis of narrow pores at the fivefold symmetry axes of adeno-associated virus type 2 capsids reveals a dual role in genome packaging and activation of phospholipase A2 activity. *J. Virol.* 79: 2528-2540.
27. Wu, Z, Miller, E, Agbandje-McKenna, M and Samulski, R J (2006). Alpha2,3 and alpha2,6 N-linked sialic acids facilitate efficient binding and transduction by adeno-associated virus types 1 and 6. *J. Virol.* 80: 9093-103.
28. Huang, L-Y, Patel, A, Ng, R, Miller, E B, Halder, S, Mckenna, R, et al. Characterization of the Adeno-Associated Virus 1 and 6 Sialic Acid Binding Sitedoi:10.1128/JVI.00161-16.
29. Bell, C L, Gurda, B L, Vliet, K Van, Agbandje-McKenna, M and Wilson, J M (2012). Identification of the galactose binding domain of the AAV9 capsid. *J. Virol.* 86: 7326-7333.
30. Rosenberg, J B, Sondhi, D, Rubin, D G, Monette, S, Chen, A, Cram, S, et al. (2014). Comparative efficacy and safety of multiple routes of direct CNS administration of adeno-associated virus gene transfer vector serotype rh.10 expressing the human arylsulfatase A cDNA to nonhuman primates. *Hum. Gene Ther. Clin. Dev.* 25: 164-77.
31. Cearley, C N and Wolfe, J H (2006). Transduction characteristics of adeno-associated virus vectors expressing cap serotypes 7, 8, 9, and Rh10 in the mouse brain. *Mol. Ther.* 13: 528-37.
32. Hadaczek, P, Forsayeth, J, Mirek, H, Munson, K, Bringas, J, Pivirotto, P, et al. (2009). Transduction of nonhuman primate brain with adeno-*associated virus serotype* 1: vector trafficking and immune response. *Hum. Gene Ther.* 20: 225-237.
33. Chen, S, Kapturczak, M, Loiler, S A, Zolotukhin, S, Glushakova, O Y, Madsen, K M, et al. (2005). Efficient Transduction of Vascular Endothelial Cells with Recombinant Adeno-Associated Virus Serotype 1 and 5 Vectors. *Hum. Gene Ther.* 16: 235-247.
34. Pulicherla, N, Shen, S, Yadav, S, Debbink, K, Govindasamy, L, Agbandje-McKenna, M, et al. (2011). Engineering Liver-detargeted AAV9 Vectors for Cardiac and Musculoskeletal Gene Transfer. *Mol. Ther.* 19: 1070-1078.
35. Asokan, A, Conway, J C, Phillips, J L, Li, C, Hegge, J, Sinnott, R, et al. (2010). Reengineering a receptor footprint of adeno-associated virus enables selective and systemic gene transfer to muscle. *Nat. Biotechnol.* 28: 79-82.
36. Nathwani, A C, Reiss, U M, Tuddenham, E G D, Rosales, C, Chowdary, P, McIntosh, J, et al. (2014). Long-term safety and efficacy of factor IX gene therapy in hemophilia B. *N. Engl. J Med.* 371: 1994-2004.
37. Mingozzi, F and High, K A (2013). Immune responses to AAV vectors: overcoming barriers to successful gene therapy. *Blood* 122: 23-36.
38. Kumar, S, Stecher, G and Tamura, K (2016). MEGA7: Molecular Evolutionary Genetics Analysis Version 7.0 for Bigger Datasets. *Mol. Biol.* Evol. 33: 1870-4.
39. Saitou, N and Nei, M (1987). The neighbor-joining method: a new method for reconstructing phylogenetic trees. *Mol. Biol. Evol.* 4: 406-25.
40. Felsenstein, J (1985). CONFIDENCE LIMITS ON PHYLOGENIES: AN APPROACH USING THE BOOTSTRAP. *Evolution* (NY). 39: 783-791.
41. Murlidharan, G, Sakamoto, K, Rao, L, Corriher, T, Wang, D, Gao, G, et al. (2016). CNS-restricted Transduction and CRISPR/Cas9-mediated Gene Deletion with an Engineered AAV Vector. *Mol. Ther.—Nucleic Acids* 5: e338.
42. Lein, E S, Hawrylycz, M J, Ao, N, Ayres, M, Bensinger, A, Bernard, A, et al. (2007). Genome-wide atlas of gene expression in the adult mouse brain. *Nature* 445: 168-176.
43. Miller, E B, Gurda-Whitaker, B, Govindasamy, L, McKenna, R, Zolotukhin, S, Muzyczka N, et al. (2006). Production, purification and preliminary X-ray crystallographic studies of adeno-associated virus serotype 1. *Acta Crystallogr. Sect. F Struct. Biol. Cryst. Commun.* 62: 1271-1274.
44. Bordoli, L, Kiefer, F, Arnold, K, Benkert, P, Battey, J and Schwede, T (2008). Protein structure homology modeling using SWISS-MODEL workspace. *Nat. Protoc.* 4: 1-13.
45. Nam, H J, Lane, M D, Padron, E, Gurda, B, McKenna, R, Kohlbrenner, E, et al. (2007). Structure of adeno-associated virus serotype 8, a gene therapy vector. *J. Virol.* 81: 12260-12271.
46. Krissinel, E and Henrick, K (2004). Secondary-structure matching (SSM), a new tool for fast protein structure alignment in three dimensions. *Acta Crystallogr. Sect. D Biol. Crystallogr.* 60: 2256-2268.
47. Emsley, P, Lohkamp, B, Scott, W G and Cowtan, K (2010). Features and development of Coot. *Acta Crystallogr. D. Biol. Crystallogr.* 66: 486-501.
48. Carrillo-Tripp, M, Shepherd, C M, Borelli, I A, Venkataraman, S, Lander, G, Natarajan, P, et al. (2009). VIPERdb2: an enhanced and web API enabled relational database for structural virology. *Nucleic Acids Res.* 37: D436-42.
49. Xiao, C and Rossmann, M G (2007). Interpretation of electron density with stereographic roadmap projections. *J. Struct. Biol.* 158: 182-187.

The invention claimed is:

1. An adeno-associated virus (AAV) capsid protein, wherein the AAV capsid protein comprises the following modifications, wherein the amino acids are numbered according to the amino acid sequence of SEQ ID NO:1:
   (i) S262N, A263G, S264T, T265S, and A267G; and
   (ii) an insertion of a single amino acid,
wherein the amino acid sequence of the capsid protein is the amino acid sequence of SEQ ID NO:16 or SEQ ID NO:23.

2. An adeno-associated virus (AAV) vector comprising the AAV capsid protein of claim 1.

3. The AAV vector of claim 2, further comprising:
   a nucleic acid molecule, comprising at least one terminal repeat sequence, wherein the nucleic acid molecule is encapsidated by the AAV capsid protein.

4. The AAV virus vector of claim 3, wherein the nucleic acid molecule further comprises a sequence encoding a therapeutic protein or therapeutic RNA.

5. A pharmaceutical composition comprising the virus vector of claim 3.

6. A method of introducing a nucleic acid molecule into a cell, comprising contacting the cell with the pharmaceutical composition of claim 5.

7. The method of any of claim 6, wherein the cell is a neuronal cell.

8. A method of treating a neurological disorder or defect in a subject, wherein the method comprises administering to the subject the pharmaceutical composition of claim 5.

9. A method of introducing a nucleic acid molecule into a cell, comprising contacting the cell with the AAV virus vector of claim 3.

10. The method of claim 9, wherein the cell is a neuronal cell.

11. A method of treating a neurological disorder or defect in a subject, wherein the method comprises administering to the subject the virus vector of claim 3.

\* \* \* \* \*

UNITED STATES PATENT AND TRADEMARK OFFICE
CERTIFICATE OF CORRECTION

| | |
|---|---|
| PATENT NO. | : 11,905,312 B2 |
| APPLICATION NO. | : 16/485094 |
| DATED | : February 20, 2024 |
| INVENTOR(S) | : Asokan et al. |

Page 1 of 2

It is certified that error appears in the above-identified patent and that said Letters Patent is hereby corrected as shown below:

In the Specification

Column 8, Line 5: Please correct "10%, +5%, +1%, +0.5%," to read --±10%, ±5%, ±1%, ±0.5%,--

Column 14, Line 14: Please correct "V3411" to read --V341I--

Column 14, Line 19: Please correct "5205" to read --S205--

Column 25, Lines 48-49: Please remove the paragraph break between "vector." and "In particular"

Column 30, Line 2: Please correct "β-15" to read --P-15--

Column 32, Line 2: Please correct "(B-globin)" to read --(β-globin)--

Column 32, Line 4: Please correct "(B-interferon)" to read --(β-interferon)--

Column 32, Line 28: Please correct "(al-antitrypsin)" to read --(α1-antitrypsin)--

Column 32, Line 63: Please correct "SCAT" to read --SCA1--

Column 35, Line 63: Please correct "interleukin-la" to read --interleukin-1α--

Column 36, Line 50: Please correct "10 infectious" to read --$10^3$ infectious--

Column 36, Lines 50-51: Please correct "105 infectious" to read --$10^5$ infectious--

Column 37, Line 21: Please correct "102 to about $10^8$ cells or at least about 103" to read --$10^2$ to about $10^8$ cells or at least about $10^3$--

Signed and Sealed this
Sixteenth Day of July, 2024

Katherine Kelly Vidal
*Director of the United States Patent and Trademark Office*

CERTIFICATE OF CORRECTION (continued)
U.S. Pat. No. 11,905,312 B2

Column 45, Line 2: Please correct "SchrOdingerLLC" to read --SchrÖdingerLLC--

Column 48, Line 66: Please correct "1891" to read --189I--

Column 49, Line 35: Please correct "3431" to read --343I--

Column 49, Line 36: Please correct "R-strand" to read --β-strand--

Column 49, Line 51: Please correct "3431" to read --343I--

Column 50, Lines 56-57: Please correct "-2-4-fold" to read --~2-4-fold--

Column 50, Line 58: Please correct "-2-fold" to read --~2-fold--

Column 51, Line 33: Please correct "-85%" to read --~85%--

In the Claims

Column 195, Line 15, Claim 1: Please correct "modifications," to read --mutations,--

SEQUENCE LISTING

<160> NUMBER OF SEQ ID NOS: 51

<210> SEQ ID NO 1
<211> LENGTH: 736
<212> TYPE: PRT
<213> ORGANISM: Adeno-associated virus

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365
```

-continued

```
Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: Adeno-associated virus

<400> SEQUENCE: 2

Met Ala Ala Asp Gly Tyr Leu Pro Asp Trp Leu Glu Asp Thr Leu Ser
1               5                   10                  15
```

```
Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430
```

```
Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Adeno-associated virus

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80
```

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

```
Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Adeno-associated virus

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

```
Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
    435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
    515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560
```

```
Thr Asp Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 5
<211> LENGTH: 737
<212> TYPE: PRT
<213> ORGANISM: Adeno-associated virus

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205
```

-continued

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 6
<211> LENGTH: 738
<212> TYPE: PRT
<213> ORGANISM: Adeno-associated virus

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

-continued

```
Leu Tyr Lys Gln Ile Ser Asn Gly Thr Ser Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
```

-continued

```
            675                 680                 685
Leu Gln Lys Glu Asn Ser Lys Arg Trp Asn Pro Glu Ile Gln Tyr Thr
            690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 7
<211> LENGTH: 736
<212> TYPE: PRT
<213> ORGANISM: Adeno-associated virus

<400> SEQUENCE: 7

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
```

```
            305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Phe Pro
                        355                 360                 365
        Ala Asp Val Phe Met Ile Pro Gln Tyr Gly Tyr Leu Thr Leu Asn Asp
                        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Ser
                        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
        Tyr Gly Gln Val Ala Thr Asn His Gln Ser Ala Gln Ala Gln Ala Gln
                        580                 585                 590
        Thr Gly Trp Val Gln Asn Gln Gly Ile Leu Pro Gly Met Val Trp Gln
                        595                 600                 605
        Asp Arg Asp Val Tyr Leu Gln Gly Pro Ile Trp Ala Lys Ile Pro His
                        610                 615                 620
        Thr Asp Gly Asn Phe His Pro Ser Pro Leu Met Gly Gly Phe Gly Met
        625                 630                 635                 640
        Lys His Pro Pro Pro Gln Ile Leu Ile Lys Asn Thr Pro Val Pro Ala
                        645                 650                 655
        Asp Pro Pro Thr Ala Phe Asn Lys Asp Lys Leu Asn Ser Phe Ile Thr
                        660                 665                 670
        Gln Tyr Ser Thr Gly Gln Val Ser Val Glu Ile Glu Trp Glu Leu Gln
                        675                 680                 685
        Lys Glu Asn Ser Lys Arg Trp Asn Pro Glu Ile Gln Tyr Thr Ser Asn
                        690                 695                 700
        Tyr Tyr Lys Ser Asn Asn Val Glu Phe Ala Val Asn Thr Glu Gly Val
        705                 710                 715                 720
        Tyr Ser Glu Pro Arg Pro Ile Gly Thr Arg Tyr Leu Thr Arg Asn Leu
                        725                 730                 735
```

<210> SEQ ID NO 8
<211> LENGTH: 738
<212> TYPE: PRT
<213> ORGANISM: Adeno-associated virus

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn

```
                    370                 375                 380
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 9
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV1RX
```

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415
```

Phe Glu Glu Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Asn
            435                 440                 445

Arg Thr Gln Asn Gln Ser Gly Ser Ala Gln Asn Lys Asp Leu Leu Phe
        450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Glu Asp Lys Phe Phe Pro Met Ser Gly Val Met Ile Phe
    530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Phe Gln Ser Ser Ser Thr Asp Pro
            580                 585                 590

Ala Thr Gly Asp Val His Ala Met Gly Ala Leu Pro Gly Met Val Trp
        595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys Asn Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu

<210> SEQ ID NO 10
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV2RX

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

```
Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70              75                  80

Arg Gln Leu Asp Ser Gly Asp Asn Pro Tyr Leu Lys Tyr Asn His Ala
                 85              90                  95

Asp Ala Glu Phe Gln Glu Arg Leu Lys Glu Asp Thr Ser Phe Gly Gly
                100             105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
                210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

His Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Gln Asn Asp Gly Thr Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Val Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445
```

```
Arg Thr Asn Thr Pro Ser Gly Thr Thr Gln Ser Arg Leu Gln Phe
    450                 455                 460

Ser Gln Ala Gly Ala Ser Asp Ile Arg Asp Gln Ser Arg Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
            515                 520                 525

Lys Asp Asp Glu Glu Lys Phe Phe Pro Gln Ser Gly Val Leu Ile Phe
530                 535                 540

Gly Lys Gln Gly Ser Glu Lys Thr Asn Val Asp Ile Glu Lys Val Met
545                 550                 555                 560

Ile Thr Asp Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
                580                 585                 590

Ala Thr Ala Asp Val Asn Thr Gln Gly Val Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Ser Thr Thr Phe Ser Ala Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 11
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV3RX

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60
```

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Ile Leu Glu Pro
    115                 120                 125

Leu Gly Leu Val Glu Glu Ala Lys Thr Ala Pro Gly Lys Lys Arg
130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Ser Phe Lys Leu Phe Asn Ile
305                 310                 315                 320

Gln Val Lys Glu Val Thr Gln Asn Asp Gly Thr Thr Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Gly Thr Thr Ser Gly Thr Thr Asn Gln Ser Arg Leu Leu
    450                 455                 460

Phe Ser Gln Ala Gly Pro Gln Ser Met Ser Leu Gln Ala Arg Asn Trp
465                 470                 475                 480

Leu Pro Gly Pro Cys Tyr Arg Gln Gln Arg Leu Ser Lys Thr Ala Asn 485                 490                 495
Asp Asn Asn Asn Ser Asn Phe Pro Trp Thr Ala Ala Ser Lys Tyr His
                    500                 505                 510

Leu Asn Gly Arg Asp Ser Leu Val Asn Pro Gly Pro Ala Met Ala Ser
                515                 520                 525

His Lys Asp Asp Glu Lys Phe Phe Pro Met His Gly Asn Leu Ile
    530                 535                 540

Phe Gly Lys Glu Gly Thr Thr Ala Ser Asn Ala Glu Leu Asp Asn Val
545                 550                 555                 560

Met Ile Thr Asp Glu Glu Glu Ile Arg Thr Thr Asn Pro Val Ala Thr
                565                 570                 575

Glu Gln Tyr Gly Thr Val Ala Asn Asn Leu Gln Ser Ser Asn Thr Ala
                580                 585                 590

Pro Thr Thr Arg Thr Val Asn Asp Gln Gly Ala Leu Pro Gly Met Val
                595                 600                 605

Trp Gln Asp Arg Asp Val Tyr Leu Gln Gly Pro Ile Trp Ala Lys Ile
610                 615                 620

Pro His Thr Asp Gly His Phe His Pro Ser Pro Leu Met Gly Gly Phe
625                 630                 635                 640

Gly Leu Lys His Pro Pro Pro Gln Ile Met Ile Lys Asn Thr Pro Val
                645                 650                 655

Pro Ala Asn Pro Pro Thr Thr Phe Ser Pro Ala Lys Phe Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
            690                 695                 700

Ser Asn Tyr Asn Lys Ser Val Asn Val Asp Phe Thr Val Asp Thr Asn
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 12
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV6RX

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly

-continued

```
            100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
            130                 135             140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Thr Pro Ala Ala Val Gly Pro Thr Thr Met Ala Ser Gly Gly Gly
                195                 200                 205
Ala Pro Met Ala Asp Asn Asn Glu Gly Ala Asp Gly Val Gly Asn Ala
            210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
                260                 265                 270
His Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Val Gln Val Phe Ser Asp Ser Glu Tyr Gln Leu
                340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Asn
                435                 440                 445
Arg Thr Gln Asn Gln Ser Gly Ser Ala Gln Asn Lys Asp Leu Leu Phe
            450                 455                 460
Ser Arg Gly Ser Pro Ala Gly Met Ser Val Gln Pro Lys Asn Trp Leu
465                 470                 475                 480
Pro Gly Pro Cys Tyr Arg Gln Gln Arg Val Ser Lys Thr Lys Thr Asp
                485                 490                 495
Asn Asn Asn Ser Asn Phe Thr Trp Thr Gly Ala Ser Lys Tyr Asn Leu
                500                 505                 510
Asn Gly Arg Glu Ser Ile Ile Asn Pro Gly Thr Ala Met Ala Ser His
            515                 520                 525
```

```
Lys Asp Asp Lys Asp Lys Phe Phe Pro Met Ser Gly Val Met Ile Phe
            530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Val Gln Tyr Thr Ser
690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu

<210> SEQ ID NO 13
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV7RX

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140
```

```
Pro Val Glu Pro Ser Pro Gln Arg Ser Pro Asp Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
        210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Lys Leu Arg Phe Lys Leu Phe Asn
305                 310                 315                 320

Ile Gln Val Lys Glu Val Thr Thr Asn Asp Gly Val Thr Thr Ile Ala
                325                 330                 335

Asn Asn Leu Thr Ser Thr Ile Gln Val Phe Ser Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Ser Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ala Arg Thr Gln Ser Asn Pro Gly Gly Thr Ala Gly Asn Arg Glu Leu
        450                 455                 460

Gln Phe Tyr Gln Gly Gly Pro Ser Thr Met Ala Glu Gln Ala Lys Asn
465                 470                 475                 480

Trp Leu Pro Gly Pro Cys Phe Arg Gln Gln Arg Val Ser Lys Thr Leu
            485                 490                 495

Asp Gln Asn Asn Asn Ser Asn Phe Ala Trp Thr Gly Ala Thr Lys Tyr
            500                 505                 510

His Leu Asn Gly Arg Asn Ser Leu Val Asn Pro Gly Val Ala Met Ala
        515                 520                 525

Thr His Lys Asp Asp Glu Asp Arg Phe Phe Pro Ser Ser Gly Val Leu
        530                 535                 540

Ile Phe Gly Lys Thr Gly Ala Thr Asn Lys Thr Thr Leu Glu Asn Val
545                 550                 555                 560
```

```
Leu Met Thr Asn Glu Glu Ile Arg Pro Thr Asn Pro Val Ala Thr
                565                 570                 575

Glu Glu Tyr Gly Ile Val Ser Ser Asn Leu Gln Ala Ala Asn Thr Ala
            580                 585                 590

Ala Gln Thr Gln Val Val Asn Asn Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asn Pro Pro Glu Val Phe Thr Pro Ala Lys Phe Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Phe Glu Lys Gln Thr Gly Val Asp Phe Ala Val Asp Ser Gln
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 14
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV8RX

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

```
Thr Gly Asp Ser Glu Ser Val Pro Asp Pro Gln Pro Leu Gly Glu Pro
                180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
```

```
                    595                 600                 605
Trp Gln Asn Arg Asp Val Tyr Leu Gln Gly Pro Ile Trp Ala Lys Ile
                610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
                660                 665                 670
Ile Thr Gln Tyr Ser Thr Gly Gln Val Ser Val Glu Ile Glu Trp Glu
                675                 680                 685
Leu Gln Lys Glu Asn Ser Lys Arg Trp Asn Pro Glu Ile Gln Tyr Thr
                690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 15
<211> LENGTH: 736
<212> TYPE: PRT
<213> ORGANISM: Artificial Sequence
<220> FEATURE:
<223> OTHER INFORMATION: Synthetically constructed adeno-associated
      virus capsid protein AAV9RX

<400> SEQUENCE: 15

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
```

-continued

```
            210                 215                 220
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ser Thr Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640
```

-continued

```
Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV1R.6

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
```

-continued

```
                260                 265                 270
Asn Thr Tyr Phe Gly Tyr Ser Thr Pro Trp Gly Tyr Phe Asp Phe Asn
                    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Thr Phe Ser Tyr
                    405                 410                 415

Thr Phe Glu Glu Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Asn Arg Thr Gln Asn Gln Ser Gly Ser Ala Gln Asn Lys Asp Leu Leu
    450                 455                 460

Phe Ser Arg Gly Ser Pro Ala Gly Met Ser Val Gln Pro Lys Asn Trp
465                 470                 475                 480

Leu Pro Gly Pro Cys Tyr Arg Gln Gln Arg Val Ser Lys Thr Lys Thr
                    485                 490                 495

Asp Asn Asn Asn Ser Asn Phe Thr Trp Thr Gly Ala Ser Lys Tyr Asn
            500                 505                 510

Leu Asn Gly Arg Glu Ser Ile Ile Asn Pro Gly Thr Ala Met Ala Ser
        515                 520                 525

His Lys Asp Asp Glu Asp Lys Phe Phe Pro Met Ser Gly Val Met Ile
    530                 535                 540

Phe Gly Lys Glu Ser Ala Gly Ala Ser Asn Thr Ala Leu Asp Asn Val
545                 550                 555                 560

Met Ile Thr Asp Glu Glu Glu Ile Lys Ala Thr Asn Pro Val Ala Thr
                    565                 570                 575

Glu Arg Phe Gly Thr Val Ala Val Asn Phe Gln Ser Ser Ser Thr Asp
            580                 585                 590

Pro Ala Thr Gly Asp Val His Ala Met Gly Ala Leu Pro Gly Met Val
        595                 600                 605

Trp Gln Asp Arg Asp Val Tyr Leu Gln Gly Pro Ile Trp Ala Lys Ile
    610                 615                 620

Pro His Thr Asp Gly His Phe His Pro Ser Pro Leu Met Gly Gly Phe
625                 630                 635                 640

Gly Leu Lys Asn Pro Pro Gln Ile Leu Ile Lys Asn Thr Pro Val
                    645                 650                 655

Pro Ala Asn Pro Pro Ala Glu Phe Ser Ala Thr Lys Phe Ala Ser Phe
            660                 665                 670

Ile Thr Gln Tyr Ser Thr Gly Gln Val Ser Val Glu Ile Glu Trp Glu
        675                 680                 685
```

-continued

```
Leu Gln Lys Glu Asn Ser Lys Arg Trp Asn Pro Glu Val Gln Tyr Thr
        690                 695                 700
Ser Asn Tyr Ala Lys Ser Ala Asn Val Asp Phe Thr Val Asp Asn Asn
705                 710                 715                 720
Gly Leu Tyr Thr Glu Pro Arg Pro Ile Gly Thr Arg Tyr Leu Thr Arg
                725                 730                 735
Pro Leu

<210> SEQ ID NO 17
<211> LENGTH: 739
<212> TYPE: PRT
<213> ORGANISM: Artificial Sequence
<220> FEATURE:
<223> OTHER INFORMATION: Synthetically constructed adeno-associated
      virus capsid protein AAV2R.6

<400> SEQUENCE: 17

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu Pro Ser Pro Gln Arg Ser Glu Pro Asp Ser Ser Thr Gly
145                 150                 155                 160
Thr Gly Lys Lys Gly Gln Gln Pro Ala Arg Lys Arg Leu Asn Phe Gly
                165                 170                 175
Gln Thr Gly Asp Ala Asp Ser Val Pro Asp Pro Gln Pro Leu Gly Gln
            180                 185                 190
Pro Pro Ala Ala Pro Ser Gly Leu Gly Thr Asn Thr Met Ala Thr Gly
        195                 200                 205
Ser Gly Ala Pro Met Ala Asp Asn Asn Glu Gly Ala Asp Gly Val Gly
    210                 215                 220
Asn Ser Ser Gly Asn Trp His Cys Asp Ser Thr Trp Met Gly Asp Arg
225                 230                 235                 240
Val Ile Thr Thr Ser Thr Arg Thr Trp Ala Leu Pro Thr Tyr Asn Asn
                245                 250                 255
His Leu Tyr Lys Gln Ile Ser Asn Gly Thr Ser Gly Gly Ser Thr Asn
            260                 265                 270
Asp Asn Thr Tyr Phe Gly Tyr Ser Thr Pro Trp Gly Tyr Phe Asp Phe
        275                 280                 285
Asn Arg Phe His Cys His Phe Ser Pro Arg Asp Trp Gln Arg Leu Ile
    290                 295                 300
```

-continued

```
Asn Asn Asn Trp Gly Phe Arg Pro Lys Arg Leu Asn Phe Lys Leu Phe
305                 310                 315                 320

Asn Ile Gln Val Lys Glu Val Thr Gln Asn Gly Thr Lys Thr Ile
                325                 330                 335

Ala Asn Asn Leu Thr Ser Thr Ile Gln Val Phe Thr Asp Ser Glu Tyr
            340                 345                 350

Gln Leu Pro Tyr Val Leu Gly Ser Ala His Gln Gly Cys Leu Pro Pro
                355                 360                 365

Phe Pro Ala Asp Val Phe Met Val Pro Gln Tyr Gly Tyr Leu Thr Leu
370                 375                 380

Asn Asn Gly Ser Gln Ala Val Gly Arg Ser Ser Phe Tyr Cys Leu Glu
385                 390                 395                 400

Tyr Phe Pro Ser Gln Met Leu Arg Thr Gly Asn Asn Phe Thr Phe Ser
                405                 410                 415

Tyr Thr Phe Glu Asp Val Pro Phe His Ser Ser Tyr Ala His Ser Gln
                420                 425                 430

Ser Leu Asp Arg Leu Met Asn Pro Leu Ile Asp Gln Tyr Leu Tyr Tyr
            435                 440                 445

Leu Ser Arg Thr Asn Thr Pro Ser Gly Thr Thr Thr Gln Ser Arg Leu
450                 455                 460

Gln Phe Ser Gln Ala Gly Ala Ser Asp Ile Arg Asp Gln Ser Arg Asn
465                 470                 475                 480

Trp Leu Pro Gly Pro Cys Tyr Arg Gln Gln Arg Val Ser Lys Thr Ser
                485                 490                 495

Ala Asp Asn Asn Asn Ser Glu Tyr Ser Trp Thr Gly Ala Thr Lys Tyr
                500                 505                 510

His Leu Asn Gly Arg Asp Ser Leu Val Asn Pro Gly Pro Ala Met Ala
            515                 520                 525

Ser His Lys Asp Asp Glu Glu Lys Phe Phe Pro Gln Ser Gly Val Leu
            530                 535                 540

Ile Phe Gly Lys Gln Gly Ser Glu Lys Thr Asn Val Asp Ile Glu Lys
545                 550                 555                 560

Val Met Ile Thr Asp Glu Glu Ile Arg Thr Thr Asn Pro Val Ala
                565                 570                 575

Thr Glu Gln Tyr Gly Ser Val Ser Thr Asn Leu Gln Arg Gly Asn Arg
                580                 585                 590

Gln Ala Ala Thr Ala Asp Val Asn Thr Gln Gly Val Leu Pro Gly Met
            595                 600                 605

Val Trp Gln Asp Arg Asp Val Tyr Leu Gln Gly Pro Ile Trp Ala Lys
            610                 615                 620

Ile Pro His Thr Asp Gly His Phe His Pro Ser Pro Leu Met Gly Gly
625                 630                 635                 640

Phe Gly Leu Lys His Pro Pro Pro Gln Ile Leu Ile Lys Asn Thr Pro
                645                 650                 655

Val Pro Ala Asn Pro Ser Thr Thr Phe Ser Ala Ala Lys Phe Ala Ser
                660                 665                 670

Phe Ile Thr Gln Tyr Ser Thr Gly Gln Val Ser Val Glu Ile Glu Trp
                675                 680                 685

Glu Leu Gln Lys Glu Asn Ser Lys Arg Trp Asn Pro Glu Ile Gln Tyr
            690                 695                 700

Thr Ser Asn Tyr Asn Lys Ser Val Asn Val Asp Phe Thr Val Asp Thr
705                 710                 715                 720
```

```
Asn Gly Val Tyr Ser Glu Pro Arg Pro Ile Gly Thr Arg Tyr Leu Thr
                725                 730                 735

Arg Asn Leu

<210> SEQ ID NO 18
<211> LENGTH: 739
<212> TYPE: PRT
<213> ORGANISM: Artificial Sequence
<220> FEATURE:
<223> OTHER INFORMATION: Synthetically constructed adeno-associated
      virus capsid protein AAV3R.6

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Pro Ser Pro Gln Glu Ser Pro Asp Ser Ser Thr Gly Val
145                 150                 155                 160

Gly Lys Lys Gly Lys Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Thr Ser Leu Gly Ser Asn Thr Met Ala Ser Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Lys Leu Ser Phe Lys Leu Phe Asn
305                 310                 315                 320

Ile Gln Val Lys Glu Val Thr Gln Asn Glu Gly Thr Lys Thr Ile Ala
                325                 330                 335
```

-continued

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Val Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Asn Arg Thr Gln Gly Thr Thr Ser Gly Thr Thr Asn Gln Ser Arg Leu
450                 455                 460

Leu Phe Ser Gln Ala Gly Pro Gln Ser Met Ser Leu Gln Ala Arg Asn
465                 470                 475                 480

Trp Leu Pro Gly Pro Cys Tyr Arg Gln Gln Arg Leu Ser Lys Thr Ala
                485                 490                 495

Asn Asp Asn Asn Asn Ser Asn Phe Pro Trp Thr Ala Ala Ser Lys Tyr
            500                 505                 510

His Leu Asn Gly Arg Asp Ser Leu Val Asn Pro Gly Pro Ala Met Ala
        515                 520                 525

Ser His Lys Asp Asp Glu Glu Lys Phe Phe Pro Met His Gly Asn Leu
530                 535                 540

Ile Phe Gly Lys Glu Gly Thr Thr Ala Ser Asn Ala Glu Leu Asp Asn
545                 550                 555                 560

Val Met Ile Thr Asp Glu Glu Ile Arg Thr Thr Asn Pro Val Ala
                565                 570                 575

Thr Glu Gln Tyr Gly Thr Val Ala Asn Asn Leu Gln Ser Ser Asn Thr
            580                 585                 590

Ala Pro Thr Thr Arg Thr Val Asn Asp Gln Gly Ala Leu Pro Gly Met
        595                 600                 605

Val Trp Gln Asp Arg Asp Val Tyr Leu Gln Gly Pro Ile Trp Ala Lys
610                 615                 620

Ile Pro His Thr Asp Gly His Phe His Pro Ser Pro Leu Met Gly Gly
625                 630                 635                 640

Phe Gly Leu Lys His Pro Pro Pro Gln Ile Met Ile Lys Asn Thr Pro
                645                 650                 655

Val Pro Ala Asn Pro Pro Thr Thr Phe Ser Pro Ala Lys Phe Ala Ser
            660                 665                 670

Phe Ile Thr Gln Tyr Ser Thr Gly Gln Val Ser Val Glu Ile Glu Trp
        675                 680                 685

Glu Leu Gln Lys Glu Asn Ser Lys Arg Trp Asn Pro Glu Ile Gln Tyr
690                 695                 700

Thr Ser Asn Tyr Asn Lys Ser Val Asn Val Asp Phe Thr Val Asp Thr
705                 710                 715                 720

Asn Gly Val Tyr Ser Glu Pro Arg Pro Ile Gly Thr Arg Tyr Leu Thr
                725                 730                 735

Arg Asn Leu

<210> SEQ ID NO 19

```
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV6R.6

<400> SEQUENCE: 19
```

| Met | Ala | Ala | Asp | Gly | Tyr | Leu | Pro | Asp | Trp | Leu | Glu | Asp | Asn | Leu | Ser |
|---|---|---|---|---|---|---|---|---|---|---|---|---|---|---|---|
| 1 | | | | 5 | | | | | 10 | | | | | 15 | |

| Glu | Gly | Ile | Arg | Glu | Trp | Trp | Asp | Leu | Lys | Pro | Gly | Ala | Pro | Lys | Pro |
|---|---|---|---|---|---|---|---|---|---|---|---|---|---|---|---|
| | | | 20 | | | | | 25 | | | | | 30 | | |

| Lys | Ala | Asn | Gln | Gln | Lys | Gln | Asp | Asp | Gly | Arg | Gly | Leu | Val | Leu | Pro |
|---|---|---|---|---|---|---|---|---|---|---|---|---|---|---|---|
| | | 35 | | | | | 40 | | | | | 45 | | | |

| Gly | Tyr | Lys | Tyr | Leu | Gly | Pro | Phe | Asn | Gly | Leu | Asp | Lys | Gly | Glu | Pro |
|---|---|---|---|---|---|---|---|---|---|---|---|---|---|---|---|
| | 50 | | | | | 55 | | | | | 60 | | | | |

| Val | Asn | Ala | Ala | Asp | Ala | Ala | Leu | Glu | His | Asp | Lys | Ala | Tyr | Asp |
|---|---|---|---|---|---|---|---|---|---|---|---|---|---|---|
| 65 | | | | 70 | | | | 75 | | | | | 80 | |

| Gln | Gln | Leu | Lys | Ala | Gly | Asp | Asn | Pro | Tyr | Leu | Arg | Tyr | Asn | His | Ala |
|---|---|---|---|---|---|---|---|---|---|---|---|---|---|---|---|
| | | | 85 | | | | | 90 | | | | | 95 | | |

| Asp | Ala | Glu | Phe | Gln | Glu | Arg | Leu | Gln | Glu | Asp | Thr | Ser | Phe | Gly | Gly |
|---|---|---|---|---|---|---|---|---|---|---|---|---|---|---|---|
| | | 100 | | | | | 105 | | | | | 110 | | | |

| Asn | Leu | Gly | Arg | Ala | Val | Phe | Gln | Ala | Lys | Lys | Arg | Val | Leu | Glu | Pro |
|---|---|---|---|---|---|---|---|---|---|---|---|---|---|---|---|
| | 115 | | | | | 120 | | | | | 125 | | | | |

| Leu | Gly | Leu | Val | Glu | Glu | Gly | Ala | Lys | Thr | Ala | Pro | Gly | Lys | Lys | Arg |
|---|---|---|---|---|---|---|---|---|---|---|---|---|---|---|---|
| | 130 | | | | | 135 | | | | | 140 | | | | |

| Pro | Val | Glu | Pro | Ser | Pro | Gln | Arg | Ser | Pro | Asp | Ser | Ser | Thr | Gly | Ile |
|---|---|---|---|---|---|---|---|---|---|---|---|---|---|---|---|
| 145 | | | | | 150 | | | | | 155 | | | | | 160 |

| Gly | Lys | Lys | Gly | Gln | Gln | Pro | Ala | Lys | Lys | Arg | Leu | Asn | Phe | Gly | Gln |
|---|---|---|---|---|---|---|---|---|---|---|---|---|---|---|---|
| | | | 165 | | | | | 170 | | | | | 175 | | |

| Thr | Gly | Asp | Ser | Glu | Ser | Val | Pro | Asp | Pro | Gln | Pro | Leu | Gly | Glu | Pro |
|---|---|---|---|---|---|---|---|---|---|---|---|---|---|---|---|
| | | | 180 | | | | | 185 | | | | | 190 | | |

| Pro | Ala | Thr | Pro | Ala | Ala | Val | Gly | Pro | Thr | Thr | Met | Ala | Ser | Gly | Gly |
|---|---|---|---|---|---|---|---|---|---|---|---|---|---|---|---|
| | | 195 | | | | | 200 | | | | | 205 | | | |

| Gly | Ala | Pro | Met | Ala | Asp | Asn | Asn | Glu | Gly | Ala | Asp | Gly | Val | Gly | Asn |
|---|---|---|---|---|---|---|---|---|---|---|---|---|---|---|---|
| | 210 | | | | | 215 | | | | | 220 | | | | |

| Ala | Ser | Gly | Asn | Trp | His | Cys | Asp | Ser | Thr | Trp | Leu | Gly | Asp | Arg | Val |
|---|---|---|---|---|---|---|---|---|---|---|---|---|---|---|---|
| 225 | | | | | 230 | | | | | 235 | | | | | 240 |

| Ile | Thr | Thr | Ser | Thr | Arg | Thr | Trp | Ala | Leu | Pro | Thr | Tyr | Asn | Asn | His |
|---|---|---|---|---|---|---|---|---|---|---|---|---|---|---|---|
| | | | | 245 | | | | | 250 | | | | | 255 | |

| Leu | Tyr | Lys | Gln | Ile | Ser | Asn | Gly | Thr | Ser | Gly | Gly | Ser | Thr | Asn | Asp |
|---|---|---|---|---|---|---|---|---|---|---|---|---|---|---|---|
| | | | 260 | | | | | 265 | | | | | 270 | | |

| Asn | Thr | Tyr | Phe | Gly | Tyr | Ser | Thr | Pro | Trp | Gly | Tyr | Phe | Asp | Phe | Asn |
|---|---|---|---|---|---|---|---|---|---|---|---|---|---|---|---|
| | | | 275 | | | | | 280 | | | | | 285 | | |

| Arg | Phe | His | Cys | His | Phe | Ser | Pro | Arg | Asp | Trp | Gln | Arg | Leu | Ile | Asn |
|---|---|---|---|---|---|---|---|---|---|---|---|---|---|---|---|
| | 290 | | | | | 295 | | | | | 300 | | | | |

| Asn | Asn | Trp | Gly | Phe | Arg | Pro | Lys | Arg | Leu | Asn | Phe | Lys | Leu | Phe | Asn |
|---|---|---|---|---|---|---|---|---|---|---|---|---|---|---|---|
| 305 | | | | | 310 | | | | | 315 | | | | | 320 |

| Ile | Gln | Val | Lys | Glu | Val | Thr | Gln | Asn | Glu | Gly | Lys | Thr | Thr | Ile | Ala |
|---|---|---|---|---|---|---|---|---|---|---|---|---|---|---|---|
| | | | | 325 | | | | | 330 | | | | | 335 | |

| Asn | Asn | Leu | Thr | Ser | Thr | Ile | Gln | Val | Phe | Thr | Asp | Ser | Glu | Tyr | Gln |
|---|---|---|---|---|---|---|---|---|---|---|---|---|---|---|---|
| | | | 340 | | | | | 345 | | | | | 350 | | |

| Leu | Pro | Tyr | Val | Leu | Gly | Ser | Ala | His | Gln | Gly | Cys | Leu | Pro | Pro | Phe |
|---|---|---|---|---|---|---|---|---|---|---|---|---|---|---|---|
| | | | 355 | | | | | 360 | | | | | 365 | | |

| Pro | Ala | Asp | Val | Phe | Met | Ile | Pro | Gln | Tyr | Gly | Tyr | Leu | Thr | Leu | Asn |

```
                370                 375                 380
Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Thr Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Asn Arg Thr Gln Asn Gln Ser Gly Ser Ala Gln Asn Lys Asp Leu Leu
                450                 455                 460

Phe Ser Arg Gly Ser Pro Ala Gly Met Ser Val Gln Pro Lys Asn Trp
465                 470                 475                 480

Leu Pro Gly Pro Cys Tyr Arg Gln Arg Val Ser Lys Thr Lys Thr
                485                 490                 495

Asp Asn Asn Asn Ser Asn Phe Thr Trp Thr Gly Ala Ser Lys Tyr Asn
                500                 505                 510

Leu Asn Gly Arg Glu Ser Ile Ile Asn Pro Gly Thr Ala Met Ala Ser
                515                 520                 525

His Lys Asp Asp Lys Asp Lys Phe Phe Pro Met Ser Gly Val Met Ile
                530                 535                 540

Phe Gly Lys Glu Ser Ala Gly Ala Ser Asn Thr Ala Leu Asp Asn Val
545                 550                 555                 560

Met Ile Thr Asp Glu Glu Ile Lys Ala Thr Asn Pro Val Ala Thr
                565                 570                 575

Glu Arg Phe Gly Thr Val Ala Val Asn Leu Gln Ser Ser Thr Asp
                580                 585                 590

Pro Ala Thr Gly Asp Val His Val Met Gly Ala Leu Pro Gly Met Val
                595                 600                 605

Trp Gln Asp Arg Asp Val Tyr Leu Gln Gly Pro Ile Trp Ala Lys Ile
                610                 615                 620

Pro His Thr Asp Gly His Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asn Pro Pro Ala Glu Phe Ser Ala Thr Lys Phe Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Val Gln Tyr Thr
                690                 695                 700

Ser Asn Tyr Ala Lys Ser Ala Asn Val Asp Phe Thr Val Asp Asn Asn
705                 710                 715                 720

Gly Leu Tyr Thr Glu Pro Arg Pro Ile Gly Thr Arg Tyr Leu Thr Arg
                725                 730                 735

Pro Leu

<210> SEQ ID NO 20
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV7R.6
```

<400> SEQUENCE: 20

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Lys Leu Arg Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415
```

-continued

```
Ser Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ala Arg Thr Gln Ser Asn Pro Gly Gly Thr Ala Gly Asn Arg Glu Leu
    450                 455                 460

Gln Phe Tyr Gln Gly Gly Pro Ser Thr Met Ala Glu Gln Ala Lys Asn
465                 470                 475                 480

Trp Leu Pro Gly Pro Cys Phe Arg Gln Gln Arg Val Ser Lys Thr Leu
                485                 490                 495

Asp Gln Asn Asn Asn Ser Asn Phe Ala Trp Thr Gly Ala Thr Lys Tyr
            500                 505                 510

His Leu Asn Gly Arg Asn Ser Leu Val Asn Pro Gly Val Ala Met Ala
        515                 520                 525

Thr His Lys Asp Asp Glu Asp Arg Phe Phe Pro Ser Ser Gly Val Leu
    530                 535                 540

Ile Phe Gly Lys Thr Gly Ala Thr Asn Lys Thr Thr Leu Glu Asn Val
545                 550                 555                 560

Leu Met Thr Asn Glu Glu Glu Ile Arg Pro Thr Asn Pro Val Ala Thr
                565                 570                 575

Glu Glu Tyr Gly Ile Val Ser Ser Asn Leu Gln Ala Ala Asn Thr Ala
            580                 585                 590

Ala Gln Thr Gln Val Val Asn Asn Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asn Pro Pro Glu Val Phe Thr Pro Ala Lys Phe Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Phe Glu Lys Gln Thr Gly Val Asp Phe Ala Val Asp Ser Gln
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 21
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV8R.6

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30
```

```
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
                180                 185                 190
Pro Ala Ala Pro Ser Gly Val Gly Pro Asn Thr Met Ala Ala Gly Gly
            195                 200                 205
Gly Ala Pro Met Ala Asp Asn Asn Glu Gly Ala Asp Gly Val Gly Ser
        210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
            275                 280                 285
Arg Phe His Cys His Phe Ser Pro Arg Asp Trp Gln Arg Leu Ile Asn
        290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
```

```
Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 22
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV9R.6

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Ala Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Ser Leu Thr Met Ala Ser Gly Gly
        195                 200                 205

Gly Ala Pro Val Ala Asp Asn Asn Glu Gly Ala Asp Gly Val Gly Ser
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Asp Tyr Gln
            340                 345                 350

Leu Pro Tyr Val Leu Gly Ser Ala His Glu Gly Cys Leu Pro Pro Phe
        355                 360                 365

Pro Ala Asp Val Phe Met Ile Pro Gln Tyr Gly Tyr Leu Thr Leu Asn
    370                 375                 380

Asp Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Glu Phe Glu Asn Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Lys Thr Ile Asn Gly Ser Gly Gln Asn Gln Gln Thr Leu Lys Phe
    450                 455                 460

Ser Val Ala Gly Pro Ser Asn Met Ala Val Gln Gly Arg Asn Tyr Ile
465                 470                 475                 480

Pro Gly Pro Ser Tyr Arg Gln Gln Arg Val Ser Thr Thr Val Thr Gln
```

```
              485                 490                 495
Asn Asn Asn Ser Glu Phe Ala Trp Pro Gly Ala Ser Trp Ala Leu
              500                 505                 510

Asn Gly Arg Asn Ser Leu Met Asn Pro Gly Pro Ala Met Ala Ser His
              515                 520                 525

Lys Glu Gly Glu Asp Arg Phe Phe Pro Leu Ser Gly Ser Leu Ile Phe
              530                 535                 540

Gly Lys Gln Gly Thr Gly Arg Asp Asn Val Asp Ala Asp Lys Val Met
545               550                 555                 560

Ile Thr Asn Glu Glu Glu Ile Lys Thr Thr Asn Pro Val Ala Thr Glu
              565                 570                 575

Ser Tyr Gly Gln Val Ala Thr Asn His Gln Ser Ala Gln Ala Gln Ala
              580                 585                 590

Gln Thr Gly Trp Val Gln Asn Gln Gly Ile Leu Pro Gly Met Val Trp
              595                 600                 605

Gln Asp Arg Asp Val Tyr Leu Gln Gly Pro Ile Trp Ala Lys Ile Pro
              610                 615                 620

His Thr Asp Gly Asn Phe His Pro Ser Pro Leu Met Gly Gly Phe Gly
625               630                 635                 640

Met Lys His Pro Pro Pro Gln Ile Leu Ile Lys Asn Thr Pro Val Pro
              645                 650                 655

Ala Asp Pro Pro Thr Ala Phe Asn Lys Asp Lys Leu Asn Ser Phe Ile
              660                 665                 670

Thr Gln Tyr Ser Thr Gly Gln Val Ser Val Glu Ile Glu Trp Glu Leu
              675                 680                 685

Gln Lys Glu Asn Ser Lys Arg Trp Asn Pro Glu Ile Gln Tyr Thr Ser
              690                 695                 700

Asn Tyr Tyr Lys Ser Asn Asn Val Glu Phe Ala Val Asn Thr Glu Gly
705               710                 715                 720

Val Tyr Ser Glu Pro Arg Pro Ile Gly Thr Arg Tyr Leu Thr Arg Asn
              725                 730                 735

Leu

<210> SEQ ID NO 23
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV1R.7

<400> SEQUENCE: 23

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
              20                  25                  30

Lys Ala Asn Gln Gln Lys Gln Asp Asp Gly Arg Gly Leu Val Leu Pro
              35                  40                  45

Gly Tyr Lys Tyr Leu Gly Pro Phe Asn Gly Leu Asp Lys Gly Glu Pro
          50                  55                  60

Val Asn Ala Ala Asp Ala Ala Ala Leu Glu His Asp Lys Ala Tyr Asp
65              70                  75                  80

Gln Gln Leu Lys Ala Gly Asp Asn Pro Tyr Leu Arg Tyr Asn His Ala
              85                  90                  95

Asp Ala Glu Phe Gln Glu Arg Leu Gln Glu Asp Thr Ser Phe Gly Gly
```

```
                100                 105                 110
Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Thr Pro Ala Ala Val Gly Pro Thr Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Thr Phe Ser Tyr
                405                 410                 415

Thr Phe Glu Glu Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Asn Arg Thr Gln Asn Gln Ser Gly Ser Ala Gln Asn Lys Asp Leu Leu
    450                 455                 460

Phe Ser Arg Gly Ser Pro Ala Gly Met Ser Val Gln Pro Lys Asn Trp
465                 470                 475                 480

Leu Pro Gly Pro Cys Tyr Arg Gln Gln Arg Val Ser Lys Thr Lys Thr
                485                 490                 495

Asp Asn Asn Asn Ser Asn Phe Thr Trp Thr Gly Ala Ser Lys Tyr Asn
            500                 505                 510

Leu Asn Gly Arg Glu Ser Ile Ile Asn Pro Gly Thr Ala Met Ala Ser
        515                 520                 525
```

```
His Lys Asp Asp Glu Asp Lys Phe Phe Pro Met Ser Gly Val Met Ile
            530                 535                 540

Phe Gly Lys Glu Ser Ala Gly Ala Ser Asn Thr Ala Leu Asp Asn Val
545                 550                 555                 560

Met Ile Thr Asp Glu Glu Ile Lys Ala Thr Asn Pro Val Ala Thr
            565                 570                 575

Glu Arg Phe Gly Thr Val Ala Val Asn Phe Gln Ser Ser Thr Asp
            580                 585                 590

Pro Ala Thr Gly Asp Val His Ala Met Gly Ala Leu Pro Gly Met Val
            595                 600                 605

Trp Gln Asp Arg Asp Val Tyr Leu Gln Gly Pro Ile Trp Ala Lys Ile
            610                 615                 620

Pro His Thr Asp Gly His Phe His Pro Ser Pro Leu Met Gly Gly Phe
625                 630                 635                 640

Gly Leu Lys Asn Pro Pro Gln Ile Leu Ile Lys Asn Thr Pro Val
            645                 650                 655

Pro Ala Asn Pro Pro Ala Glu Phe Ser Ala Thr Lys Phe Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Val Gln Tyr Thr
690                 695                 700

Ser Asn Tyr Ala Lys Ser Ala Asn Val Asp Phe Thr Val Asp Asn Asn
705                 710                 715                 720

Gly Leu Tyr Thr Glu Pro Arg Pro Ile Gly Thr Arg Tyr Leu Thr Arg
            725                 730                 735

Pro Leu

<210> SEQ ID NO 24
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV2R.7

<400> SEQUENCE: 24

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140
```

-continued

Pro Val Glu Pro Ser Pro Gln Arg Ser Glu Pro Asp Ser Ser Thr Gly
145                 150                 155                 160

Thr Gly Lys Lys Gly Gln Gln Pro Ala Arg Lys Arg Leu Asn Phe Gly
                165                 170                 175

Gln Thr Gly Asp Ala Asp Ser Val Pro Asp Pro Gln Pro Ile Gly Gln
            180                 185                 190

Pro Pro Ala Ala Pro Ser Gly Leu Gly Thr Asn Thr Met Ala Ala Gly
            195                 200                 205

Ser Gly Ala Pro Met Ala Asp Asn Asn Glu Gly Ala Asp Gly Val Gly
        210                 215                 220

Ser Ser Ser Gly Asn Trp His Cys Asp Ser Thr Trp Met Gly Asp Arg
225                 230                 235                 240

Val Ile Thr Thr Ser Thr Arg Thr Trp Ala Leu Pro Thr Tyr Asn Asn
                245                 250                 255

His Leu Tyr Lys Gln Ile Ser Asn Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Val Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Thr Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Asn Thr Pro Ser Gly Thr Thr Thr Gln Ser Arg Leu Gln
    450                 455                 460

Phe Ser Gln Ala Gly Ala Ser Asp Ile Arg Asp Gln Ser Arg Asn Trp
465                 470                 475                 480

Leu Pro Gly Pro Cys Tyr Arg Gln Gln Arg Val Ser Lys Thr Ser Ala
                485                 490                 495

Asp Asn Asn Asn Ser Glu Tyr Ser Trp Thr Gly Ala Thr Lys Tyr His
            500                 505                 510

Leu Asn Gly Arg Asp Ser Leu Val Asn Pro Gly Pro Ala Met Ala Ser
        515                 520                 525

His Lys Asp Asp Glu Glu Lys Phe Phe Pro Gln Ser Gly Val Leu Ile
    530                 535                 540

Phe Gly Lys Gln Gly Ser Glu Lys Thr Asn Val Asp Ile Glu Lys Val
545                 550                 555                 560

```
Met Ile Thr Asp Glu Glu Ile Arg Thr Thr Asn Pro Val Ala Thr
                565                 570                 575

Glu Gln Tyr Gly Ser Val Ser Thr Asn Leu Gln Arg Gly Asn Arg Gln
            580                 585                 590

Ala Ala Thr Ala Asp Val Asn Thr Gln Gly Val Leu Pro Gly Met Val
            595                 600                 605

Trp Gln Asp Arg Asp Val Tyr Leu Gln Gly Pro Ile Trp Ala Lys Ile
    610                 615                 620

Pro His Thr Asp Gly His Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asn Pro Ser Thr Thr Phe Ser Ala Ala Lys Phe Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Asn Lys Ser Val Asn Val Asp Phe Thr Val Asp Thr Asn
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 25
<211> LENGTH: 739
<212> TYPE: PRT
<213> ORGANISM: Artificial Sequence
<220> FEATURE:
<223> OTHER INFORMATION: Synthetically constructed adeno-associated
      virus capsid protein AAV3R.7

<400> SEQUENCE: 25

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Pro Ser Pro Gln Glu Ser Pro Asp Ser Ser Thr Gly Val
145                 150                 155                 160

Gly Lys Lys Gly Lys Gln Pro Ala Arg Lys Arg Leu Asn Phe Gly Gln
                165                 170                 175
```

```
Thr Gly Asp Ser Glu Ser Val Pro Asp Pro Gln Pro Ile Gly Glu Pro
            180                 185                 190

Pro Ala Ala Pro Thr Ser Leu Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Lys Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Val Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Asn Arg Thr Gln Gly Thr Thr Ser Gly Thr Thr Asn Gln Ser Arg Leu
    450                 455                 460

Leu Phe Ser Gln Ala Gly Pro Gln Ser Met Ser Leu Gln Ala Arg Asn
465                 470                 475                 480

Trp Leu Pro Gly Pro Cys Tyr Arg Gln Gln Arg Leu Ser Lys Thr Ala
                485                 490                 495

Asn Asp Asn Asn Asn Ser Asn Phe Pro Trp Thr Ala Ala Ser Lys Tyr
            500                 505                 510

His Leu Asn Gly Arg Asp Ser Leu Val Asn Pro Gly Pro Ala Met Ala
        515                 520                 525

Ser His Lys Asp Asp Glu Glu Lys Phe Phe Pro Met His Gly Asn Leu
    530                 535                 540

Ile Phe Gly Lys Glu Gly Thr Thr Ala Ser Asn Ala Glu Leu Asp Asn
545                 550                 555                 560

Val Met Ile Thr Asp Glu Glu Ile Arg Thr Thr Asn Pro Val Ala
                565                 570                 575

Thr Glu Gln Tyr Gly Thr Val Ala Asn Asn Leu Gln Ser Ser Asn Thr
            580                 585                 590

Ala Pro Thr Thr Arg Thr Val Asn Asp Gln Gly Ala Leu Pro Gly Met
```

```
            595                 600                 605
Val Trp Gln Asp Arg Asp Val Tyr Leu Gln Gly Pro Ile Trp Ala Lys
        610                 615                 620

Ile Pro His Thr Asp Gly His Phe His Pro Ser Pro Leu Met Gly Gly
625                 630                 635                 640

Phe Gly Leu Lys His Pro Pro Gln Ile Met Ile Lys Asn Thr Pro
            645                 650                 655

Val Pro Ala Asn Pro Pro Thr Thr Phe Ser Pro Ala Lys Phe Ala Ser
            660                 665                 670

Phe Ile Thr Gln Tyr Ser Thr Gly Gln Val Ser Val Glu Ile Glu Trp
            675                 680                 685

Glu Leu Gln Lys Glu Asn Ser Lys Arg Trp Asn Pro Glu Ile Gln Tyr
        690                 695                 700

Thr Ser Asn Tyr Asn Lys Ser Val Asn Val Asp Phe Thr Val Asp Thr
705                 710                 715                 720

Asn Gly Val Tyr Ser Glu Pro Arg Pro Ile Gly Thr Arg Tyr Leu Thr
            725                 730                 735

Arg Asn Leu

<210> SEQ ID NO 26
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV6R.7

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Thr Pro Ala Ala Val Gly Pro Thr Thr Met Ala Ala Gly Gly
        195                 200                 205

Gly Ala Pro Met Ala Asp Asn Asn Glu Gly Ala Asp Gly Val Gly Ser
```

```
            210                 215                 220
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Lys Thr Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Thr Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Asn Arg Thr Gln Asn Gln Ser Gly Ser Ala Gln Asn Lys Asp Leu Leu
                450                 455                 460

Phe Ser Arg Gly Ser Pro Ala Gly Met Ser Val Gln Pro Lys Asn Trp
465                 470                 475                 480

Leu Pro Gly Pro Cys Tyr Arg Gln Gln Arg Val Ser Lys Thr Lys Thr
                485                 490                 495

Asp Asn Asn Asn Ser Asn Phe Thr Trp Thr Gly Ala Ser Lys Tyr Asn
                500                 505                 510

Leu Asn Gly Arg Glu Ser Ile Ile Asn Pro Gly Thr Ala Met Ala Ser
                515                 520                 525

His Lys Asp Asp Lys Asp Lys Phe Phe Pro Met Ser Gly Val Met Ile
                530                 535                 540

Phe Gly Lys Glu Ser Ala Gly Ala Ser Asn Thr Ala Leu Asp Asn Val
545                 550                 555                 560

Met Ile Thr Asp Glu Glu Glu Ile Lys Ala Thr Asn Pro Val Ala Thr
                565                 570                 575

Glu Arg Phe Gly Thr Val Ala Val Asn Leu Gln Ser Ser Ser Thr Asp
                580                 585                 590

Pro Ala Thr Gly Asp Val His Val Met Gly Ala Leu Pro Gly Met Val
                595                 600                 605

Trp Gln Asp Arg Asp Val Tyr Leu Gln Gly Pro Ile Trp Ala Lys Ile
610                 615                 620

Pro His Thr Asp Gly His Phe His Pro Ser Pro Leu Met Gly Gly Phe
625                 630                 635                 640
```

-continued

```
Gly Leu Lys His Pro Pro Gln Ile Leu Ile Lys Asn Thr Pro Val
                645                 650                 655

Pro Ala Asn Pro Pro Ala Glu Phe Ser Ala Thr Lys Phe Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Val Gln Tyr Thr
    690                 695                 700

Ser Asn Tyr Ala Lys Ser Ala Asn Val Asp Phe Thr Val Asp Asn Asn
705                 710                 715                 720

Gly Leu Tyr Thr Glu Pro Arg Pro Ile Gly Thr Arg Tyr Leu Thr Arg
                725                 730                 735

Pro Leu

<210> SEQ ID NO 27
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV7R.7

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

```
Leu Tyr Lys Gln Ile Ser Asn Gly Thr Ser Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Lys Leu Arg Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Ser Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ala Arg Thr Gln Ser Asn Pro Gly Gly Thr Ala Gly Asn Arg Glu Leu
            450                 455                 460

Gln Phe Tyr Gln Gly Gly Pro Ser Thr Met Ala Glu Gln Ala Lys Asn
465                 470                 475                 480

Trp Leu Pro Gly Pro Cys Phe Arg Gln Gln Arg Val Ser Lys Thr Leu
                485                 490                 495

Asp Gln Asn Asn Asn Ser Asn Phe Ala Trp Thr Gly Ala Thr Lys Tyr
            500                 505                 510

His Leu Asn Gly Arg Asn Ser Leu Val Asn Pro Gly Val Ala Met Ala
            515                 520                 525

Thr His Lys Asp Asp Glu Asp Arg Phe Phe Pro Ser Ser Gly Val Leu
            530                 535                 540

Ile Phe Gly Lys Thr Gly Ala Thr Asn Lys Thr Thr Leu Glu Asn Val
545                 550                 555                 560

Leu Met Thr Asn Glu Glu Ile Arg Pro Thr Asn Pro Val Ala Thr
            565                 570                 575

Glu Glu Tyr Gly Ile Val Ser Ser Asn Leu Gln Ala Ala Asn Thr Ala
            580                 585                 590

Ala Gln Thr Gln Val Val Asn Asn Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asn Pro Pro Glu Val Phe Thr Pro Ala Lys Phe Ala Ser Phe
            660                 665                 670
```

```
Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Phe Glu Lys Gln Thr Gly Val Asp Phe Ala Val Asp Ser Gln
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 28
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV8R.7

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285
```

-continued

```
Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
```

-continued

```
        705                 710                 715                 720
Gly Val Tyr Ser Glu Pro Arg Pro Ile Gly Thr Arg Tyr Leu Thr Arg
                    725                 730                 735
Asn Leu

<210> SEQ ID NO 29
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV9R.7

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Ala Gln Pro Ala Lys Lys Arg Leu Asn Phe Gly Gln
                165                 170                 175

Thr Gly Asp Thr Glu Ser Val Pro Asp Pro Gln Pro Ile Gly Glu Pro
            180                 185                 190

Pro Ala Ala Pro Ser Gly Val Gly Ser Leu Thr Met Ala Ala Gly Gly
        195                 200                 205

Gly Ala Pro Val Ala Asp Asn Asn Glu Gly Ala Asp Gly Val Gly Ser
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
```

```
                    325                 330                 335
Asn Asn Leu Thr Ser Thr Ile Gln Val Phe Thr Asp Ser Asp Tyr Gln
                340                 345                 350
Leu Pro Tyr Val Leu Gly Ser Ala His Glu Gly Cys Leu Pro Pro Phe
                355                 360                 365
Pro Ala Asp Val Phe Met Ile Pro Gln Tyr Gly Tyr Leu Thr Leu Asn
                370                 375                 380
Asp Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Ser Tyr
                405                 410                 415
Glu Phe Glu Asn Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Lys Thr Ile Asn Gly Ser Gly Gln Asn Gln Gln Thr Leu Lys Phe
                450                 455                 460
Ser Val Ala Gly Pro Ser Asn Met Ala Val Gln Gly Arg Asn Tyr Ile
465                 470                 475                 480
Pro Gly Pro Ser Tyr Arg Gln Gln Arg Val Ser Thr Thr Val Thr Gln
                485                 490                 495
Asn Asn Asn Ser Glu Phe Ala Trp Pro Gly Ala Ser Ser Trp Ala Leu
                500                 505                 510
Asn Gly Arg Asn Ser Leu Met Asn Pro Gly Pro Ala Met Ala Ser His
                515                 520                 525
Lys Glu Gly Glu Asp Arg Phe Phe Pro Leu Ser Gly Ser Leu Ile Phe
                530                 535                 540
Gly Lys Gln Gly Thr Gly Arg Asp Asn Val Asp Ala Asp Lys Val Met
545                 550                 555                 560
Ile Thr Asn Glu Glu Glu Ile Lys Thr Thr Asn Pro Val Ala Thr Glu
                565                 570                 575
Ser Tyr Gly Gln Val Ala Thr Asn His Gln Ser Ala Gln Ala Gln Ala
                580                 585                 590
Gln Thr Gly Trp Val Gln Asn Gln Gly Ile Leu Pro Gly Met Val Trp
                595                 600                 605
Gln Asp Arg Asp Val Tyr Leu Gln Gly Pro Ile Trp Ala Lys Ile Pro
                610                 615                 620
His Thr Asp Gly Asn Phe His Pro Ser Pro Leu Met Gly Gly Phe Gly
625                 630                 635                 640
Met Lys His Pro Pro Gln Ile Leu Ile Lys Asn Thr Pro Val Pro
                645                 650                 655
Ala Asp Pro Pro Thr Ala Phe Asn Lys Asp Lys Leu Asn Ser Phe Ile
                660                 665                 670
Thr Gln Tyr Ser Thr Gly Gln Val Ser Val Glu Ile Glu Trp Glu Leu
                675                 680                 685
Gln Lys Glu Asn Ser Lys Arg Trp Asn Pro Glu Ile Gln Tyr Thr Ser
                690                 695                 700
Asn Tyr Tyr Lys Ser Asn Asn Val Glu Phe Ala Val Asn Thr Glu Gly
705                 710                 715                 720
Val Tyr Ser Glu Pro Arg Pro Ile Gly Thr Arg Tyr Leu Thr Arg Asn
                725                 730                 735

Leu
```

<210> SEQ ID NO 30
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV1RX'

<400> SEQUENCE: 30

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365
```

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
    450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Glu Asp Lys Phe Phe Pro Met Ser Gly Val Met Ile Phe
    530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Phe Gln Ser Ser Ser Thr Asp Pro
            580                 585                 590

Ala Thr Gly Asp Val His Ala Met Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys Asn Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu

<210> SEQ ID NO 31
<211> LENGTH: 737
<212> TYPE: PRT
<213> ORGANISM: Artificial Sequence
<220> FEATURE:
<223> OTHER INFORMATION: Synthetically constructed adeno-associated virus capsid protein AAV2RX'

<400> SEQUENCE: 31

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Gln Asn Asp Gly Thr Thr Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Thr Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Arg Thr Asn Thr Pro Ser Gly Thr Thr Thr Gln Ser Arg Leu Gln Phe
    450                 455                 460
Ser Gln Ala Gly Ala Ser Asp Ile Arg Asp Gln Ser Arg Asn Trp Leu
465                 470                 475                 480
Pro Gly Pro Cys Tyr Arg Gln Gln Arg Val Ser Lys Thr Ser Ala Asp
                485                 490                 495
Asn Asn Asn Ser Glu Tyr Ser Trp Thr Gly Ala Thr Lys Tyr His Leu
            500                 505                 510
Asn Gly Arg Asp Ser Leu Val Asn Pro Gly Pro Ala Met Ala Ser His
        515                 520                 525
Lys Asp Asp Glu Glu Lys Phe Phe Pro Gln Ser Gly Val Leu Ile Phe
    530                 535                 540
Gly Lys Gln Gly Ser Glu Lys Thr Asn Val Asp Ile Glu Lys Val Met
545                 550                 555                 560
Ile Thr Asp Glu Glu Glu Ile Arg Thr Thr Asn Pro Val Ala Thr Glu
                565                 570                 575
Gln Tyr Gly Ser Val Ser Thr Asn Leu Gln Arg Gly Asn Arg Gln Ala
            580                 585                 590
Ala Thr Ala Asp Val Asn Thr Gln Gly Val Leu Pro Gly Met Val Trp
        595                 600                 605
Gln Asp Arg Asp Val Tyr Leu Gln Gly Pro Ile Trp Ala Lys Ile Pro
    610                 615                 620
His Thr Asp Gly His Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Ser Thr Thr Phe Ser Ala Ala Lys Phe Ala Ser Phe Ile
            660                 665                 670
Thr Gln Tyr Ser Thr Gly Gln Val Ser Val Glu Ile Glu Trp Glu Leu
        675                 680                 685
Gln Lys Glu Asn Ser Lys Arg Trp Asn Pro Glu Ile Gln Tyr Thr Ser
    690                 695                 700
Asn Tyr Asn Lys Ser Val Asn Val Asp Phe Thr Val Asp Thr Asn Gly
705                 710                 715                 720
Val Tyr Ser Glu Pro Arg Pro Ile Gly Thr Arg Tyr Leu Thr Arg Asn
                725                 730                 735
Leu

<210> SEQ ID NO 32
<211> LENGTH: 738
<212> TYPE: PRT
<213> ORGANISM: Artificial Sequence
<220> FEATURE:
<223> OTHER INFORMATION: Synthetically constructed adeno-associated
      virus capsid protein AAV3RX'

<400> SEQUENCE: 32

Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Val Gln Pro
             20                  25                  30

Lys Ala Asn Gln Gln His Gln Asp Asn Arg Arg Gly Leu Val Leu Pro
         35                  40                  45

Gly Tyr Lys Tyr Leu Gly Pro Gly Asn Gly Leu Asp Lys Gly Glu Pro
     50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Ser Phe Lys Leu Phe Asn Ile
305                 310                 315                 320

Gln Val Lys Glu Val Thr Gln Asn Asp Gly Thr Thr Thr Ile Ala Asn
                325                 330                 335

Asn Leu Thr Ser Thr Val Gln Val Phe Thr Asp Ser Glu Tyr Gln Leu
        340                 345                 350

Pro Tyr Val Leu Gly Ser Ala His Gln Gly Cys Leu Pro Pro Phe Pro
    355                 360                 365

Ala Asp Val Phe Met Val Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
```

```
            435                 440                 445
Arg Thr Gln Gly Thr Thr Ser Gly Thr Thr Asn Gln Ser Arg Leu Leu
450                 455                 460

Phe Ser Gln Ala Gly Pro Gln Ser Met Ser Leu Gln Ala Arg Asn Trp
465                 470                 475                 480

Leu Pro Gly Pro Cys Tyr Arg Gln Gln Arg Leu Ser Lys Thr Ala Asn
                485                 490                 495

Asp Asn Asn Asn Ser Asn Phe Pro Trp Thr Ala Ala Ser Lys Tyr His
                500                 505                 510

Leu Asn Gly Arg Asp Ser Leu Val Asn Pro Gly Pro Ala Met Ala Ser
                515                 520                 525

His Lys Asp Asp Glu Lys Phe Phe Pro Met His Gly Asn Leu Ile
530                 535                 540

Phe Gly Lys Glu Gly Thr Thr Ala Ser Asn Ala Glu Leu Asp Asn Val
545                 550                 555                 560

Met Ile Thr Asp Glu Glu Glu Ile Arg Thr Thr Asn Pro Val Ala Thr
                565                 570                 575

Glu Gln Tyr Gly Thr Val Ala Asn Asn Leu Gln Ser Ser Asn Thr Ala
                580                 585                 590

Pro Thr Thr Arg Thr Val Asn Asp Gln Gly Ala Leu Pro Gly Met Val
                595                 600                 605

Trp Gln Asp Arg Asp Val Tyr Leu Gln Gly Pro Ile Trp Ala Lys Ile
610                 615                 620

Pro His Thr Asp Gly His Phe His Pro Ser Pro Leu Met Gly Gly Phe
625                 630                 635                 640

Gly Leu Lys His Pro Pro Pro Gln Ile Met Ile Lys Asn Thr Pro Val
                645                 650                 655

Pro Ala Asn Pro Pro Thr Thr Phe Ser Pro Ala Lys Phe Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700

Ser Asn Tyr Asn Lys Ser Val Asn Val Asp Phe Thr Val Asp Thr Asn
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 33
<211> LENGTH: 737
<212> TYPE: PRT
<213> ORGANISM: Artificial Sequence
<220> FEATURE:
<223> OTHER INFORMATION: Synthetically constructed adeno-associated
      virus capsid protein AAV6RX'

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
```

```
                50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                     85                  90                  95

Asp Ala Glu Phe Gln Glu Arg Leu Gln Glu Asp Thr Ser Phe Gly Gly
                    100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Asn
                435                 440                 445

Arg Thr Gln Asn Gln Ser Gly Ser Ala Gln Asn Lys Asp Leu Leu Phe
            450                 455                 460

Ser Arg Gly Ser Pro Ala Gly Met Ser Val Gln Pro Lys Asn Trp Leu
465                 470                 475                 480
```

```
Pro Gly Pro Cys Tyr Arg Gln Gln Arg Val Ser Lys Thr Lys Thr Asp
            485                 490                 495

Asn Asn Asn Ser Asn Phe Thr Trp Thr Gly Ala Ser Lys Tyr Asn Leu
        500                 505                 510

Asn Gly Arg Glu Ser Ile Ile Asn Pro Gly Thr Ala Met Ala Ser His
        515                 520                 525

Lys Asp Asp Lys Asp Lys Phe Phe Pro Met Ser Gly Val Met Ile Phe
530                 535                 540

Gly Lys Glu Ser Ala Gly Ala Ser Asn Thr Ala Leu Asp Asn Val Met
545                 550                 555                 560

Ile Thr Asp Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
            595                 600                 605

Gln Asp Arg Asp Val Tyr Leu Gln Gly Pro Ile Trp Ala Lys Ile Pro
        610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu
```

<210> SEQ ID NO 34
<211> LENGTH: 736
<212> TYPE: PRT
<213> ORGANISM: Artificial Sequence
<220> FEATURE:
<223> OTHER INFORMATION: Synthetically constructed adeno-associated
      virus capsid protein AAV9RX'

<400> SEQUENCE: 34

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95
```

```
Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510
```

-continued

```
Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 35
<211> LENGTH: 4
<212> TYPE: PRT
<213> ORGANISM: Artificial Sequence
<220> FEATURE:
<223> OTHER INFORMATION: Synthetically constructed adeno-associated
      virus capsid protein sequence
<220> FEATURE:
<221> NAME/KEY: misc_feature
<222> LOCATION: (1)..(1)
<223> OTHER INFORMATION: Xaa can be any naturally occurring amino acid
      other than Ser
<220> FEATURE:
<221> NAME/KEY: misc_feature
<222> LOCATION: (2)..(2)
<223> OTHER INFORMATION: Xaa can be any naturally occurring amino acid
      other than Ala
<220> FEATURE:
<221> NAME/KEY: misc_feature
<222> LOCATION: (3)..(3)
<223> OTHER INFORMATION: Xaa can be any naturally occurring amino acid
      other than Ser
<220> FEATURE:
<221> NAME/KEY: misc_feature
<222> LOCATION: (4)..(4)
<223> OTHER INFORMATION: Xaa can be any naturally occurring amino acid
      other than Thr

<400> SEQUENCE: 35

Xaa Xaa Xaa Xaa
1

<210> SEQ ID NO 36
<211> LENGTH: 25
```

```
<212> TYPE: DNA
<213> ORGANISM: Artificial Sequence
<220> FEATURE:
<223> OTHER INFORMATION: Synthetically constructed AAV2 inverted
      terminal repeat forward PCR primer

<400> SEQUENCE: 36
aacatgctac gcagagaggg agtgg                                              25

<210> SEQ ID NO 37
<211> LENGTH: 29
<212> TYPE: DNA
<213> ORGANISM: Artificial Sequence
<220> FEATURE:
<223> OTHER INFORMATION: Synthetically constructed AAV2 inverted
      terminal repeat reverse PCR primer

<400> SEQUENCE: 37
catgagacaa ggaacccta gtgatggag                                           29

<210> SEQ ID NO 38
<211> LENGTH: 24
<212> TYPE: DNA
<213> ORGANISM: Artificial Sequence
<220> FEATURE:
<223> OTHER INFORMATION: Synthetically constructed luciferase transgene
      forward PCR primer

<400> SEQUENCE: 38
aaaagcactc tgattgacaa atac                                               24

<210> SEQ ID NO 39
<211> LENGTH: 22
<212> TYPE: DNA
<213> ORGANISM: Artificial Sequence
<220> FEATURE:
<223> OTHER INFORMATION: Synthetically constructed luciferase transgene
      reverse PCR primer

<400> SEQUENCE: 39
ccttcgcttc aaaaaatgga ac                                                 22

<210> SEQ ID NO 40
<211> LENGTH: 23
<212> TYPE: DNA
<213> ORGANISM: Artificial Sequence
<220> FEATURE:
<223> OTHER INFORMATION: Synthetically constructed mouse lamin B2
      housekeeping gene forward PCR primer

<400> SEQUENCE: 40
ggacccaagg actacctcaa ggg                                                23

<210> SEQ ID NO 41
<211> LENGTH: 22
<212> TYPE: DNA
<213> ORGANISM: Artificial Sequence
<220> FEATURE:
<223> OTHER INFORMATION: Synthetically constructed mouse lamin B2
      housekeeping gene reverse PCR primer

<400> SEQUENCE: 41
agggcacctc catctcggaa ac                                                 22

<210> SEQ ID NO 42
<211> LENGTH: 4
<212> TYPE: PRT
```

```
<213> ORGANISM: Artificial Sequence
<220> FEATURE:
<223> OTHER INFORMATION: Synthetically constructed adeno-associated
      virus capsid protein sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 42

Asn Xaa Xaa Xaa
1

<210> SEQ ID NO 43
<211> LENGTH: 4
<212> TYPE: PRT
<213> ORGANISM: Artificial Sequence
<220> FEATURE:
<223> OTHER INFORMATION: Synthetically constructed adeno-associated
      virus capsid protein sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 43

Xaa Gly Xaa Xaa
1

<210> SEQ ID NO 44
<211> LENGTH: 4
<212> TYPE: PRT
<213> ORGANISM: Artificial Sequence
<220> FEATURE:
<223> OTHER INFORMATION: Synthetically constructed adeno-associated
      virus capsid protein sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 44

Xaa Xaa Thr Xaa
1

<210> SEQ ID NO 45
<211> LENGTH: 4
<212> TYPE: PRT
<213> ORGANISM: Artificial Sequence
<220> FEATURE:
<223> OTHER INFORMATION: Synthetically constructed adeno-associated
      virus capsid protein sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 45

Xaa Xaa Xaa Ser
1

<210> SEQ ID NO 46
<211> LENGTH: 4
```

```
<212> TYPE: PRT
<213> ORGANISM: Artificial Sequence
<220> FEATURE:
<223> OTHER INFORMATION: Synthetically constructed adeno-associated
      virus capsid protein sequence

<400> SEQUENCE: 46

Asn Gly Thr Ser
1

<210> SEQ ID NO 47
<211> LENGTH: 18
<212> TYPE: PRT
<213> ORGANISM: adeno-associated virus 4

<400> SEQUENCE: 47

Arg Leu Gly Glu Ser Leu Gln Ser Asn Thr Tyr Asn Gly Phe Ser Thr
1               5                   10                  15

Pro Trp

<210> SEQ ID NO 48
<211> LENGTH: 22
<212> TYPE: PRT
<213> ORGANISM: Unknown
<220> FEATURE:
<223> OTHER INFORMATION: Adeno-associated virus 5

<400> SEQUENCE: 48

Glu Ile Lys Ser Gly Ser Val Asp Gly Ser Asn Ala Asn Ala Tyr Phe
1               5                   10                  15

Gly Tyr Ser Thr Pro Trp
            20

<210> SEQ ID NO 49
<211> LENGTH: 23
<212> TYPE: PRT
<213> ORGANISM: Unknown
<220> FEATURE:
<223> OTHER INFORMATION: Adeno-associated virus AAVrh.8

<400> SEQUENCE: 49

Gln Ile Ser Asn Gly Thr Ser Gly Gly Ser Thr Asn Asp Asn Thr Tyr
1               5                   10                  15

Phe Gly Tyr Ser Thr Pro Trp
            20

<210> SEQ ID NO 50
<211> LENGTH: 23
<212> TYPE: PRT
<213> ORGANISM: Unknown
<220> FEATURE:
<223> OTHER INFORMATION: Adeno-associated virus AAVrh.39

<400> SEQUENCE: 50

Gln Ile Ser Asn Gly Thr Ser Gly Gly Ser Thr Asn Asp Asn Thr Tyr
1               5                   10                  15

Phe Gly Tyr Ser Thr Pro Trp
            20

<210> SEQ ID NO 51
<211> LENGTH: 23
<212> TYPE: PRT
<213> ORGANISM: Unknown
<220> FEATURE:
<223> OTHER INFORMATION: Adeno-associated virus AAVrh.43
```

```
<400> SEQUENCE: 51

Gln Ile Ser Asn Gly Thr Ser Phe Phe Ala Thr Asn Asp Asn Thr Tyr
1               5                   10                  15

Phe Gly Tyr Ser Thr Pro Trp
            20
```